US008562970B2

(12) United States Patent
Parrington et al.

(10) Patent No.: US 8,562,970 B2
(45) **Date of Patent: *Oct. 22, 2013**

(54) MODIFIED CEA/B7 VECTOR

(75) Inventors: Mark Parrington, Bradford (CA); Linong Zhang, Maple (CA); Benjamin Rovinski, Thornhill (CA); Linda Gritz, Somerville, MA (US); Patricia Greenhaigh, Bedford, MA (US)

(73) Assignee: Sanofi Pasteur Limited, Toronto, Ontario (CA)

( * ) Notice: Subject to any disclaimer, the term of this patent is extended or adjusted under 35 U.S.C. 154(b) by 675 days.

This patent is subject to a terminal disclaimer.

(21) Appl. No.: 10/575,060

(22) PCT Filed: Oct. 6, 2004

(86) PCT No.: PCT/US2004/033145

§ 371 (c)(1), (2), (4) Date: Dec. 26, 2007

(87) PCT Pub. No.: WO2005/035773

PCT Pub. Date: Apr. 21, 2005

(65) Prior Publication Data

US 2008/0113928 A1 May 15, 2008

Related U.S. Application Data

(60) Provisional application No. 60/509,593, filed on Oct. 8, 2003.

(51) Int. Cl.

| | |
|---|---|
| ***A01N 63/00*** | (2006.01) |
| ***C12N 15/00*** | (2006.01) |
| ***C12N 15/86*** | (2006.01) |
| ***C07H 21/02*** | (2006.01) |
| ***C07H 21/04*** | (2006.01) |

(52) U.S. Cl.

USPC ...... 424/93.2; 435/320.1; 435/456; 536/23.1; 536/23.5

(58) Field of Classification Search

USPC .............. 424/93.2; 435/320.1, 456; 536/23.1, 536/23.5

See application file for complete search history.

(56) References Cited

U.S. PATENT DOCUMENTS

| | | | | |
|---|---|---|---|---|
| 4,603,112 | A | 7/1986 | Paoletti et al. | |
| 4,722,848 | A | 2/1988 | Paoletti et al. | |
| 4,769,330 | A | 9/1988 | Paoletti et al. | |
| 4,882,278 | A | 11/1989 | Mekalanos et al. | |
| 4,923,808 | A * | 5/1990 | Matteucci | 435/69.8 |
| 4,956,281 | A | 9/1990 | Wallner et al. | |
| 5,093,258 | A | 3/1992 | Cohen et al. | |
| 5,110,587 | A | 5/1992 | Paoletti et al. | |
| 5,122,599 | A | 6/1992 | Barnett et al. | |
| 5,141,742 | A | 8/1992 | Brown et al. | |
| 5,155,020 | A | 10/1992 | Paoletti et al. | |
| 5,174,993 | A | 12/1992 | Paoletti et al. | |
| 5,204,243 | A | 4/1993 | Paoletti et al. | |
| 5,225,336 | A | 7/1993 | Paoletti et al. | |
| 5,274,087 | A | 12/1993 | Barnett et al. | |
| 5,279,833 | A | 1/1994 | Rose | |
| 5,283,185 | A | 2/1994 | Epand et al. | |
| 5,342,774 | A | 8/1994 | Boon et al. | |
| 5,348,887 | A | 9/1994 | Bumol et al. | |
| 5,364,773 | A | 11/1994 | Paoletti et al. | |
| 5,378,457 | A | 1/1995 | Paoletti et al. | |
| 5,405,940 | A | 4/1995 | Boon et al. | |
| 5,453,364 | A | 9/1995 | Paoletti | |
| 5,462,871 | A | 10/1995 | Boon-Falleur et al. | |
| 5,494,807 | A | 2/1996 | Paoletti et al. | |
| 5,504,005 | A | 4/1996 | Bloom et al. | |
| 5,505,941 | A | 4/1996 | Paoletti et al. | |
| 5,527,928 | A | 6/1996 | Nantz et al. | |
| 5,547,853 | A | 8/1996 | Wallner et al. | |
| 5,554,506 | A | 9/1996 | Van der Bruggen et al. | |
| 5,554,724 | A | 9/1996 | Melief et al. | |
| 5,571,710 | A | 11/1996 | Barnett et al. | |
| 5,585,461 | A | 12/1996 | Townsend et al. | |
| 5,589,466 | A | 12/1996 | Felgner et al. | |
| 5,591,430 | A | 1/1997 | Townsend et al. | |
| 5,612,216 | A | 3/1997 | Springer et al. | |
| 5,631,010 | A | 5/1997 | Mekalanos et al. | |
| 5,651,981 | A | 7/1997 | Ashley et al. | |
| 5,686,068 | A | 11/1997 | Melief et al. | |
| 5,695,994 | A | 12/1997 | Boon-Falleur et al. | |
| 5,698,530 | A | 12/1997 | Schlom et al. | |
| 5,703,055 | A | 12/1997 | Felgner et al. | |
| 5,707,618 | A | 1/1998 | Armentano et al. | |

(Continued)

FOREIGN PATENT DOCUMENTS

| | | | |
|---|---|---|---|
| WO | WO 91/11194 | A1 | 8/1991 |
| WO | WO 96/11279 | A2 | 4/1996 |
| WO | WO 98/29556 | A1 | 12/1996 |
| WO | WO 97/15597 | A1 | 5/1997 |
| WO | WO 98/04728 | A1 | 2/1998 |
| WO | WO 99/46988 | | 3/1998 |
| WO | WO 98/29556 | A1 | 7/1998 |
| WO | WO 99/43839 | A1 | 9/1999 |
| WO | WO 99/46992 | A1 | 9/1999 |
| WO | WO 01/30382 | A1 | 5/2001 |
| WO | WO 03/080800 | A2 | 10/2003 |
| WO | WO 03/085087 | A3 | 10/2003 |

OTHER PUBLICATIONS von Mehren et al., 2000, Clinical Cancer Research, 6: 2219-2228.*
Horig et al., 2000, Cancer Immunol. Immunother. 49: 504-514.*
Parmiani et al., 2002, J. Natl. Cancer Inst., 94: 805-818.*
Senofi Pasteur, Ltd., U.S. Appl. No. 10/510,677B, computer printout pp. 2-5.*

(Continued)

*Primary Examiner* — Shin-Lin Chen

(74) *Attorney, Agent, or Firm* — Patrick J. Halloran; Reza Yacoob

(57) ABSTRACT

The present invention relates to a nucleic acid encoding a polypeptide and the use of the nucleic acid or polypeptide in preventing and/or treating cancer. In particular, the invention relates to improved vectors for the insertion and expression of foreign genes encoding tumor antigens for use in immunotherapeutic treatment of cancer.

12 Claims, 29 Drawing Sheets

(56) References Cited

U.S. PATENT DOCUMENTS

| | | | | |
|---|---|---|---|---|
| 5,738,852 | A | 4/1998 | Robinson et al. | |
| 5,739,026 | A | 4/1998 | Garoff et al. | |
| 5,747,028 | A | 5/1998 | Calderwood et al. | |
| 5,756,103 | A | 5/1998 | Paoletti et al. | |
| 5,762,938 | A | 6/1998 | Paoletti et al. | |
| 5,789,245 | A | 8/1998 | Dubensky et al. | |
| 5,792,462 | A | 8/1998 | Johnston et al. | |
| 5,833,975 | A | 11/1998 | Paoletti et al. | |
| 5,843,448 | A | 12/1998 | Chen et al. | |
| 5,843,723 | A | 12/1998 | Dubensky et al. | |
| 5,843,761 | A | 12/1998 | Barnett et al. | |
| 5,851,523 | A | 12/1998 | Townsend et al. | |
| 5,858,776 | A | 1/1999 | Ostrand-Rosenberg et al. | |
| 5,871,727 | A | 2/1999 | Curiel | |
| 5,919,676 | A | 7/1999 | Graham et al. | |
| 5,932,210 | A | 8/1999 | Gregory et al. | |
| 5,942,235 | A | 8/1999 | Paoletti et al. | |
| 5,965,535 | A | 10/1999 | Chaux et al. | |
| 5,990,091 | A | 11/1999 | Tartaglia et al. | |
| 5,994,132 | A | 11/1999 | Chamberlain et al. | |
| 5,994,136 | A | 11/1999 | Naldini et al. | |
| 6,001,349 | A | 12/1999 | Panicali et al. | |
| 6,013,516 | A | 1/2000 | Verma et al. | |
| 6,019,987 | A | 2/2000 | Ven Der Bruggen et al. | |
| 6,022,958 | A | 2/2000 | Barnett et al. | |
| 6,025,474 | A | 2/2000 | Van den Eynde et al. | |
| 6,045,802 | A * | 4/2000 | Schlom et al. | 424/199.1 |
| 6,057,158 | A | 5/2000 | Chamberlain et al. | |
| 6,071,716 | A | 6/2000 | Freeman et al. | |
| 6,171,855 | B1 | 1/2001 | Askari et al. | |
| 6,224,879 | B1 | 5/2001 | Sjoberg et al. | |
| 6,235,522 | B1 | 5/2001 | Kingsman et al. | |
| 6,277,633 | B1 | 8/2001 | Olsen | |
| 6,319,496 | B1 | 11/2001 | Panicali et al. | |
| 6,353,089 | B1 | 3/2002 | Van der Bruggen et al. | |
| 6,407,063 | B1 | 6/2002 | Luiten et al. | |
| 6,531,451 | B1 | 3/2003 | Chaux et al. | |
| 6,548,068 | B1 | 4/2003 | Schlom et al. | |
| 6,555,107 | B2 | 4/2003 | Poeschla et al. | |
| 6,566,093 | B1 | 5/2003 | Liljestrom et al. | |
| 6,699,475 | B1 | 3/2004 | Panicali et al. | |
| 6,756,038 | B1 | 6/2004 | Schlom et al. | |
| 6,893,869 | B2 | 5/2005 | Schlom et al. | |
| 6,969,609 | B1 | 11/2005 | Schlom et al. | |
| 7,084,239 | B1 | 8/2006 | Wang et al. | |
| 7,211,432 | B2 | 5/2007 | Schlom et al. | |
| 7,786,278 | B2 * | 8/2010 | Parrington et al. | 536/23.1 |
| 2003/0003079 | A1 | 1/2003 | Schlom et al. | |
| 2003/0082150 | A1 | 5/2003 | Boon-Falleur et al. | |
| 2003/0113919 | A1 | 6/2003 | Emtage et al. | |
| 2004/0009185 | A1 | 1/2004 | Emtage et al. | |
| 2004/0019195 | A1 | 1/2004 | Scholm et al. | |
| 2004/0091995 | A1 | 5/2004 | Schlom et al. | |
| 2007/0048860 | A1 | 3/2007 | Schlom et al. | |

OTHER PUBLICATIONS

Senofi Pasteur, Ltd., U.S. Appl. No. 10/510,677B, filed Apr. 9, 2002, computer printout pp. 2-5.*

Beauchemin, et al. Isolation and Characterization of Full-Length Functional cDNA Clones for Human Carcinoembryonic Antigen, Mol. Cell. Biol., Sep. 1987, pp. 3221-3730.

Berinstein, et al. Carcinoembryonic Antigen as a Target for Therapeutic Anticancer Vaccines: A Review. J. Clin. Oncol. 20(8): 2197-2207 (2002).

Dubensky, et al. Delivery Systems for Gene-Based Vaccines. Mol. Med. 6(9): 723-732 (2000).

Hodge, et al. Diversified Prime and Boost Protocols Using Recombinant Vaccine Virus and Recombinant Non-Replicating Avian Pox Virus to Enhance T-Cell Immunity and Antitumor Responses. Vaccine, vol. 15, issue 6/7, pp. 759-768 (1997).

Kim, et al. EMBL Accession No. BM752131 (Mar. 9, 2002).

Leitner, et al. Enhancement of Tumor-Specific Immune Response with Plasmid DNA Replicon Vectors. Cancer Res. 60: 51-55 (2000).

Marshall, et al. A phase I study of sequential vaccinations with fowlpox-CEA(6D)-Tricom (B7/ICAM/LFA3) alone . . . Abstract No. 24, 2002 ASCO Annual Meeting.

Marshall, J. Carcinoembryonic Antigen-Based Vaccines. Semin. Oncol. (suppl. 8): 30-36 (2003).

Pardoll, D.M. Cancer vaccines. *Nat.Med*. 4:525-531 (1998).

Parmiani, et al. Cancer Immunotherapy with Peptide-Based Vaccines: What Have We Achieved? Where Are We Going? J. Natl. Cancer Inst. 94: 805-818 (2002).

Van Der Burg, et al. Induction of p53-Specific Immune Responses in Colorectal Cancer Patients Receiving a Recombinant ALVAC-p53 Candidate Vaccine. Clin. Cancer Res. 8: 1019-1027 (2002).

Bei, et al. 1994, *J. Immunotherapy with Emphasis on Tumor Immunology*. 16(4): 275-282.

Boon, et al. 1994, *Ann. Rev. Immunol*. 12:337-365.

Chamberlain, 1996. Cancer Res. 56: 2832-2836.

Conry, et al. 1999. *Clin. Cancer Res*. 5: 2330-2337.

GenBank Accession No, X60958 (Jul. 18. 1991).

GenBank Accession No. M27533 (Sep. 8, 1989).

GenBank Accession No. X52264 (Aug. 28, 1989).

GenBank Accession No. J03132 (Mar. 25, 1988).

GenBank Accession No. X53526 (Jun. 18, 1990).

GenBank Accession No. Y00636 (Aug. 31, 1987).

GenBank Accession No. U02567 (Oct. 18, 1993).

GenBank Accession No. U03397 (Nov. 10. 1993).

Hodge, et al. 1995, *Cancer Res*. 55: 3598-3603.

Hodge, et al. 1999. *Cancer Res*. 59(22): 5800-5807.

Horig, et al. 2000. *Cancer Immunol. Inmumother*. 49: 504-514.

Huarte, et al, 2002. *Clin. Cancer Res*. 8(7): 2336-2344.

Marshall, et al. 2000. *J. Clinical Oncol*. 18: 3964-3973.

Moingeon, P. 2001, *Vaccine*. 19 (11-12): 1305-1326.

Oertli, et al. 2002. *Human Gene Therapy*. 13: 569-575.

Salazar, et al. 2000. *Int. J. of Cancer*. 85(6): 829-838.

Tartaglia, et al. 1992. *Virology*. 188: 217-232.

Tartaglia, et al. 1993. *J. Virol*. 67: 2370-2375.

Tartaglia, et al. 2001. *Vaccine*. 19: 2571-2575.

Terskikh, et al. 1993. *Mol. Immunol*. 30(10): 921-927.

Von Mehren, et al. 2000. *Clin. Cancer Res*. 6: 2219-2228.

Von Mehren, et al. 2001. *Clin. Cancer Res*. 7: 1181-1191.

Zaremba, et al. 1997. *Cancer Research*. 57:4570-4577.

* cited by examiner

FIGURE 1
A.
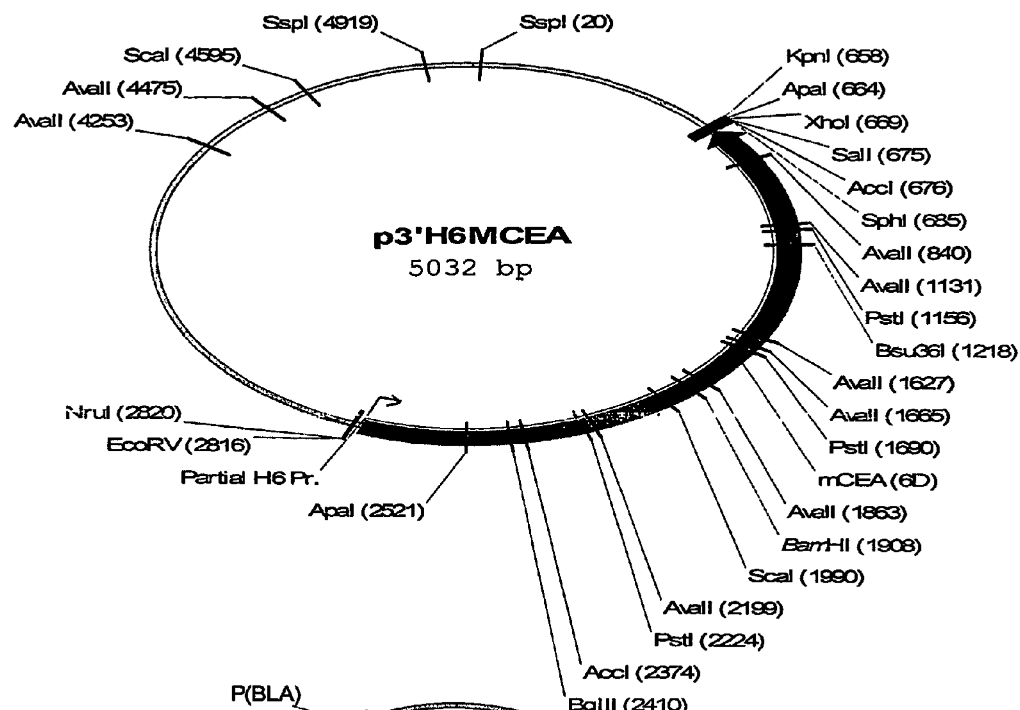
B.
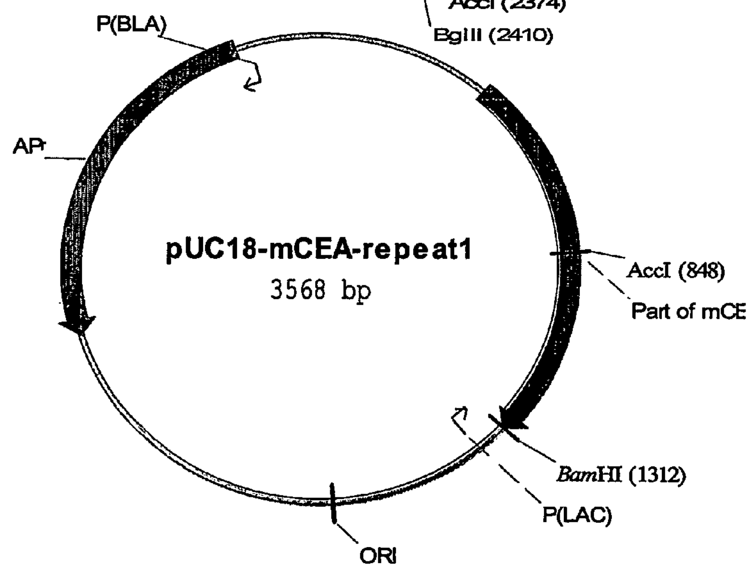

pUC18 mCEA modified repeat 2 (gsoe)

pUC18 mCEA modified repeat 2 gsoe minus Ala

FIGURE 9A

```
                     1                                                    50
mCEA(6D)             ATGGAGTCTC CCTCGGCCCC TCCCCACAGA TGGTGCATCC CCTGGCAGAG
mCEA(6D,1st&2nd)     ATGGAGTCTC CCTCGGCCCC TCCCCACAGA TGGTGCATCC CCTGGCAGAG

                     51                                                  100
mCEA(6D)             GCTCCTGCTC ACAGCCTCAC TTCTAACCTT CTGGAACCCG CCCACCACTG
mCEA(6D,1st&2nd)     GCTCCTGCTC ACAGCCTCAC TTCTAACCTT CTGGAACCCG CCCACCACTG

                     101                                                 150
mCEA(6D)             CCAAGCTCAC TATTGAATCC ACGCCGTTCA ATGTCGCAGA GGGGAAGGAG
mCEA(6D,1st&2nd)     CCAAGCTCAC TATTGAATCC ACGCCGTTCA ATGTCGCAGA GGGGAAGGAG

                     151                                                 200
mCEA(6D)             GTGCTTCTAC TTGTCCACAA TCTGCCCCAG CATCTTTTTG GCTACAGCTG
mCEA(6D,1st&2nd)     GTGCTTCTAC TTGTCCACAA TCTGCCCCAG CATCTTTTTG GCTACAGCTG

                     201                                                 250
mCEA(6D)             GTACAAAGGT GAAAGAGTGG ATGGCAACCG TCAAATTATA GGATATGTAA
mCEA(6D,1st&2nd)     GTACAAAGGT GAAAGAGTGG ATGGCAACCG TCAAATTATA GGATATGTAA

                     251                                                 300
mCEA(6D)             TAGGAACTCA ACAAGCTACC CCAGGGCCCG CATACAGTGG TCGAGAGATA
mCEA(6D,1st&2nd)     TAGGAACTCA ACAAGCTACC CCAGGGCCCG CATACAGTGG TCGAGAGATA

                     301                                                 350
mCEA(6D)             ATATACCCCA ATGCATCCCT GCTGATCCAG AACATCATCC AGAATGACAC
mCEA(6D,1st&2nd)     ATATACCCCA ATGCATCCCT GCTGATCCAG AACATCATCC AGAATGACAC

                     351                                                 400
mCEA(6D)             AGGATTCTAC ACCCTACACG TCATAAAGTC AGATCTTGTG AATGAAGAAG
mCEA(6D,1st&2nd)     AGGATTCTAC ACCCTACACG TCATAAAGTC AGATCTTGTG AATGAAGAAG

                     401                                                 450
mCEA(6D)             CAACTGGCCA GTTCCGGGTA TACCCGGAGC TGCCCAAGCC CTCCATCTCC
mCEA(6D,1st&2nd)     CAACTGGCCA GTTCCGGGTA TACCCGGAAC TCCCTAAGCC TTCTATTAGC

                     451                                                 500
mCEA(6D)             AGCAACAACT CCAAACCCGT GGAGGACAAG GATGCTGTGG CCTTCACCTG
mCEA(6D,1st&2nd)     TCCAATAATA GTAAGCCTGT CGAAGACAAA GATGCCGTCG CTTTTACATG

                     501                                                 550
mCEA(6D)             TGAACCTGAG ACTCAGGACG CAACCTACCT GTGGTGGGTA AACAATCAGA
mCEA(6D,1st&2nd)     CGAGCCCGAA ACTCAAGACG CAACATATCT CTGGTGGGTG AACAACCAGT

                     551                                                 600
mCEA(6D)             GCCTCCCGGT CAGTCCCAGG CTGCAGCTGT CCAATGGCAA CAGGACCCTC
mCEA(6D,1st&2nd)     CCCTGCCTGT GTCCCCTAGA CTCCAACTCA GCAACGGAAA TAGAACTCTG

                     601                                                 650
mCEA(6D)             ACTCTATTCA ATGTCACAAG AAATGACACA GCAAGCTACA AATGTGAAAC
mCEA(6D,1st&2nd)     ACCCTGTTTA ACGTGACCAG GAACGACACA GCAAGCTACA AATGCGAAAC
```

FIGURE 9B

```
                     651                                                  700
          mCEA(6D)   CCAGAACCCA GTGAGTGCCA GGCGCAGTGA TTCAGTCATC CTGAATGTCC
mCEA(6D,1st&2nd)     CCAAAATCCA GTCAGCGCCA GGAGGTCTGA TTCAGTGATT CTCAACGTGC

                     701                                                  750
          mCEA(6D)   TCTATGGCCC GGATGCCCCC ACCATTTCCC CTCTAAACAC ATCTTACAGA
mCEA(6D,1st&2nd)     TTTACGGACC CGATGCTCCT ACAATCAGCC CTCTAAACAC AAGCTATAGA

                     751                                                  800
          mCEA(6D)   TCAGGGGAAA ATCTGAACCT CTCCTGCCAC GCAGCCTCTA ACCCACCTGC
mCEA(6D,1st&2nd)     TCAGGGGAAA ATCTGAATCT GAGCTGTCAT GCCGCTAGCA ATCCTCCCGC

                     801                                                  850
          mCEA(6D)   ACAGTACTCT TGGTTTGTCA ATGGGACTTT CCAGCAATCC ACCCAAGAGC
mCEA(6D,1st&2nd)     CCAATACAGC TGGTTTGTCA ATGGCACTTT CCAACAGTCC ACCCAGGAAC

                     851                                                  900
          mCEA(6D)   TCTTTATCCC CAACATCACT GTGAATAATA GTGGATCCTA TACGTGCCAA
mCEA(6D,1st&2nd)     TGTTCATTCC CAATATTACC GTGAACAATA GTGGATCCTA CACGTGCCAA

                     901                                                  950
          mCEA(6D)   GCCCATAACT CAGACACTGG CCTCAATAGG ACCACAGTCA CGACGATCAC
mCEA(6D,1st&2nd)     GCTCACAATA GCGACACCGG ACTCAACCGC ACAACCGTGA CGACGATTAC

                     951                                                 1000
          mCEA(6D)   AGTCTATGAG CCACCCAAAC CCTTCATCAC CAGCAACAAC TCCAACCCCG
mCEA(6D,1st&2nd)     CGTGTATGAG CCACCAAAAC CATTCATAAC TAGTAACAAT TCTAACCCAG

                     1001                                                1050
          mCEA(6D)   TGGAGGATGA GGATGCTGTA GCCTTAACCT GTGAACCTGA GATTCAGAAC
mCEA(6D,1st&2nd)     TTGAGGATGA GGACGCAGTT GCATTAACTT GTGAGCCAGA GATTCAAAAT

                     1051                                                1100
          mCEA(6D)   ACAACCTACC TGTGGTGGGT AAATAATCAG AGCCTCCCGG TCAGTCCCAG
mCEA(6D,1st&2nd)     ACCACTTATT TATGGTGGGT CAATAACCAA AGTTTGCCGG TTAGCCCACG

                     1101                                                1150
          mCEA(6D)   GCTGCAGCTG TCCAATGACA ACAGGACCCT CACTCTACTC AGTGTCACAA
mCEA(6D,1st&2nd)     CTTGCAGTTG TCTAATGATA ACCGCACATT GACACTCCTG TCCGTTACTC

                     1151                                                1200
          mCEA(6D)   GGAATGATGT AGGACCCTAT GAGTGTGGAA TCCAGAACGA ATTAAGTGTT
mCEA(6D,1st&2nd)     GCAATGATGT AGGACCTTAT GAGTGTGGCA TTCAGAATGA ATTATCCGTT

                     1201                                                1250
          mCEA(6D)   GACCACAGCG ACCCAGTCAT CCTGAATGTC CTCTATGGCC CAGACGACCC
mCEA(6D,1st&2nd)     GATCACTCCG ACCCTGTTAT CCTTAATGTT TTGTATGGCC CAGACGACCC

                     1251                                                1300
          mCEA(6D)   CACCATTTCC CCCTCATACA CCTATTACCG TCCAGGGGTG AACCTCAGCC
mCEA(6D,1st&2nd)     AACTATATCT CCATCATACA CCTACTACCG TCCCGGCGTG AACTTGAGCC
```

FIGURE 9C

```
                    1301                                                    1350
         mCEA(6D)   TCTCCTGCCA TGCAGCCTCT AACCCACCTG CACAGTATTC TTGGCTGATT
mCEA(6D,1st&2nd)    TTTCTTGCCA TGCAGCATCC AACCCCCCTG CACAGTACTC CTGGCTGATT

                    1351                                                    1400
         mCEA(6D)   GATGGGAACA TCCAGCAACA CACACAAGAG CTCTTTATCT CCAACATCAC
mCEA(6D,1st&2nd)    GATGGAAACA TTCAGCAGCA TACTCAAGAG TTATTTATAA GCAACATAAC

                    1401                                                    1450
         mCEA(6D)   TGAGAAGAAC AGCGGACTCT ATACCTGCCA GGCCAATAAC TCAGCCAGTG
mCEA(6D,1st&2nd)    TGAGAAGAAC AGCGGACTCT ATACTTGCCA GGCCAATAAC TCAGCCAGTG

                    1451                                                    1500
         mCEA(6D)   GCCACAGCAG GACTACAGTC AAGACAATCA CAGTCTCTGC GGAGCTGCCC
mCEA(6D,1st&2nd)    GTCACAGCAG GACTACAGTT AAAACAATAA CTGTTTCCGC GGAGCTGCCC

                    1501                                                    1550
         mCEA(6D)   AAGCCCTCCA TCTCCAGCAA CAACTCCAAA CCCGTGGAGG ACAAGGATGC
mCEA(6D,1st&2nd)    AAGCCCTCCA TCTCCAGCAA CAACTCCAAA CCCGTGGAGG ACAAGGATGC

                    1551                                                    1600
         mCEA(6D)   TGTGGCCTTC ACCTGTGAAC CTGAGGCTCA GAACACAACC TACCTGTGGT
mCEA(6D,1st&2nd)    TGTGGCCTTC ACCTGTGAAC CTGAGGCTCA GAACACAACC TACCTGTGGT

                    1601                                                    1650
         mCEA(6D)   GGGTAAATGG TCAGAGCCTC CCAGTCAGTC CCAGGCTGCA GCTGTCCAAT
mCEA(6D,1st&2nd)    GGGTAAATGG TCAGAGCCTC CCAGTCAGTC CCAGGCTGCA GCTGTCCAAT

                    1651                                                    1700
         mCEA(6D)   GGCAACAGGA CCCTCACTCT ATTCAATGTC ACAAGAAATG ACGCAAGAGC
mCEA(6D,1st&2nd)    GGCAACAGGA CCCTCACTCT ATTCAATGTC ACAAGAAATG ACGCAAGAGC

                    1701                                                    1750
         mCEA(6D)   CTATGTATGT GGAATCCAGA ACTCAGTGAG TGCAAACCGC AGTGACCCAG
mCEA(6D,1st&2nd)    CTATGTATGT GGAATCCAGA ACTCAGTGAG TGCAAACCGC AGTGACCCAG

                    1751                                                    1800
         mCEA(6D)   TCACCCTGGA TGTCCTCTAT GGGCCGGACA CCCCCATCAT TTCCCCCCCA
mCEA(6D,1st&2nd)    TCACCCTGGA TGTCCTCTAT GGGCCGGACA CCCCCATCAT TTCCCCCCCA

                    1801                                                    1850
         mCEA(6D)   GACTCGTCTT ACCTTTCGGG AGCGGACCTC AACCTCTCCT GCCACTCGGC
mCEA(6D,1st&2nd)    GACTCGTCTT ACCTTTCGGG AGCGGACCTC AACCTCTCCT GCCACTCGGC

                    1851                                                    1900
         mCEA(6D)   CTCTAACCCA TCCCCGCAGT ATTCTTGGCG TATCAATGGG ATACCGCAGC
mCEA(6D,1st&2nd)    CTCTAACCCA TCCCCGCAGT ATTCTTGGCG TATCAATGGG ATACCGCAGC

                    1901                                                    1950
         mCEA(6D)   AACACACACA AGTTCTCTTT ATCGCCAAAA TCACGCCAAA TAATAACGGG
mCEA(6D,1st&2nd)    AACACACACA AGTTCTCTTT ATCGCCAAAA TCACGCCAAA TAATAACGGG
```

FIGURE 9D

```
                    1951                                                  2000
         mCEA(6D)   ACCTATGCCT GTTTTGTCTC TAACTTGGCT ACTGGCCGCA ATAATTCCAT
mCEA(6D,1st&2nd)   ACCTATGCCT GTTTTGTCTC TAACTTGGCT ACTGGCCGCA ATAATTCCAT

                    2001                                                  2050
         mCEA(6D)   AGTCAAGAGC ATCACAGTCT CTGCATCTGG AACTTCTCCT GGTCTCTCAG
mCEA(6D,1st&2nd)   AGTCAAGAGC ATCACAGTCT CTGCATCTGG AACTTCTCCT GGTCTCTCAG

                    2051                                                  2100
         mCEA(6D)   CTGGGGCCAC TGTCGGCATC ATGATTGGAG TGCTGGTTGG GGTTGCTCTG
mCEA(6D,1st&2nd)   CTGGGGCCAC TGTCGGCATC ATGATTGGAG TGCTGGTTGG GGTTGCTCTG

                    2101
         mCEA(6D)   ATATAG
mCEA(6D,1st&2nd)   ATATAG
```

FIGURE 12A

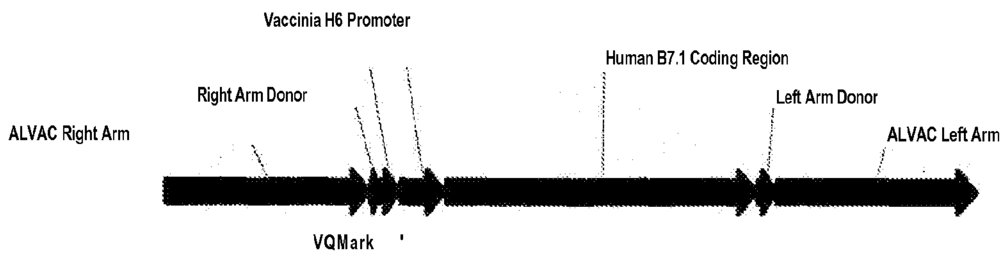

```
          ALVAC Right Arm Flanking Sequence
     ______________________________________________________
  1  TTAGATTGTG TTATTCATTA CATAGACGCT GCTAAATCTA CTATCGATTT
     AATCTAACAC AATAAGTAAT GTATCTGCGA CGATTTAGAT GATAGCTAAA

          ALVAC Right Arm Flanking Sequence
     ______________________________________________________
 51  AGAGATAGTA TCTCTACTAC CCACAAAAAG AACTAAAGAC GCCATAGTGT
     TCTCTATCAT AGAGATGATG GGTGTTTTTC TTGATTTCTG CGGTATCACA

          ALVAC Right Arm Flanking Sequence
     ______________________________________________________
101  ACTGGCCTAT AATAAAAGAC GCGTTGATAA GAGCTGTTCT GGAACGTGGT
     TGACCGGATA TTATTTTCTG CGCAACTATT CTCGACAAGA CCTTGCACCA

          ALVAC Right Arm Flanking Sequence
     ______________________________________________________
151  GTTAAACTTA GAATACTACT AGGTTATTGG AAAAAGACCG ATATTATCTC
     CAATTTGAAT CTTATGATGA TCCAATAACC TTTTTCTGGC TATAATAGAG

          ALVAC Right Arm Flanking Sequence
     ______________________________________________________
201  TAAAGCTTCT ATCAAAAGTC TTAATGAGTT AGGTGTAGAT AGTATAGATA
     ATTTCGAAGA TAGTTTTCAG AATTACTCAA TCCACATCTA TCATATCTAT

          ALVAC Right Arm Flanking Sequence
     ______________________________________________________
251  TTACTACAAA GGTATTCATA TTTCCTATCA ATTCTAAAGT AGATGATATT
     AATGATGTTT CCATAAGTAT AAAGGATAGT TAAGATTTCA TCTACTATAA

          ALVAC Right Arm Flanking Sequence
     ______________________________________________________
301  AATAACTCAA AGATGATGAT AGTAGATAAT AGATACGCTC ATATAATGAC
     TTATTGAGTT TCTACTACTA TCATCTATTA TCTATGCGAG TATATTACTG

          ALVAC Right Arm Flanking Sequence
     ______________________________________________________
351  TGCAAATTTG GACGGTTCAC ATTTTAATCA TCACGCGTTC ATAAGTCTCA
     ACGTTTAAAC CTGCCAAGTG TAAAATTAGT AGTGCGCAAG TATTCAAAGT
```

FIGURE 12B

```
           ALVAC Right Arm Flanking Sequence
       _____________________________________________
401  ACTGCATAGA TCAAAATCTC ACTAAAAAGA TAGCCGATGT ATTTGAGAGA
      TGACGTATCT AGTTTTAGAG TGATTTTTCT ATCGGCTACA TAAACTCTCT

           ALVAC Right Arm Flanking Sequence
       _____________________________________________
451   GATTGGACAT CTAACTACGC TAAAGAAATT ACAGTTATAA ATAATACATA
      CTAACCTGTA GATTGATGCG ATTTCTTTAA TGTCAATATT TATTATGTAT

           ALVAC Right Arm Flanking Sequence
       _____________________________________________
501   ATGGATTTTG TTATCATCAG TTATATTTAA CATAAGTACA ATAAAAAGTA
      TACCTAAAAC AATAGTAGTC AATATAAATT GTATTCATGT TATTTTTCAT

                                      Right Arm Donor Plasmid

      ALVAC Right Arm Flanking Sequence
      _____________________________
551   TTAAATAAAA ATACTTACTT ACGAAAAAAT GACTAATTAG CTATAAAAAC
      AATTTATTTT TATGAATGAA TGCTTTTTTA CTGATTAATC GATATTTTTG

                         VQ Mark

      Right Arm Donor Plasmid

601   CCGGGTTAAT TAATTAGTTA TTAGACAAGG TGAAAACGAA ACTATTTGTA
      GGCCCAATTA ATTAATCAAT AATCTGTTCC ACTTTTGCTT TGATAAACAT

          VQ Mark

                         Vaccinia H6 Promoter
                     ______________________________
651   GCTTAATTAA TTAGAGCTTC TTTATTCTAT ACTTAAAAAG TGAAAATAAA
      CGAATTAATT AATCTCGAAG AAATAAGATA TGAATTTTTC ACTTTTATTT

                  Vaccinia H6 Promoter
      _____________________________________________
701   TACAAAGGTT CTTGAGGGTT GTGTTAAATT GAAAGCGAGA AATAATCATA
      ATGTTTCCAA GAACTCCCAA CACAATTTAA CTTTCGCTCT TTATTAGTAT

                                          Human B7.1 Coding Region

              Vaccinia H6 Promoter
      _____________________________________
751   AATTATTTCA TTATCGCGAT ATCCGTTAAG TTTGTATCGT AATGGGCCAC
      TTAATAAAGT AATAGCGCTA TAGGCAATTC AAACATAGCA TTACCCGGTG

                 Human B7.1 Coding Region
      _____________________________________________
801   ACACGGAGGC AGGGAACATC ACCATCCAAG TGTCCATACC TCAATTTCTT
      TGTGCCTCCG TCCCTTGTAG TGGTAGGTTC ACAGGTATGG AGTTAAAGAA

                 Human B7.1 Coding Region
      _____________________________________________
851   TCAGCTCTTG GTGCTGGCTG GTCTTTCTCA CTTCTGTTCA GGTGTTATCC
      AGTCGAGAAC CACGACCGAC CAGAAAGAGT GAAGACAAGT CCACAATAGG
```

FIGURE 12C

```
                  Human B7.1 Coding Region
       ---------------------------------------------------
 901   ACGTGACCAA GGAAGTGAAA GAAGTGGCAA CGCTGTCCTG TGGTCACAAT
       TGCACTGGTT CCTTCACTTT CTTCACCGTT GCGACAGGAC ACCAGTGTTA

                  Human B7.1 Coding Region
       ---------------------------------------------------
 951   GTTTCTGTTG AAGAGCTGGC ACAAACTCGC ATCTACTGGC AAAAGGAGAA
       CAAAGACAAC TTCTCGACCG TGTTTGAGCG TAGATGACCG TTTTCCTCTT

                  Human B7.1 Coding Region
       ---------------------------------------------------
1001   GAAAATGGTG CTGACTATGA TGTCTGGAGA CATGAATATA TGGCCCGAGT
       CTTTTACCAC GACTGATACT ACAGACCTCT GTACTTATAT ACCGGGCTCA

                  Human B7.1 Coding Region
       ---------------------------------------------------
1051   ACAAGAACCG GACCATCTTT GATATCACTA ATAACCTCTC CATTGTGATC
       TGTTCTTGGC CTGGTAGAAA CTATAGTGAT TATTGGAGAG GTAACACTAG

                  Human B7.1 Coding Region
       ---------------------------------------------------
1101   CTGGCTCTGC GCCCATCTGA CGAGGGCACA TACGAGTGTG TTGTTCTGAA
       GACCGAGACG CGGGTAGACT GCTCCCGTGT ATGCTCACAC AACAAGACTT

                  Human B7.1 Coding Region
       ---------------------------------------------------
1151   GTATGAAAAA GACGCTTTCA AGCGGGAACA CCTGGCTGAA GTGACGTTAT
       CATACTTTTT CTGCGAAAGT TCGCCCTTGT GGACCGACTT CACTGCAATA

                  Human B7.1 Coding Region
       ---------------------------------------------------
1201   CAGTCAAAGC TGACTTCCCT ACACCTAGTA TATCTGACTT TGAAATTCCA
       GTCAGTTTCG ACTGAAGGGA TGTGGATCAT ATAGACTGAA ACTTTAAGGT

                  Human B7.1 Coding Region
       ---------------------------------------------------
1251   ACTTCTAATA TTAGAAGGAT AATTTGCTCA ACCTCTGGAG GTTTTCCAGA
       TGAAGATTAT AATCTTCCTA TTAAACGAGT TGGAGACCTC CAAAAGGTCT

                  Human B7.1 Coding Region
       ---------------------------------------------------
1301   GCCTCACCTC TCCTGGTTGG AAAATGGAGA AGAATTAAAT GCCATCAACA
       CGGAGTGGAG AGGACCAACC TTTTACCTCT TCTTAATTTA CGGTAGTTGT

                  Human B7.1 Coding Region
       ---------------------------------------------------
1351   CAACAGTTTC CCAAGATCCT GAAACTGAGC TCTATGCTGT TAGCAGCAAA
       GTTGTCAAAG GGTTCTAGGA CTTTGACTCG AGATACGACA ATCGTCGTTT

                  Human B7.1 Coding Region
       ---------------------------------------------------
1401   CTGGATTTCA ATATGACAAC CAACCACAGC TTCATGTGTC TCATCAAGTA
       GACCTAAAGT TATACTGTTG GTTGGTGTCG AAGTACACAG AGTAGTTCAT
```

FIGURE 12D

```
                    Human B7.1 Coding Region
          ____________________________________________________
1451      TGGACATTTA AGAGTGAATC AGACCTTCAA CTGGAATACA ACCAAGCAAG
          ACCTGTAAAT TCTCACTTAG TCTGGAAGTT GACCTTATGT TGGTTCGTTC

                    Human B7.1 Coding Region
          ____________________________________________________
1501      AGCATTTTCC TGATAACCTG CTCCCATCCT GGGCCATTAC CTTAATCTCA
          TCGTAAAAGG ACTATTGGAC GAGGGTAGGA CCCGGTAATG GAATTAGAGT

                    Human B7.1 Coding Region
          ____________________________________________________
1551      GTAAATGGAA TTTTCGTGAT ATGCTGCCTG ACCTACTGCT TTGCCCCACG
          CATTTACCTT AAAAGCACTA TACGACGGAC TGGATGACGA AACGGGGTGC

                    Human B7.1 Coding Region
          ____________________________________________________
1601      CTGCAGAGAG AGAAGGAGGA ATGAGAGATT GAGAAGGGAA AGTGTACGTC
          GACGTCTCTC TCTTCCTCCT TACTCTCTAA CTCTTCCCTT TCACATGCAG

                         Left Arm Donor Plasmid

          Human B7.1 Coding Region
          ________
1651      CTGTATAATT TTTATCTCGA GCCCGGGAAG CTTGAATTCT TTTTATTGAT
          GACATATTAA AAATAGAGCT CGGGCCCTTC GAACTTAAGA AAAATAACTA

                       ALVAC Left Arm Flanking Sequence

          Left Arm Donor Plasmid
          _____________
1701      TAACTAGTCA AATGAGTATA TATAATTGAA AAAGTAAAAT ATAAATCATA
          ATTGATCAGT TTACTCATAT ATATTAACTT TTTCATTTTA TATTTAGTAT

                 ALVAC Left Arm Flanking Sequence
          ____________________________________________________
1751      TAATAATGAA ACGAAATATC AGTAATAGAC AGGAACTGGC AGATTCTTCT
          ATTATTACTT TGCTTTATAG TCATTATCTG TCCTTGACCG TCTAAGAAGA

                 ALVAC Left Arm Flanking Sequence
          ____________________________________________________
1801      TCTAATGAAG TAAGTACTGC TAAATCTCCA AAATTAGATA AAAATGATAC
          AGATTACTTC ATTCATGACG ATTTAGAGGT TTTAATCTAT TTTTACTATG

                 ALVAC Left Arm Flanking Sequence
          ____________________________________________________
1851      AGCAAATACA GCTTCATTCA ACGAATTACC TTTTAATTTT TTCAGACACA
          TCGTTTATGT CGAAGTAAGT TGCTTAATGG AAAATTAAAA AAGTCTGTGT

                 ALVAC Left Arm Flanking Sequence
          ____________________________________________________
1901      CCTTATTACA AACTAACTAA GTCAGATGAT GAGAAAGTAA ATATAAATTT
          GGAATAATGT TTGATTGATT CAGTCTACTA CTCTTTCATT TATATTTAAA
```

FIGURE 12E

```
            ALVAC Left Arm Flanking Sequence
       ____________________________________________________
1951   AACTTATGGG TATAATATAA TAAAGATTCA TGATATTAAT AATTTACTTA
       TTGAATACCC ATATTATATT ATTTCTAAGT ACTATAATTA TTAAATGAAT

            ALVAC Left Arm Flanking Sequence
       ____________________________________________________
2001   ACGATGTTAA TAGACTTATT CCATCAACCC CTTCAAACCT TTCTGGATAT
       TGCTACAATT ATCTGAATAA GGTAGTTGGG GAAGTTTGGA AAGACCTATA

            ALVAC Left Arm Flanking Sequence
       ____________________________________________________
2051   TATAAAATAC CAGTTAATGA TATTAAAATA GATTGTTTAA GAGATGTAAA
       ATATTTTATG GTCAATTACT ATAATTTTAT CTAACAAATT CTCTACATTT

            ALVAC Left Arm Flanking Sequence
       ____________________________________________________
2101   TAATTATTTG GAGGTAAAGG ATATAAAATT AGTCTATCTT TCACATGGAA
       ATTAATAAAC CTCCATTTCC TATATTTTAA TCAGATAGAA AGTGTACCTT

            ALVAC Left Arm Flanking Sequence
       ____________________________________________________
2151   ATGAATTACC TAATATTAAT AATTATGATA GGAATTTTTT AGGATTTACA
       TACTTAATGG ATTATAATTA TTAATACTAT CCTTAAAAAA TCCTAAATGT

            ALVAC Left Arm Flanking Sequence
       ____________________________________________________
2201   GCTGTTATAT GTATCAACAA TACAGGCAGA TCTATGGTTA TGGTAAAACA
       CGACAATATA CATAGTTGTT ATGTCCGTCT AGATACCAAT ACCATTTTGT

       ALVAC Left Arm Flanking Sequence
       ____________________
2251   CTGTAACGGG AAGCAGCAT
       GACATTGCCC TTCGTCGTA
```

FIGURE 13A

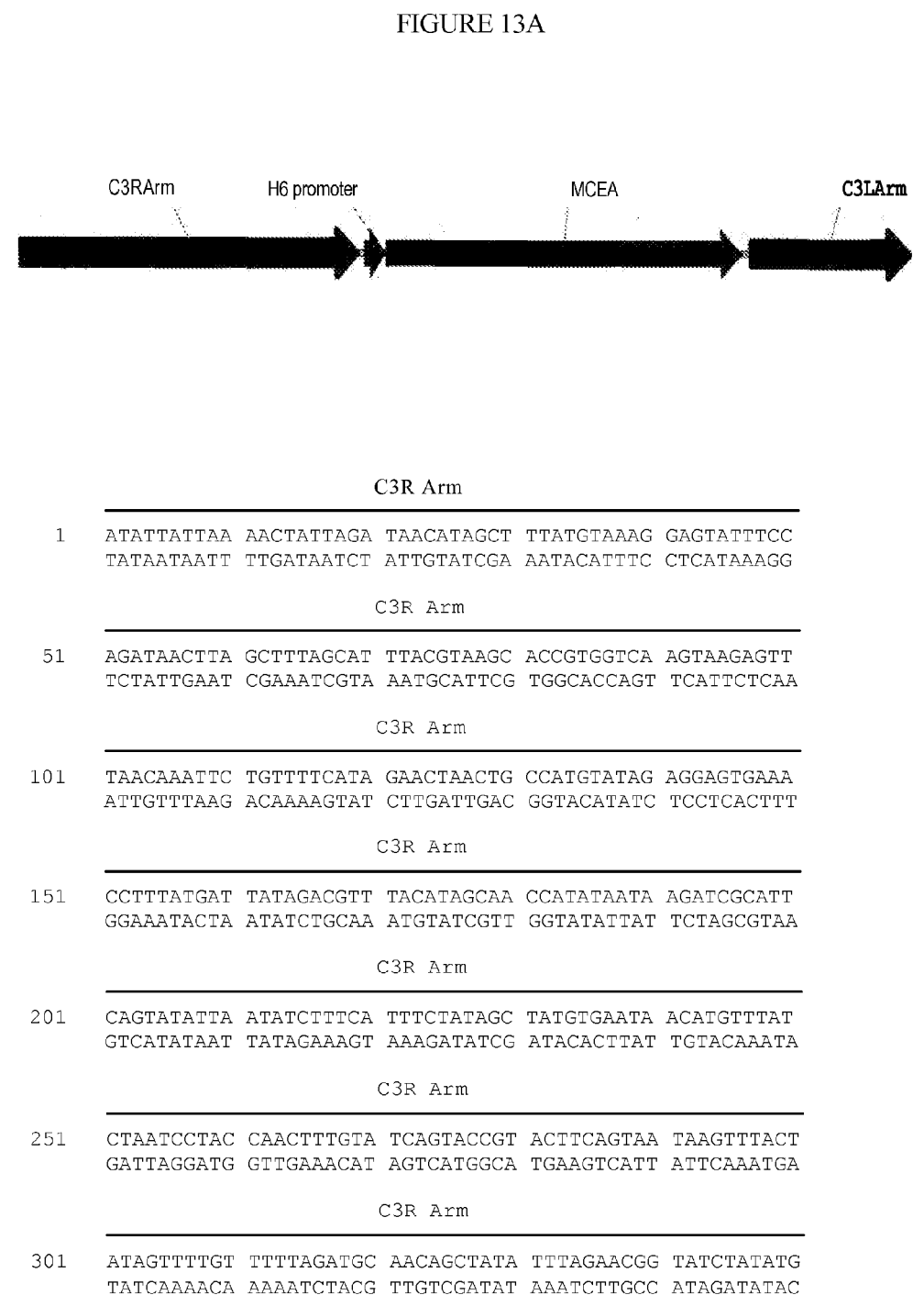

C3R Arm

```
1    ATATTATTAA AACTATTAGA TAACATAGCT TTATGTAAAG GAGTATTTCC
     TATAATAATT TTGATAATCT ATTGTATCGA AATACATTTC CTCATAAAGG
```

C3R Arm

```
51   AGATAACTTA GCTTTAGCAT TTACGTAAGC ACCGTGGTCA AGTAAGAGTT
     TCTATTGAAT CGAAATCGTA AATGCATTCG TGGCACCAGT TCATTCTCAA
```

C3R Arm

```
101  TAACAAATTC TGTTTTCATA GAACTAACTG CCATGTATAG AGGAGTGAAA
     ATTGTTTAAG ACAAAAGTAT CTTGATTGAC GGTACATATC TCCTCACTTT
```

C3R Arm

```
151  CCTTTATGAT TATAGACGTT TACATAGCAA CCATATAATA AGATCGCATT
     GGAAATACTA ATATCTGCAA ATGTATCGTT GGTATATTAT TCTAGCGTAA
```

C3R Arm

```
201  CAGTATATTA ATATCTTTCA TTTCTATAGC TATGTGAATA ACATGTTTAT
     GTCATATAAT TATAGAAAGT AAAGATATCG ATACACTTAT TGTACAAATA
```

C3R Arm

```
251  CTAATCCTAC CAACTTTGTA TCAGTACCGT ACTTCAGTAA TAAGTTTACT
     GATTAGGATG GTTGAAACAT AGTCATGGCA TGAAGTCATT ATTCAAATGA
```

C3R Arm

```
301  ATAGTTTTGT TTTTAGATGC AACAGCTATA TTTAGAACGG TATCTATATG
     TATCAAAACA AAAATCTACG TTGTCGATAT AAATCTTGCC ATAGATATAC
```

FIGURE 13B

```
                         C3R Arm
     ____________________________________________________
351  ATTATTAACC ACATTAACAT TAGATCCTCT TTCTAAAAGT GTCTTTGTTG
     TAATAATTGG TGTAATTGTA ATCTAGGAGA AAGATTTTCA CAGAAACAAC
                         C3R Arm
     ____________________________________________________
401  TTTCGATATC GTTACGTGAA ACAGCGTAAT GTAAGGGACT GCCCATACAG
     AAAGCTATAG CAATGCACTT TGTCGCATTA CATTCCCTGA CGGGTATGTC

                         C3R Arm
     ____________________________________________________
451  TCATCTATTA CGTTTATATG AGCTCCTAGA TTTAACAGAA GTGCTGTTAC
     AGTAGATAAT GCAAATATAG TCGAGGATCT AAATTGTCTT CACGACAATG

                         C3R Arm
     ____________________________________________________
501  ATCTTTTCTT CTATTAATTA CCGAATGATG TAATGGGGTT TTACCTAAAT
     TAGAAAAGAA GATAATTAAT GGCTTACTAC ATTACCCCAA AATGGATTTA

                         C3R Arm
     ____________________________________________________
551  CATCTTGTTC GTTTATAGGC ACTCCGTGAT TTATAAGTAA CGCTATTATA
     GTAGAACAAG CAAATATCCG TGAGGCACTA AATATTCATT GCGATAATAT

                         C3R Arm
     ____________________________________________________
601  TCGTAACTAC AATTATTTTT AAGTGCCTTT ATGAGATACT GTTTATGCAA
     AGCATTGATG TTAATAAAAA TTCACGGAAA TACTCTATGA CAAATACGTT

                         C3R Arm
     ____________________________________________________
651  AAATAAACTT TTATCTATTT TAATACTATT ATCTAACAAT ATCCTAATTA
     TTTATTTGAA AATAGATAAA ATTATGATAA TAGATTGTTA TAGGATTAAT

                         C3R Arm
     ____________________________________________________
701  AATCTATATT CTTATACTTT ATAGCGTAAT GTAACGGAGT TTCAAAATTT
     TTAGATATAA GAATATGAAA TATCGCATTA CATTGCCTCA AAGTTTTAAA

                         C3R Arm
     ____________________________________________________
751  CTAGTTTGTA TATTAAGATC AATATTAAAA TCTATAAATA TTTTATACAT
     GATCAAACAT ATAATTCTAG TTATAATTTT AGATATTTAT AAAATATGTA

                         C3R Arm
     ____________________________________________________
801  ATCATCAGAT ATCTTATCAT ACAGTACATC GTAATAATTT AGAAAGAATC
     TAGTAGTCTA TAGAATAGTA TGTCATGTAG CATTATTAAA TCTTTCTTAG

                         C3R Arm
     ____________________________________________________
851  TATTACAATT AACACCTTTT TTTAATAAAT ATCTAGTTAA TGACTTATTG
     ATAATGTTAA TTGTGGAAAA AAATTATTTA TAGATCAATT ACTGAATAAC
```

FIGURE 13C

C3R Arm

```
901   TTTCTATATA CAGAAATATA TAACGGACTA TTTCCAGAAT GTATCTGTTC
      AAAGATATAT GTCTTTATAT ATTGCCTGAT AAAGGTCTTA CATAGACAAG
```

C3R Arm

```
951   TATGTCAGCG CCAGAATCTA TTAGTAGTTT AGCAATTTCT GTATTATCTA
      ATACAGTCGC GGTCTTAGAT AATCATCAAA TCGTTAAAGA CATAATAGAT
```

C3R Arm

```
1001  AACTAGCAGC TTTATGAAGA GGAGGATTTT TACATTTTAA AATATCGGCA
      TTGATCGTCG AAATACTTCT CCTCCTAAAA ATGTAAAATT TTATAGCCGT
```

C3R Arm

```
1051  CCGTGTTCTA GTAATAATTT TACCATTTCT ATATCAGAAA TACTTACGGC
      GGCACAAGAT CATTATTAAA ATGGTAAAGA TATAGTCTTT ATGAATGCCG
```

C3R Arm

```
1101  TAAATACAAA GACGTTGATA GTATATTTAC GTTATTGTAT TTGCATTTTT
      ATTTATGTTT CTGCAACTAT CATATAAATG CAATAACATA AACGTAAAAA
```

C3R Arm

```
1151  TAAGTATATA CCTTACTAAA TTTATATCTC TATACCTTAT AGCTTTATGC
      ATTCATATAT GGAATGATTT AAATATAGAG ATATGGAATA TCGAAATACG
```

C3R Arm

```
1201  AGTTCATTTA TAAGTCTTCC ATTACTCATT TCTGGTAATG AAGTATTATA
      TCAAGTAAAT ATTCAGAAGG TAATGAGTAA AGACCATTAC TTCATAATAT
```

C3R Arm

```
1251  TATCATTATG ATATTATCTC TATTTTATTC TAATAAAAAC CGTTATCATG
      ATAGTAATAC TATAATAGAG ATAAAATAAG ATTATTTTTG GCAATAGTAC
```

C3R Arm

```
13 01 TTATTTATTA TTTGTTATAA TTATACTATT TAATAAATTA TACCAAATAC
      AATAAATAAT AAACAATATT AATATGATAA ATTATTTAAT ATGGTTTATG
```

C3R Arm

```
1351  TTAGATACTT ATTAATACCA TCCTAGAACT TGTATTTCTT GCCCCCTAAA
      AATCTATGAA TAATTATGGT AGGATCTTGA ACATAAAGAA CGGGGGATTT
```

C3R Arm

```
1401  CTTGGACATG CACTCCATTA GGCGTTTCTT GTTTTCGACA TCGTCCTCCT
      GAACCTGTAC GTGAGGTAAT CCGCAAAGAA CAAAAGCTGT AGCAGGAGGA
```

FIGURE 13D

```
                    C3R Arm
     ----------------------------------------------------
1451 TAACATATCC TACTGTTATG TGAGGATTCC ACGGATTATC TACTGTGATA
     ATTGTATAGG ATGACAATAC ACTCCTAAGG TGCCTAATAG ATGACACTAT

                    C3R Arm
     ----------------------------------------------------
1501 TCACCAAACA CGTCCTTCGA ACAGGGTACC GCATTCAGCA GAACATTTCT
     AGTGGTTTGT GCAGGAAGCT TGTCCCATGG CGTAAGTCGT CTTGTAAAGA

                    C3R Arm
     ----------------------------------------------------
1551 TAGGGCTCTA AGTTCATCAG ATACCTCCAG TTTCATAACT ACAGCGCATC
     ATCCCGAGAT TCAAGTAGTC TATGGAGGTC AAAGTATTGA TGTCGCGTAG

                    C3R Arm
     ----------------------------------------------------
1601 CTTTCGCTCC CAACTGTTTA GAGGCGTTAC TGTGAGGAAA ACACATCTCT
     GAAAGCGAGG GTTGACAAAT CTCCGCAATG AGACTCCTTT TGTGTAGAGA

                    C3R Arm
     ----------------------------------------------------
1651 TCTTTACAGA CTATAGAAAT AGTCTGTAAA TCTTGATCAG TTATTTGCTT
     AGAAATGTCT GATATCTTTA TCAGACATTT AGAACTAGTC AATAAACGAA

                    C3R Arm
     ----------------------------------------------------
1701 TTTGAAATTT TCAAATCTAT CACATTGATC CATATTTGCT ATTCCAAGAG
     AAACTTTAAA AGTTTAGATA GTGTAACTAG GTATAAACGA TAAGGTTCTC

                    C3R Arm
     ----------------------------------------------------
1751 TTATATGAGG AAAAATATCA CATCCTGTCA TGTATTTTAT TGTAACATTA
     AATATACTCC TTTTTATAGT GTAGGACAGT ACATAAAATA ACATTGTAAT

                    C3R Arm
     ----------------------------------------------------
1801 TTATAATCTG TAACATCAGT ATCTAACCTA ACGTCGTAAA AGTTAACAGA
     AATATTAGAC ATTGTAGTCA TAGATTGGAT TGCAGCATTT TCAATTGTCT

                    C3R Arm
     ----------------------------------------------------
1851 TGCCCAGTTA CTATAATCCC AAGGAACCTT AACATCTAAT CCCATTAAAA
     ACGGGTCAAT GATATTAGGG TTCCTTGGAA TTGTAGATTA GGGTAATTTT

                    C3R Arm
     ----------------------------------------------------
1901 TAGTATCCTT TCTACTATTT TTTTCATTGG CAAGTATGTG GCTTAGTTTA
     ATCATAGGAA AGATGATAAA AAAAGTAACC GTTCATACAC CGAATCAAAT

                    C3R Arm
     ----------------------------------------------------
1951 CACAAAATTC CTGCCATTTT GTAACGATAG CGAAGCAATA GCTTGTATGC
     GTGTTTTAAG GACGGTAAAA CATTGCTATC GCTTCGTTAT CGAACATACG
```

FIGURE 13E

```
                                                          H6 promoter
2001   TTTTTATTTG ATTAACTAGT CATAAAAATC GGGATCCTTC TTTATTCTAT
       AAAAATAAAC TAATTGATCA GTATTTTTAG CCCTAGGAAG AAATAAGATA

                             H6 promoter
2051   ACTTAAAAAG TGAAAATAAA TACAAAGGTT CTTGAGGGTT GTGTTAAATT
       TGAATTTTTC ACTTTTATTT ATGTTTCCAA GAACTCCCAA CACAATTTAA

                             H6 promoter
2101   GAAAGCGAGA AATAATCATA AATTATTTCA TTATCGCGAT ATCCGTTAAG
       CTTTCGCTCT TTATTAGTAT TTAATAAAGT AATAGCGCTA TAGGCAATTC

                                        MCEA
       H6 promoter
2151   TTTGTATCGT AATGGAGTCT CCCTCGGCCC CTCCCCACAG ATGGTGCATC
       AAACATAGCA TTACCTCAGA GGGAGCCGGG GAGGGGTGTC TACCACGTAG

                              MCEA
22 01   CCCTGGCAGA GGCTCCTGCT CACAGCCTCA CTTCTAACCT TCTGGAACCC
       GGGACCGTCT CCGAGGACGA GTGTCGGAGT GAAGATTGGA AGACCTTGGG

                              MCEA
2251   GCCCACCACT GCCAAGCTCA CTATTGAATC CACGCCGTTC AATGTCGCAG
       CGGGTGGTGA CGGTTCGAGT GATAACTTAG GTGCGGCAAG TTACAGCGTC

                              MCEA
2301   AGGGGAAGGA GGTGCTTCTA CTTGTCCACA ATCTGCCCCA GCATCTTTTT
       TCCCCTTCCT CCACGAAGAT GAACAGGTGT TAGACGGGGT CGTAGAAAAA

                              MCEA
2351   GGCTACAGCT GGTACAAAGG TGAAAGAGTG GATGGCAACC GTCAAATTAT
       CCGATGTCGA CCATGTTTCC ACTTTCTCAC CTACCGTTGG CAGTTTAATA

                              MCEA
2401   AGGATATGTA ATAGGAACTC AACAAGCTAC CCCAGGGCCC GCATACAGTG
       TCCTATACAT TATCCTTGAG TTGTTCGATG GGGTCCCGGG CGTATGTCAC

                              MCEA
2451   GTCGAGAGAT AATATACCCC AATGCATCCC TGCTGATCCA GAACATCATC
       CAGCTCTCTA TTATATGGGG TTACGTAGGG ACGACTAGGT CTTGTAGTAG

                              MCEA
2501   CAGAATGACA CAGGATTCTA CACCCTACAC GTCATAAAGT CAGATCTTGT
       GTCTTACTGT GTCCTAAGAT GTGGGATGTG CAGTATTTCA GTCTAGAACA
```

FIGURE 13F

```
                    MCEA
2551   GAATGAAGAA GCAACTGGCC AGTTCCGGGT ATACCCGGAA CTCCCTAAGC
       CTTACTTCTT CGTTGACCGG TCAAGGCCCA TATGGGCCTT GAGGGATTCG

                    MCEA
2601   CTTCTATTAG CTCCAATAAT AGTAAGCCTG TCGAAGACAA AGATGCCGTC
       GAAGATAATC GAGGTTATTA TCATTCGGAC AGCTTCTGTT TCTACGGCAG

                    MCEA
2651   GCTTTTACAT GCGAGCCCGA AACTCAAGAC GCAACATATC TCTGGTGGGT
       CGAAAATGTA CGCTCGGGCT TTGAGTTCTG CGTTGTATAG AGACCACCCA

                    MCEA
2701   GAACAACCAG TCCCTGCCTG TGTCCCCTAG ACTCCAACTC AGCAACGGAA
       CTTGTTGGTC AGGGACGGAC ACAGGGGATC TGAGGTTGAG TCGTTGCCTT

                    MCEA
2751   ATAGAACTCT GACCCTGTTT AACGTGACCA GGAACGACAC AGCAAGCTAC
       TATCTTGAGA CTGGGACAAA TTGCACTGGT CCTTGCTGTG TCGTTCGATG

                    MCEA
2801   AAATGCGAAA CCCAAAATCC AGTCAGCGCC AGGAGGTCTG ATTCAGTGAT
       TTTACGCTTT GGGTTTTAGG TCAGTCGCGG TCCTCCAGAC TAAGTCACTA

                    MCEA
2851   TCTCAACGTG CTTTACGGAC CCGATGCTCC TACAATCAGC CCTCTAAACA
       AGAGTTGCAC GAAATGCCTG GGCTACGAGG ATGTTAGTCG GGAGATTTGT

                    MCEA
2901   CAAGCTATAG ATCAGGGGAA AATCTGAATC TGAGCTGTCA TGCCGCTAGC
       GTTCGATATC TAGTCCCCTT TTAGACTTAG ACTCGACAGT ACGGCGATCG

                    MCEA
2951   AATCCTCCCG CCCAATACAG CTGGTTTGTC AATGGCACTT TCCAACAGTC
       TTAGGAGGGC GGGTTATGTC GACCAAACAG TTACCGTGAA AGGTTGTCAG

                    MCEA
3 001   CACCCAGGAA CTGTTCATTC CCAATATTAC CGTGAACAAT AGTGGATCCT
       GTGGGTCCTT GACAAGTAAG GGTTATAATG GCACTTGTTA TCACCTAGGA

                    MCEA
3 051   ACACGTGCCA AGCTCACAAT AGCGACACCG GACTCAACCG CACAACCGTG
       TGTGCACGGT TCGAGTGTTA TCGCTGTGGC CTGAGTTGGC GTGTTGGCAC
```

FIGURE 13G

```
                        MCEA
        ____________________________________________________
3101    ACGACGATTA CCGTGTATGA GCCACCAAAA CCATTCATAA CTAGTAACAA
        TGCTGCTAAT GGCACATACT CGGTGGTTTT GGTAAGTATT GATCATTGTT

                        MCEA
        ____________________________________________________
3151    TTCTAACCCA GTTGAGGATG AGGACGCAGT TGCATTAACT TGTGAGCCAG
        AAGATTGGGT CAACTCCTAC TCCTGCGTCA ACGTAATTGA ACACTCGGTC

                        MCEA
        ____________________________________________________
3201    AGATTCAAAA TACCACTTAT TTATGGTGGG TCAATAACCA AAGTTTGCCG
        TCTAAGTTTT ATGGTGAATA AATACCACCC AGTTATTGGT TTCAAACGGC

                        MCEA
        ____________________________________________________
3251    GTTAGCCCAC GCTTGCAGTT GTCTAATGAT AACCGCACAT TGACACTCCT
        CAATCGGGTG CGAACGTCAA CAGATTACTA TTGGCGTGTA ACTGTGAGGA

                        MCEA
        ____________________________________________________
3301    GTCCGTTACT CGCAATGATG TAGGACCTTA TGAGTGTGGC ATTCAGAATG
        CAGGCAATGA GCGTTACTAC ATCCTGGAAT ACTCACACCG TAAGTCTTAC

                        MCEA
        ____________________________________________________
3351    AATTATCCGT TGATCACTCC GACCCTGTTA TCCTTAATGT TTTGTATGGC
        TTAATAGGCA ACTAGTGAGG CTGGGACAAT AGGAATTACA AAACATACCG

                        MCEA
        ____________________________________________________
3401    CCAGACGACC CAACTATATC TCCATCATAC ACCTACTACC GTCCCGGCGT
        GGTCTGCTGG GTTGATATAG AGGTAGTATG TGGATGATGG CAGGGCCGCA

                        MCEA
        ____________________________________________________
3451    GAACTTGAGC CTTTCTTGCC ATGCAGCATC CAACCCCCCT GCACAGTACT
        CTTGAACTCG GAAAGAACGG TACGTCGTAG GTTGGGGGGA CGTGTCATGA

                        MCEA
        ____________________________________________________
3501    CCTGGCTGAT TGATGGAAAC ATTCAGCAGC ATACTCAAGA GTTATTTATA
        GGACCGACTA ACTACCTTTG TAAGTCGTCG TATGAGTTCT CAATAAATAT

                        MCEA
        ____________________________________________________
3551    AGCAACATAA CTGAGAAGAA CAGCGGACTC TATACTTGCC AGGCCAATAA
        TCGTTGTATT GACTCTTCTT GTCGCCTGAG ATATGAACGG TCCGGTTATT

                        MCEA
        ____________________________________________________
3601    CTCAGCCAGT GGTCACAGCA GGACTACAGT TAAAACAATA ACTGTTTCCG
        GAGTCGGTCA CCAGTGTCGT CCTGATGTCA ATTTTGTTAT TGACAAAGGC
```

FIGURE 13H

```
                               MCEA
         ________________________________________________________
3651     CGGAGCTGCC CAAGCCCTCC ATCTCCAGCA ACAACTCCAA ACCCGTGGAG
         GCCTCGACGG GTTCGGGAGG TAGAGGTCGT TGTTGAGGTT TGGGCACCTC

                               MCEA
         ________________________________________________________
3701     GACAAGGATG CTGTGGCCTT CACCTGTGAA CCTGAGGCTC AGAACACAAC
         CTGTTCCTAC GACACCGGAA GTGGACACTT GGACTCCGAG TCTTGTGTTG

                               MCEA
         ________________________________________________________
3751     CTACCTGTGG TGGGTAAATG GTCAGAGCCT CCCAGTCAGT CCCAGGCTGC
         GATGGACACC ACCCATTTAC CAGTCTCGGA GGGTCAGTCA GGGTCCGACG

                               MCEA
         ________________________________________________________
3801     AGCTGTCCAA TGGCAACAGG ACCCTCACTC TATTCAATGT CACAAGAAAT
         TCGACAGGTT ACCGTTGTCC TGGGAGTGAG ATAAGTTACA GTGTTCTTTA

                               MCEA
         ________________________________________________________
3851     GACGCAAGAG CCTATGTATG TGGAATCCAG AACTCAGTGA GTGCAAACCG
         CTGCGTTCTC GGATACATAC ACCTTAGGTC TTGAGTCACT CACGTTTGGC

                               MCEA
         ________________________________________________________
3901     CAGTGACCCA GTCACCCTGG ATGTCCTCTA TGGGCCGGAC ACCCCCATCA
         GTCACTGGGT CAGTGGGACC TACAGGAGAT ACCCGGCCTG TGGGGGTAGT

                               MCEA
         ________________________________________________________
3951     TTTCCCCCCC AGACTCGTCT TACCTTTCGG GAGCGAACCT CAACCTCTCC
         AAAGGGGGGG TCTGAGCAGA ATGGAAAGCC CTCGCTTGGA GTTGGAGAGG

                               MCEA
         ________________________________________________________
4001     TGCCACTCGG CCTCTAACCC ATCCCCGCAG TATTCTTGGC GTATCAATGG
         ACGGTGAGCC GGAGATTGGG TAGGGGCGTC ATAAGAACCG CATAGTTACC

                               MCEA
         ________________________________________________________
4051     GATACCGCAG CAACACACAC AAGTTCTCTT TATCGCCAAA ATCACGCCAA
         CTATGGCGTC GTTGTGTGTG TTCAAGAGAA ATAGCGGTTT TAGTGCGGTT

                               MCEA
         ________________________________________________________
4101     ATAATAACGG GACCTATGCC TGTTTTGTCT CTAACTTGGC TACTGGCCGC
         TATTATTGCC CTGGATACGG ACAAAACAGA GATTGAACCG ATGACCGGCG

                               MCEA
         ________________________________________________________
4151     AATAATTCCA TAGTCAAGAG CATCACAGTC TCTGCATCTG GAACTTCTCC
         TTATTAAGGT ATCAGTTCTC GTAGTGTCAG AGACGTAGAC CTTGAAGAGG
```

FIGURE 13I

```
                               MCEA
4201  TGGTCTCTCA GCTGGGGCCA CTGTCGGCAT CATGATTGGA GTGCTGGTTG
      ACCAGAGAGT CGACCCCGGT GACAGCCGTA GTACTAACCT CACGACCAAC

          MCEA
4251  GGGTTGCTCT GATATAGTTT TTATCTCGAG GAATTCCTGC AGCCCGGGTT
      CCCAACGAGA CTATATCAAA AATAGAGCTC CTTAAGGACG TCGGGCCCAA

                                        C3L Arm
4301  TTTATAGCTA ATTAGTCAAA TGTGAGTTAA TATTAGTATA CTACATTACT
      AAATATCGAT TAATCAGTTT ACACTCAATT ATAATCATAT GATGTAATGA

                               C3L Arm
4351  AATTTATTAC ATATTCATTT ATATCAATCT AGTAGCATTT AGCTTTTATA
      TTAAATAATG TATAAGTAAA TATAGTTAGA TCATCGTAAA TCGAAAATAT

                               C3L Arm
4401  AAACAATATA ACTGAATAGT ACATACTTTA CTAATAAGTT ATAAATAAGA
      TTTGTTATAT TGACTTATCA TGTATGAAAT GATTATTCAA TATTTATTCT

                               C3L Arm
4451  GATACATATT TATAGTATTT TACTTTCTAC ACTGAATATA ATAATATAAT
      CTATGTATAA ATATCATAAA ATGAAAGATG TGACTTATAT TATTATATTA

                               C3L Arm
4501  TATACAAATA TAATTTTTAA TACTATATAG TATATAACTG AAATAAAATA
      ATATGTTTAT ATTAAAAATT ATGATATATC ATATATTGAC TTTATTTTAT

                               C3L Arm
4551  CCAGTGTAAT ATAGTTATTA TACATTTATA CCACATCAAA GATGAGTTAT
      GGTCACATTA TATCAATAAT ATGTAAATAT GGTGTAGTTT CTACTCAATA

                               C3L Arm
4601  AACATCAGTG TCACTGTTAG CAACAGTAGT TATACGATGA GTAGTTACTC
      TTGTAGTCAC AGTGACAATC GTTGTCATCA ATATGCTACT CATCAATGAG

                               C3L Arm
4651  TCGTATGGCG TTAGTATGTA TGTATCTTCT AGTTTTCTTA GTAGGCATTA
      AGCATACCGC AATCATACAT ACATAGAAGA TCAAAAGAAT CATCCGTAAT

                               C3L Arm
4701  TAGGAAACGT CAAGCTTATA AGGTTATTAA TGGTATCTAG AAATATATCT
      ATCCTTTGCA GTTCGAATAT TCCAATAATT ACCATAGATC TTTATATAGA
```

FIGURE 13J

```
                    C3L Arm
       ___________________________________________________
4751   ATTATACCGT TTCTCAACTT GGGAATAGCC GATTTGCTGT TTGTGATATT
       TAATATGGCA AAGAGTTGAA CCCTTATCGG CTAAACGACA AACACTATAA

                    C3L Arm
       _______________________________________________
4801   CATACCTTTA TACATTATAT ACATACTAAG TAATTTCCAT TGGCATTTTG
       GTATGGAAAT ATGTAATATA TGTATGATTC ATTAAAGGTA ACCGTAAAAC

                    C3L Arm
       _______________________________________________
4851   GTAAAGCACT TTGTAAAATT AGTTCTTTCT TTTTTACTTC TAACATGTTT
       CATTTCGTGA AACATTTTAA TCAAGAAAGA AAAAATGAAG ATTGTACAAA

                    G3L Arm
       _______________________________________________
4901   GCAAGTATAT TTTTAATAAC TGTAATAAGC GTATATAGAT ATGTAAAAAT
       CGTTCATATA AAAATTATTG ACATTATTCG CATATATCTA TACATTTTTA

                    C3L Arm
       _______________________________________________
4951   TACCCTTCCT GGATTTACCT ATAAATATGT TAACATTAGA AATATGTACA
       ATGGGAAGGA CCTAAATGGA TATTTATACA ATTGTAATCT TTATACATGT

                    C3L Arm
       _______________________________________________
5001   TTACTATATT TTTCATATGG ATTATTTCTA TTATACTAGG GATTCCTGCT
       AATGATATAA AAAGTATACC TAATAAAGAT AATATGATCC CTAAGGACGA

                    C3L Arm
       _______________________________________________
5051   CTTTACTTTA GAAATACTAT CGTAACAAAA AATAACGACA CGCTGTGTAT
       GAAATGAAAT CTTTATGATA GCATTGTTTT TTATTGCTGT GCGACACATA

                    C3L Arm
       _______________________________________________
5101   TAATCATTAT CATGATAATA GAGAAATTGC TGAATTGATT TACAAAGTTA
       ATTAGTAATA GTACTATTAT CTCTTTAACG ACTTAACTAA ATGTTTCAAT

                    C3L Arm
       _______________________________________________
5151   TTATCTGTAT CAGATTTATT TTAGGATACC TACTACCTAC GATAATTATA
       AATAGACATA GTCTAAATAA AATCCTATGG ATGATGGATG CTATTAATAT

                    C3L Arm
       _______________________________________________
5201   CTCGTATGCT ATACGTTACT GATCTACAGA ACTAACAATG CATGTCGACG
       GAGCATACGA TATGCAATGA CTAGATGTCT TGATTGTTAC GTACAGCTGC

       C3L Arm
       _____
5251   CGGCCGCAA
       GCCGGCGTT
```

MODIFIED CEA/B7 VECTOR

RELATED APPLICATIONS

This application is a 35 U.S.C. §371 national stage application of International Application No. PCT/US2004/033145, filed Oct. 6, 2004, and claims priority to U.S. Prov. Appln. No. 60/509,593 filed Oct. 8, 2003, which are incorporated by reference herein in their entirety.

FIELD OF THE INVENTION

The present invention relates to a nucleic acid encoding a polypeptide and the use of the nucleic acid or polypeptide in preventing and/or treating cancer. In particular, the invention relates to improved vectors for the insertion and expression of foreign genes encoding tumor antigens for use in immunotherapeutic treatment of cancer.

BACKGROUND OF THE INVENTION

There has been tremendous increase in last few years in the development of cancer vaccines with Tumour-associated antigens (TAAs) due to the great advances in identification of molecules based on the expression profiling on primary tumours and normal cells with the help of several techniques such as high density microarray, SEREX, immunohistochemistry (IHC), RT-PCR, in-situ hybridization (ISH) and laser capture microscopy (Rosenberg, Immunity, 1999; Sgroi et al, 1999, Schena et al, 1995, Offring a et al, 2000). The TAAs are antigens expressed or over-expressed by tumour cells and could be specific to one or several tumours for example CEA antigen is expressed in colorectal, breast and lung cancers. Sgroi et al (1999) identified several genes differentially expressed in invasive and metastatic carcinoma cells with combined use of laser capture microdissection and cDNA microarrays. Several delivery systems like DNA or viruses could be used for therapeutic vaccination against human cancers (Bonnet et al, 2000) and can elicit immune responses and also break immune tolerance against TAAs. Tumour cells can be rendered more immunogenic by inserting transgenes encoding T cell co-stimulatory molecules such as B7.1 or cytokines IFNgamma, IL2, GM-CSF etc. Co-expression of a TAA and a cytokine or a co-stimulatory molecule can develop effective therapeutic vaccine (Hodge et al, 95, Bronte et al, 1995, Chamberlain et al, 1996).

There is a need in the art for reagents and methodologies useful in stimulating an immune response to prevent or treat cancers. The present inventions provides such reagents and methodologies which overcome many of the difficulties encountered by others in attempting to treat cancers such as cancer. In particular, the present invention provides a novel coding sequence for CEA. This nucleotide sequence, CEA (6D)-1,2, includes sequence modifications that eliminate the expression of truncated forms of CEA as expressed from expression vectors. Such a modified sequence is desired by those of skill in the art to improve expression and immunization protocols for CEA.

SUMMARY OF THE INVENTION

The present invention provides an immunogenic target for administration to a patient to prevent and/or treat cancer. In particular, the immunogenic target is a CEA tumor antigen ("TA") and/or an angiogenesis-associated antigen ("AA"). In one embodiment, the immungenic target is encoded by a modified CEA nucleotide sequence (CEA(6D)-1,2) that improves CEA expression in transfected cells. In certain embodiments, the TA and/or AA are administered to a patient as a nucleic acid contained within a plasmid or other delivery vector, such as a recombinant virus. The TA and/or AA may also be administered in combination with an immune stimulator, such as a co-stimulatory molecule or adjuvant.

BRIEF DESCRIPTION OF THE DRAWINGS

FIG. 1. A. Illustration of plasmid p3'H6MCEA comprising the CEA coding sequence with the 6D modification under the control of partial H6 promoter. B. Illustration of plasmid pSE1544.9 (pUC18-mCEArepeat1).

FIG. 9A-D. Comparison of nucleotide sequence of CAP (6D) and CAP(6D)-1,2. Differences between the sequences are underlined.

FIG. 12A-E. Human B7.1 gene in an ALVAC C6 donor plasmid under the control of the H6 promoter (SEQ ID NOS.: 11, 12).

FIG. 13A-J. CAP(6D)-1,2 CEA DNA sequence in an ALVAC C3 donor plasmid under the control of the H6 promoter (SEQ ID NOS.: 13, 14).

DETAILED DESCRIPTION

Figure 2:
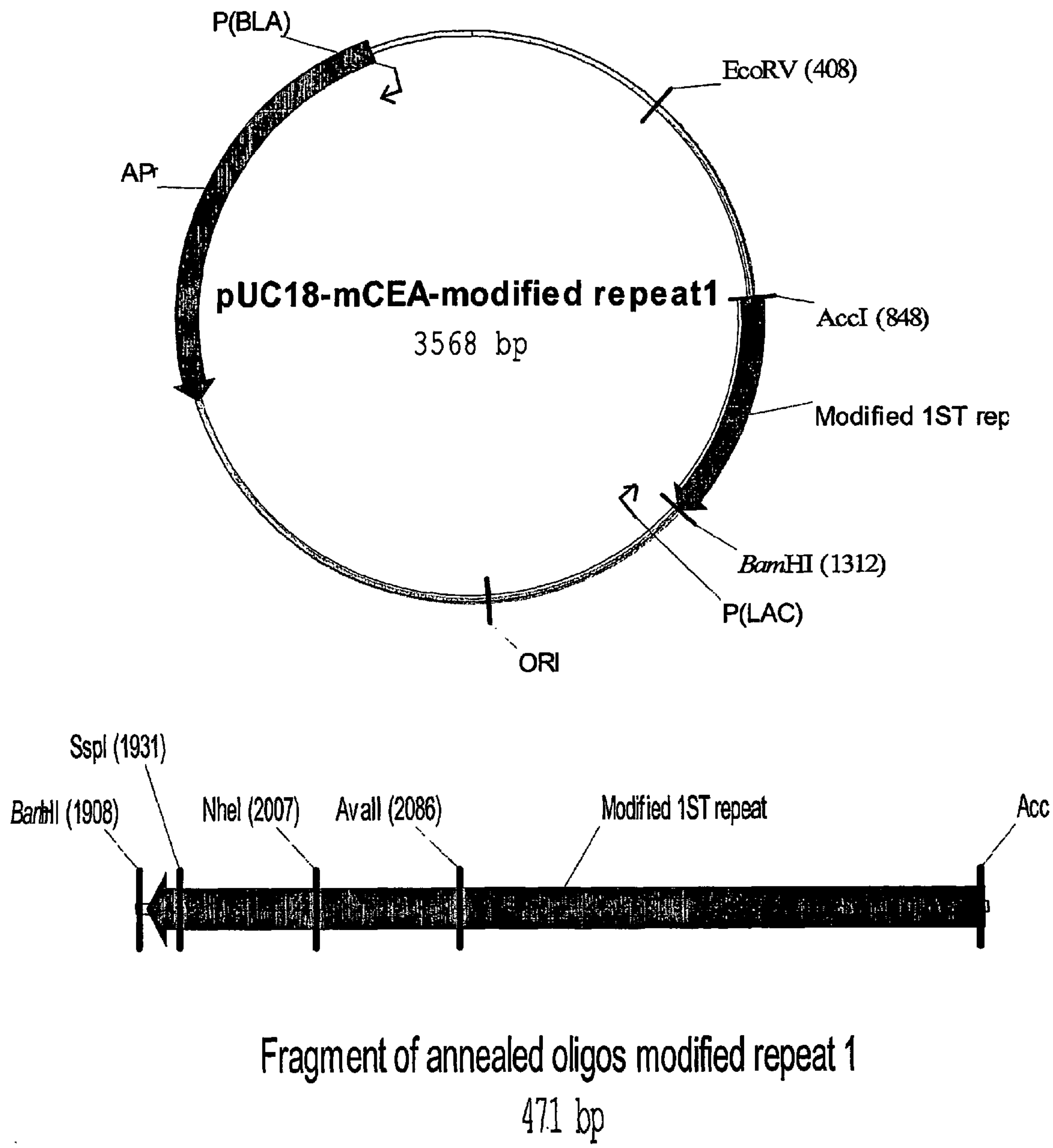
FIG. 2. Illustration of plasmid pSE1616.44 (pUC18-mCEA-modified repeat 1).

The present invention provides reagents and methodologies useful for treating and/or preventing cancer. All references cited within this application are incorporated by reference.

In one embodiment, the present invention relates to the induction or enhancement of an immune response against one or more tumor antigens ("TA") to prevent and/or treat cancer. In certain embodiments, one or more TAs may be combined. In preferred embodiments, the immune response results from expression of a TA in a host cell following administration of a nucleic acid vector encoding the tumor antigen or the tumor antigen itself in the form of a peptide or polypeptide, for example.

As used herein, an "antigen" is a molecule (such as a polypeptide) or a portion thereof that produces an immune response in a host to whom the antigen has been administered. The immune response may include the production of antibodies that bind to at least one epitope of the antigen and/or the generation of a cellular immune response against cells expressing an epitope of the antigen. The response may be an enhancement of a current immune response by, for example, causing increased antibody production, production of antibodies with increased affinity for the antigen, or an increased cellular response (i.e., increased T cells). An antigen that produces an immune response may alternatively be referred to as being immunogenic or as an immunogen. In describing the present invention, a TA may be referred to as an "immunogenic target".

TA includes both tumor-associated antigens (TAAs) and tumor-specific antigens (TSAs), where a cancerous cell is the source of the antigen. A TAA is an antigen that is expressed on the surface of a tumor cell in higher amounts than is observed on normal cells or an antigen that is expressed on normal cells during fetal development. A TSA is an antigen that is unique to tumor cells and is not expressed on normal cells. TA further includes TAAs or TSAs, antigenic fragments thereof, and modified versions that retain their antigenicity.

TAs are typically classified into five categories according to their expression pattern, function, or genetic origin: cancer-testis (CT) antigens (i.e., MAGE, NY-ESO-1); melanocyte differentiation antigens (i.e., Melan A/MART-1, tyrosinase, gp100); mutational antigens (i.e., MUM-1, p53, CDK-4); overexpressed 'self' antigens (i.e., HER-2/neu, p53); and, viral antigens (i.e., HPV, EBV). For the purposes of practicing the present invention, a suitable TA is any TA that induces or enhances an anti-tumor immune response in a host to whom the TA has been administered. Suitable TAs include, for example, gp100 (Cox et al., *Science,* 264:716-719 (1994)), MART-1/Melan A (Kawakami et al., *J. Exp. Med.,* 180:347-352 (1994)), gp75 (TRP-1) (Wang et al., *J. Exp. Med.,* 186:1131-1140 (1996)), tyrosinase (Wolfel et al., *Eur. J. Immunol.,* 24:759-764 (1994); WO 200175117; WO 200175016; WO 200175007), NY-ESO-1 (WO 98/14464; WO 99/18206), melanoma proteoglycan (Hellstrom et al., *J. Immunol.,* 130:1467-1472 (1983)), MAGE family antigens (i.e., MAGE-1, 2,3,4,6,12,51; Van der Bruggen et al., *Science,* 254:1643-1647 (1991); U.S. Pat. No. 6,235,525; CN 1319611), BAGE family antigens (Boel et al., *Immunity,* 2:167-175 (1995)), GAGE family antigens (i.e., GAGE-1,2; Van den Eynde et al., *J. Exp. Med.,* 182:689-698 (1995); U.S. Pat. No. 6,013,765), RAGE family antigens (i.e., RAGE-1; Gaugler et al., *Immunogenetics,* 44:323-330 (1996); U.S. Pat. No. 5,939,526), N-acetylglucosaminyltransferase-V (Guilloux et al., *J. Exp. Med.,* 183:1173-1183 (1996)), p15 (Robbins et al., *J. Immunol.* 154:5944-5950 (1995)), β-catenin (Robbins et al., *J. Exp. Med.,* 183:1185-1192 (1996)), MUM-1 (Coulie et al., *Proc. Natl. Acad. Sci. USA,* 92:7976-7980 (1995)), cyclin dependent kinase-4 (CDK4) (Wolfel et al., *Science,* 269:1281-1284 (1995)), p21-ras (Fossum et at., Int. J. Cancer, 56:40-45 (1994)), BCR-abl (Bocchia et al., *Blood,* 85:2680-2684 (1995)), p53 (Theobald et al., *Proc. Natl. Acad. Sci. USA,* 92:11993-11997 (1995)), p185 HER2/neu (erb-B1; Fisk et al., *J. Exp. Med.,* 181:2109-2117 (1995)), epidermal growth factor receptor (EGFR) (Harris et al., Breast Cancer Res. Treat, 29:1-2 (1994)), carcinoembryonic antigens (CEA) (Kwong et al., *J. Natl. Cancer Inst.,* 85:982-990 (1995) U.S. Pat. Nos. 5,756,103; 5,274,087; 5,571,710; 6,071,716; 5,698,530; 6,045,802; EP 263933; EP 346710; and, EP 784483); carcinoma-associated mutated mucins (i.e., MUC-1 gene products; Jerome et al., *J. Immunol.,* 151:1654-1662 (1993)); EBNA gene products of EBV (i.e., EBNA-1; Rickinson et al., *Cancer Surveys,* 13:53-80 (1992)); E7, E6 proteins of human papillomavirus (Ressing et al., *J. Immunol,* 154:5934-5943 (1995)); prostate specific antigen (PSA; Xue et al., *The Prostate,* 30:73-78 (1997)); prostate specific membrane antigen (PSMA; Israeli, et al., *Cancer Res.,* 54:1807-1811 (1994)); idiotypic epitopes or antigens, for example, immunoglobulin idiotypes or T cell receptor idiotypes (Chen et al., *J. Immunol.,* 153:4775-4787 (1994)); KSA (U.S. Pat. No. 5,348,887), kinesin 2 (Dietz, et al. *Biochem Biophys Res Commun* 2000 Sep. 7; 275(3):731-8), HIP-55, TGFβ-1 anti-apoptotic factor (Toomey, et al. *Br J Biomed Sci* 2001; 58(3): 177-83), tumor protein D52 (Bryne J. A., et al., *Genomics,* 35:523-532 (1996)), $H_1$FT, NY-BR-1 (WO 01/47959), NY-BR-62, NY-BR-75, NY-BR-85, NY-BR-87, NY-BR-96 (Scanlan, M. Serologic and Bioinformatic Approaches to the Identification of Human Tumor Antigens, in *Cancer Vaccines* 2000, Cancer Research Institute, New York, N.Y.), including "wild-type" (i.e., normally encoded by the genome, naturally-occurring), modified, and mutated versions as well as other fragments and derivatives thereof. Any of these TAs may be utilized alone or in combination with one another in a co-immunization protocol.

In certain cases, it may be beneficial to co-immunize patients with both TA and other antigens, such as angiogenesis-associated antigens ("AA"). An AA is an immunogenic molecule (i.e., peptide, polypeptide) associated with cells involved in the induction and/or continued development of blood vessels. For example, an AA may be expressed on an endothelial cell ("EC"), which is a primary structural component of blood vessels. Where the cancer is cancer, it is preferred that that the AA be found within or near blood vessels that supply a tumor. Immunization of a patient against an AA preferably results in an anti-AA immune response whereby angiogenic processes that occur near or within tumors are prevented and/or inhibited.

Exemplary AAs include, for example, vascular endothelial growth factor (i.e., VEGF; Bernardini, et al. *J. Urol.,* 2001, 166(4): 1275-9; Starnes, et al. *J. Thorac. Cardiovasc. Surg.,* 2001, 122(3): 518-23), the VEGF receptor (i.e., VEGF-R, flk-1/KDR; Starnes, et al. *J. Thorac. Cardiovasc. Surg.,* 2001, 122(3): 518-23), EPH receptors (i.e., EPHA2; Gerety, et al. 1999, Cell, 4: 403-414), epidermal growth factor receptor (i.e., EGFR; Clardeillo, et al. *Clin. Cancer Res.,* 2001, 7(10): 2958-70), basic fibroblast growth, factor (i.e., bFGF; Davidson, et al. Clin. Exp. Metastasis 2000, 18(6): 501-7; Poon, et al. Am J. Surg., 2001, 182(3):298-304), platelet-derived cell growth factor (i.e., PDGF-B), platelet-derived endothelial cell growth factor (PD-ECGF; Hong, et al. J. Mol. Med., 2001, 8(2):141-8), transforming growth factors (i.e., TGF-α; Hong, et al. J. Mol. Med., 2001, 8(2):141-8), endoglin (Balza, et al. *Int. J. Cancer,* 2001, 94: 579-585), Id proteins (Benezra, R. Trends Cardiovasc. Med., 2001, 11(6):237-41), proteases such as uPA, uPAR, and matrix metalloproteinases (MMP-2, MMP-9; Djonov, et al. J. Pathol., 2001, 195(2):147-55), nitric oxide synthase (Am. J. Ophthalmol., 2001, 132(4):551-6), aminopeptidase (Rouslhati, E. Nature Cancer, 2: 84-90, 2002), thrombospondins (i.e., TSP-1, TSP-2; Alvarez, et al. Gynecol. Oncol., 2001, 82(2):273-8; Seki, et al. Int. J. Oncol., 2001, 19(2):305-10), k-ras (Zhang, et al. Cancer Res., 2001, 61(16):6050-4), Wnt (Zhang, et al. *Cancer Res.,* 2001, 61(16):6050-4), cyclin-dependent kinases (CDKs; Drug Resist. Updat. 2000, 3(2):83-88), microtubules (Timar, et al. 2001. *Path. Oncol. Res.,* 7(2): 85-94), heat shock nrnteins (i.e., HSP90 (Timar, supra)), heparin-binding factors (i.e., heparinase; Gohji, et al Int. J. Cancer, 2001, 95(5):295-301), synthases (i.e., ATP synthase, thymidilate synthase), collagen receptors, integrins (i.e., $\alpha v\beta 3$, $\alpha v\beta 5$, $\alpha 1\beta 1$, $\alpha 2\beta 1$, $\alpha 5\approx 1$), the surface proteolglycan NG2, AAC2-1 (SEQ ID NO.:1), or AAC2-2 (SEQ ID NO.:2), among others, including "wild-type" (i.e., normally encoded by the genome, naturally-occurring), modified, mutated versions as well as other fragments and derivatives thereof. Any of these targets may be suitable in practicing the present invention, either alone or in combination with one another or with other agents.

In certain embodiments, a nucleic acid molecule encoding an immunogenic target is utilized. The nucleic acid molecule may comprise or consist of a nucleotide sequence encoding one or more immunogenic targets, or fragments or derivatives thereof, such as that contained in a DNA insert in an ATCC Deposit. The term "nucleic acid sequence" or "nucleic acid molecule" refers to a DNA or RNA sequence. The term encompasses molecules formed from any of the known base analogs of DNA and RNA such as, but not limited to 4-acetylcytosine, 8-hydroxy-N-6-methyladenosine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxy-methylaminomethyluracil, dihydrouracil, inosine, N6-iso-pentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonyl-methyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine, among others.

An isolated nucleic acid molecule is one that: (1) is separated from at least about 50 percent of proteins, lipids, carbohydrates, or other materials with which it is naturally found when total nucleic acid is isolated from the source cells; (2) is not be linked to all or a portion of a polynucleotide to which the nucleic acid molecule is linked in nature; (3) is operably linked to a polynucleotide which it is not linked to in nature; and/or, (4) does not occur in nature as part of a larger polynucleotide sequence. Preferably, the isolated nucleic acid molecule of the present invention is substantially free from any other contaminating nucleic acid molecule(s) or other contaminants that are formed in its natural environment that would interfere with its use in polypeptide production or its therapeutic, diagnostic, prophylactic or research use. As used herein, the term "naturally occurring" or "native" or "naturally found" when used in connection with biological materials such as nucleic acid molecules, polypeptides, host cells, and the like, refers to materials which are found in nature and are not manipulated by man. Similarly, "non-naturally occurring" or "non-native" as used herein refers to a material that is not found in nature or that has been structurally modified or synthesized by man.

The identity of two or more nucleic acid or polypeptide molecules is determined by comparing the sequences. As known in the art, "identity" means the degree of sequence relatedness between nucleic acid molecules or polypeptides as determined by the match between the units making up the molecules (i.e., nucleotides or amino acid residues). Identity measures the percent of identical matches between the smaller of two or more sequences with gap alignments (if any) addressed by a particular mathematical model or computer program (i.e., an algorithm). Identity between nucleic acid sequences may also be determined by the ability of the related sequence to hybridize to the nucleic acid sequence or isolated nucleic acid molecule. In defining such sequences, the term "highly stringent conditions" and "moderately stringent conditions" refer to procedures that permit hybridization of nucleic acid strands whose sequences are complementary, and to exclude hybridization of significantly mismatched nucleic acids. Examples of "highly stringent conditions" for hybridization and washing are 0.015 M sodium chloride, 0.0015 M sodium citrate at 65-68° C. or 0.015 M sodium chloride, 0.0015 M sodium citrate, and 50% formamide at 42° C. (see, for example, Sambrook, Fritsch & Maniatis, *Molecular. Cloning: A Laboratory Manual* (2nd ed., Cold Spring Harbor Laboratory, 1989); Anderson et al., *Nucleic Acid Hybridisation: A Practical Approach* Ch. 4 (IRL Press Limited)). The term "moderately stringent conditions" refers to conditions under which a DNA duplex with a greater degree of base pair mismatching than could occur under "highly stringent conditions" is able to form. Exemplary moderately stringent conditions are 0.015 M sodium chloride, 0.0015 M sodium citrate at 50-65° C. or 0.015 M sodium chloride, 0.0015 M sodium citrate, and 20% formamide at 37-50° C. By way of example, moderately stringent conditions of 50° C. in 0.015 M sodium ion will allow about a 21% mismatch. During hybridization, other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, $NaDodSO_4$, (SDS), ficoll, Denhardt's solution, sonicated salmon sperm DNA (or another non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4; however, at typical ionic strength conditions, the rate of hybridization is nearly independent of pH.

In preferred embodiments of the present invention, vectors are used to transfer a nucleic acid sequence encoding a polypeptide to a cell. A vector is any molecule used to transfer a nucleic acid sequence to a host cell. In certain cases, an expression vector is utilized. An expression vector is a nucleic acid molecule that is suitable for transformation of a host cell and contains nucleic acid sequences that direct and/or control the expression of the transferred nucleic acid sequences. Expression includes, but is not limited to, processes such as transcription, translation, and splicing, if introns are present. Expression vectors typically comprise one or more flanking sequences operably linked to a heterologous nucleic acid sequence encoding a polypeptide. Flanking sequences may be homologous (i.e., from the same species and/or strain as the host cell), heterologous (i.e., from a species other than the host cell species or strain), hybrid (i.e., a combination of flanking sequences from more than one source), or synthetic, for example.

A flanking sequence is preferably capable of effecting the replication, transcription and/or translation of the coding sequence and is operably linked to a coding sequence. As used herein, the term operably linked refers to a linkage of polynucleotide elements in a functional relationship. For instance, a promoter or enhancer is operably linked to a coding sequence if it affects the transcription of the coding sequence. However, a flanking sequence need not necessarily be contiguous with the coding sequence, so long as it functions correctly. Thus, for example, intervening untranslated yet transcribed sequences can be present between a promoter sequence and the coding sequence and the promoter sequence may still be considered operably linked to the coding sequence. Similarly, an enhancer sequence may be located upstream or downstream from the coding sequence and affect transcription of the sequence.

In certain embodiments, it is preferred that the flanking sequence is a trascriptional regulatory region that drives high-level gene expression in the target cell. The transcriptional regulatory region may comprise, for example, a promoter, enhancer, silencer, repressor element, or combinations thereof. The transcriptional regulatory region may be either constitutive, tissue-specific, cell-type specific (i.e., the region is drives higher levels of transcription in a one type of tissue or cell as compared to another), or regulatable (i.e., responsive to interaction with a compound such as tetracycline). The source of a transcriptional regulatory region may be any prokaryotic or eukaryotic organism, any vertebrate or invertebrate organism, or any plant, provided that the flanking sequence functions in a cell by causing transcription of a nucleic acid within that cell. A wide variety of transcriptional regulatory regions may be utilized in practicing the present invention.

Suitable transcriptional regulatory regions include the CMV promoter (i.e., the CMV-immediate early promoter); promoters from eukaryotic genes (i.e., the estrogen-inducible chicken ovalbumin gene, the interferon genes, the glucocorticoid-inducible tyrosine to aminotransferase gene, and the thymidine kinase gene); and the major early and late adenovirus gene promoters; the SV40 early promoter region (Bernoist and Chambon, 1981, *Nature* 290:304-10); the promoter contained in the 3' long terminal repeat (LTR) of Rous sarcoma virus (RSV) (Yamamoto, et al., 1980, *Cell* 22:787-97); the herpes simplex virus thymidine kinase (HSV-TK) promoter (Wagner et al., 1981, *Proc. Natl. Acad. Sci. U.S.A.* 78:1444-45); the regulatory sequences of the metallothionine gene (Brinster et al., 1982, *Nature* 296:39-42); prokaryotic expression vectors such as the beta-lactamase promoter (VIIIa-Kamaroff et al., 1978, *Proc. Natl. Acad. Sci. USA.,* 75:3727-31); or the tac promoter (DeBoer et al., 1983, *Proc. Natl. Acad. Sci. USA,* 80:21-25). Tissue- and/or cell-type specific transcriptional control regions include, for example, the elastase I gene control region which is active in pancreatic acinar cells (Swift et al., 1984, *Cell* 38:639-46; Ornitz et al., 1986, *Cold Spring Harbor Symp. Quant. Biol.* 50:399-409 (1986); MacDonald, 1987, *Hepatology* 7:425-515); the insulin gene control region which is active in pancreatic beta cells (Hanahan, 1985, *Nature* 315:115-22); the immunoglobulin gene control region which is active in lymphoid cells (Grosschedl et al., 1984, *Cell* 38:647-58; Adames et al., 1985, *Nature* 318:533-38; Alexander et al., 1987, *Mol. Cell. Biol.,* 7:1436-44); the mouse mammary tumor virus control region in testicular, breast, lymphoid and mast cells (Leder et al., 1986, *Cell* 45:485-95); the albumin gene control region in liver (Pinkert et al., 1987, *Genes and Devel.* 1:268-76); the alpha-feto-protein gene control region in liver (Krumlauf et al., 1985, *Mol. Cell. Biol.,* 5:1639-48; Hammer et al., 1987, *Science* 235:53-58); the alpha 1-antitrypsin gene control region in liver (Kelsey et al., 1987, *Genes and Devel.* 1:161-71); the beta-globin gene control region in myeloid cells (Mogram et al., 1985, *Nature* 315:338-40; Kollias et al., 1986, *Cell* 46:89-94); the myelin basic protein gene control region in oligodendrocyte cells in the brain (Readhead et al., at 1987, *Cell* 48:703-12); the myosin light chain-2 gene control region in skeletal muscle (Sari, 1985, *Nature* 314:283-86); the gonadotropic releasing hormone gene control region in the hypothalamus (Mason et al., 1986, *Science* 234:1372-78), and the tyrosinase promoter in melanoma cells (Hart, I. Semin Oncol 1996 February; 23(1):154-8; Siders, et al. Cancer Gene Ther 1998 September-October; 5(5):281-91), among others. Other suitable promoters are known in the art.

As described above, enhancers may also be suitable flanking sequences. Enhancers are cis-acting elements of DNA, usually about 10-300 bp in length, that act on the promoter to increase transcription. Enhancers are typically orientation- and position-independent, having been identified both 5' and 3' to controlled coding sequences. Several enhancer sequences available from mammalian genes are known (i.e., globin, elastase, albumin, alpha-feto-protein and insulin). Similarly, the SV40 enhancer, the cytomegalovirus early promoter enhancer, the polyoma enhancer, and adenovirus enhancers are useful with eukaryotic promoter sequences. While an enhancer may be spliced into the vector at a position 5' or 3' to nucleic acid coding sequence, it is typically located at a site 5' from the promoter. Other suitable enhancers are known in the art, and would be applicable to the present invention.

While preparing reagents of the present invention, cells may need to be transfected or transformed. Transfection refers to the uptake of foreign or exogenous DNA by a cell, and a cell has been transfected when the exogenous DNA has been introduced inside the cell membrane. A number of transfection techniques are well known in the art (i.e., Graham et al., 1973, *Virology* 52:456; Sambrook et al., *Molecular Cloning, A Laboratory Manual* (Cold Spring Harbor Laboratories, 1989); Davis et al., *Basic Methods in Molecular Biology* (Elsevier, 1986); and Chu et al., 1981, *Gene* 13:197). Such techniques can be used to introduce one or more exogenous DNA moieties into suitable host cells.

In certain embodiments, it is preferred that transfection of a cell results in transformation of that cell. A cell is transformed when there is a change in a characteristic of the cell, being transformed when it has been modified to contain a new nucleic acid. Following transfection, the transfected nucleic acid may recombine with that of the cell by physically integrating into a chromosome of the cell, may be maintained transiently as an episomal element without being replicated, or may replicate independently as a plasmid. A cell is stably transformed when the nucleic acid is replicated with the division of the cell.

The present invention further provides isolated immunogenic targets in polypeptide form. A polypeptide is considered isolated where it: (1) has been separated from at least about 50 percent of polynucleotides, lipids, carbohydrates, or other materials with which it is naturally found when isolated from the source cell; (2) is not linked (by covalent or noncovalent interaction) to all or a portion of a polypeptide to which the "isolated polypeptide" is linked in nature; (3) is operably linked (by covalent or noncovalent interaction) to a polypeptide with which it is not linked in nature; or, (4) does not occur in nature. Preferably, the isolated polypeptide is substantially free from any other contaminating polypeptides or other contaminants that are found in its natural environment that would interfere with its therapeutic, diagnostic, prophylactic or research use.

Immunogenic target polypeptides may be mature polypeptides, as defined herein, and may or may not have an amino terminal methionine residue, depending on the method by which they are prepared. Further contemplated are related polypeptides such as, for example, fragments, variants (i.e., allelic, splice), orthologs, homologues, and derivatives, for example, that possess at least one characteristic or activity (i.e., activity, antigenicity) of the immunogenic target. Also related are peptides, which refers to a series of contiguous amino acid residues having a sequence corresponding to at least a portion of the polypeptide from which its sequence is derived. In preferred embodiments, the peptide comprises about 5-10 amino acids, 10-15 amino acids, 15-20 amino acids, 20-30 amino acids, or 30-50 amino acids. In a more preferred embodiment, a peptide comprises 9-12 amino acids, suitable for presentation upon Class I MHC molecules, for example.

A fragment of a nucleic acid or polypeptide comprises a truncation of the sequence (i.e., nucleic acid or polypeptide) at the amino terminus (with or without a leader sequence) and/or the carboxy terminus. Fragments may also include variants (i.e., allelic, splice), orthologs, homologues, and other variants having one or more amino acid additions or substitutions or internal deletions as compared to the parental sequence. In preferred embodiments, truncations and/or deletions comprise about 10 amino acids, 20 amino acids, 30 amino acids, 40 amino acids, 50 amino acids, or more. The polypeptide fragments so produced will comprise about 10 amino acids, 25 amino acids, 30 amino acids, 40 amino acids, 50 amino acids, 60 amino acids, 70 amino acids, or more. Such polypeptide fragments may optionally comprise an amino terminal methionine residue. It will be appreciated that such fragments can be used, for example, to generate antibodies or cellular immune responses to immunogenic target polypeptides.

A variant is a sequence having one or more sequence substitutions, deletions, and/or additions as compared to the subject sequence. Variants may be naturally occurring or artificially constructed. Such variants may be prepared from the corresponding nucleic acid molecules. In preferred embodiments, the variants have from 1 to 3, or from 1 to 5, or from 1 to 10, or from 1 to 15, or from 1 to 20, or from 1 to 25, or from 1 to 30, or from 1 to 40, or from 1 to 50, or more than 50 amino acid substitutions, insertions, additions and/or deletions.

An allelic variant is one of several possible naturally-occurring alternate forms of a gene occupying a given locus on a chromosome of an organism or a population of organisms. A splice variant is a polypeptide generated from one of several RNA transcript resulting from splicing of a primary transcript. An ortholog is a similar nucleic acid or polypeptide sequence from another species. For example, the mouse and human versions of an immunogenic target polypeptide may be considered orthologs of each other. A derivative of a sequence is one that is derived from a parental sequence those sequences having substitutions, additions, deletions, or chemically modified variants. Variants may also include fusion proteins, which refers to the fusion of one or more first sequences (such as a peptide) at the amino or carboxy terminus of at least one other sequence (such as a heterologous peptide).

"Similarity" is a concept related to identity, except that similarity refers to a measure of relatedness which includes both identical matches and conservative substitution matches. If two polypeptide sequences have, for example, 10/20 identical amino acids, and the remainder are all non-conservative substitutions, then the percent identity and similarity would both be 50%. If in the same example, there are five more positions where there are conservative substitutions, then the percent identity remains 50%, but the percent similarity would be 75% (15/20). Therefore, in cases where there are conservative substitutions, the percent similarity between two polypeptides will be higher than the percent identity between those two polypeptides.

Substitutions may be conservative, or non-conservative, or any combination thereof. Conservative amino acid modifications to the sequence of a polypeptide (and the corresponding modifications to the encoding nucleotides) may produce polypeptides having functional and chemical characteristics similar to those of a parental polypeptide. For example, a "conservative amino acid substitution" may involve a substitution of a native amino acid residue with a non-native residue such that there is little or no effect on the size, polarity, charge, hydrophobicity, or hydrophilicity of the amino acid residue at that position and, in particular, does not result in decreased immunogenicity. Suitable conservative amino acid substitutions are shown in Table I.

TABLE I

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of polypeptide using well-known techniques. For identifying suitable areas of the molecule that may be changed without destroying biological activity (i.e., MHC binding, immunogenicity), one skilled in the art may target areas not believed to be important for that activity. For example, when similar polypeptides with similar activities from the same species or from other species are known, one skilled in the art may compare the amino acid sequence of a polypeptide to such similar polypeptides. By performing such analyses, one can identify residues and portions of the molecules that are conserved among similar polypeptides. It will be appreciated that changes in areas of the molecule that are not conserved relative to such similar polypeptides would be less likely to adversely affect the biological activity and/or structure of a polypeptide. Similarly, the residues required for binding to MHC are known, and may be modified to improve binding. However, modifications resulting in decreased binding to MHC will not be appropriate in most situations. One skilled in the art would also know that, even in relatively conserved regions, one may substitute chemically similar amino acids for the naturally occurring residues while retaining activity. Therefore, even areas that may be important for biological activity or for study or may be subject to conservative amino acid substitutions without destroying the biological activity or without adversely affecting the polypeptide structure.

Other preferred polypeptide variants include glycosylation variants wherein the number and/or type of glycosylation sites have been altered compared to the subject amino acid sequence. In one embodiment, polypeptide variants comprise a greater or a lesser number of N-linked glycosylation sites than the subject amino acid sequence. An N-linked glycosylation site is characterized by the sequence Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. To affect O-linked glycosylation of a polypeptide, one would modify serine and/or threonine residues.

Additional preferred variants include cysteine variants, wherein one or more cysteine residues are deleted or substituted with another amino acid (e.g., serine) as compared to the subject amino acid sequence set. Cysteine variants are useful when polypeptides must be refolded into a biologically active conformation such as after the isolation of insoluble inclusion bodies. Cysteine variants generally have fewer cysteine residues than the native protein, and typically have an even number to minimize interactions resulting from unpaired cysteines.

In other embodiments, the isolated polypeptides of the current invention include fusion polypeptide segments that assist in purification of the polypeptides. Fusions can be made either at the amino terminus or at the carboxy terminus of the subject polypeptide variant thereof. Fusions may be direct with no linker or adapter molecule or may be through a linker or adapter molecule. A linker or adapter molecule may be one or more amino acid residues, typically from about 20 to about 50 amino acid residues. A linker or adapter molecule may also be designed with a cleavage site for a DNA restriction endonuclease or for a protease to allow for the separation of the fused moieties. It will be appreciated that once constructed, the fusion polypeptides can be derivatized according to the methods described herein. Suitable fusion segments include, among others, metal binding domains (e.g., a poly-histidine segment), immunoglobulin binding domains (i.e., Protein A, Protein G, T cell, B cell, Fc receptor, or complement protein antibody-binding domains), sugar binding domains (e.g., a maltose binding domain), and/or a "tag" domain (i.e., at least a portion of α-galactosidase, a strep tag peptide, a T7 tag peptide, a FLAG peptide, or other domains that can be purified using compounds that bind to the domain, such as monoclonal antibodies). This tag is typically fused to the polypeptide upon expression of the polypeptide, and can serve as a means for affinity purification of the sequence of interest polypeptide from the host cell. Affinity purification can be accomplished, for example, by column chromatography using antibodies against the tag as an affinity matrix. Optionally, the tag can subsequently be removed from the purified sequence of interest polypeptide by various means such as using certain peptidases for cleavage. As described below, fusions may also be made between a TA and a co-stimulatory components such as the chemokines CXC10 (IP-10), CCL7 (MCP-3), or CCL5 (RANTES), for example.

A fusion motif may enhance transport of an immunogenic target to an MHC processing compartment, such as the endoplasmic reticulum. These sequences, referred to as tranduction or transcytosis sequences, include sequences derived from HIV tat (see Kim et al. 1997J. Immunol. 159:1666), *Drosophila* antennapedia (see Schutze-Redelmeier et al. 1996 J. Immunol. 157:650), or human period-1 protein (hPER1; in particular, SRRHHCRSKAKRSRHH).

In addition, the polypeptide or variant thereof may be fused to a homologous polypeptide to form a homodimer or to a heterologous polypeptide to form a heterodimer. Heterologous peptides and polypeptides include, but are not limited to: an epitope to allow for the detection and/or isolation of a fusion polypeptide; a transmembrane receptor protein or a portion thereof, such as an extracellular domain or a transmembrane and intracellular domain; a ligand or a portion thereof which binds to a transmembrane receptor protein; an enzyme or portion thereof which is catalytically active; a polypeptide or peptide which promotes oligomerization, such as a leucine zipper domain; a polypeptide or peptide which increases stability, such as an immunoglobulin constant region; and a polypeptide which has a therapeutic activity different from the polypeptide or variant thereof.

In certain embodiments, it may be advantageous to combine a nucleic acid sequence encoding an immunogenic target, polypeptide, or derivative thereof with one or more co-stimulatory component(s) such as cell surface proteins, cytokines or chemokines in a composition of the present invention. The co-stimulatory component may be included in the composition as a polypeptide or as a nucleic acid encoding the polypeptide, for example. Suitable co-stimulatory molecules include, for instance, polypeptides that bind members of the CD28 family (i.e., CD28, ICOS; Hutloff, et al. *Nature* 1999, 397: 263-265; Peach, et al. *J Exp Med* 1994, 180: 2049-2058) such as the CD28 binding polypeptides B7.1 (CD80; Schwartz, 1992; Chen et al, 1992; Ellis, et al. *J. Immunol.,* 156(8): 2700-9) and B7.2 (CD86; Ellis, et al. *J. Immunol.,* 156(8): 2700-9); polypeptides which bind members of the integrin family (i.e., LFA-1 (CD11a/CD18); Sedwick, et al. *J Immunol* 1999, 162: 1367-1375; Wülfing, et al. *Science* 1998, 282: 2266-2269; Lub, et al. *Immunol Today* 1995, 16: 479-483) including members of the ICAM family (i.e., ICAM-1, -2 or -3); polypeptides which bind CD2 family members (i.e., CD2, signalling lymphocyte activation molecule (CDw150 or "SLAM"; Aversa, et al. *J Immunol* 1997, 158: 4036-4044)) such as CD58 (LFA-3; CD2 ligand; Davis, et al. *Immunol Today* 1996, 17: 177-187) or SLAM ligands (Sayos, et al. *Nature* 1998, 395: 462-469); polypeptides which bind heat stable antigen (HSA or CD24; Zhou, et al. *Eur J Immunol* 1997, 27: 2524-2528); polypeptides which bind to members of the TNF receptor (TNFR) family (i.e., 4-1BB (CD137; Vinay, et al. *Semin Immunol* 1998, 10: 481-489), OX40 (CD134; Weinberg, et al. *Semin Immunol* 1998, 10: 471-480; Higgins, et al. *J Immunol* 1999, 162: 486-493), and CD27 (Lens, et al. *Semin Immunol* 1998, 10: 491-499)) such as 4-1BBL (4-1BB ligand; Vinay, et al. *Semin Immunol* 1998, 10: 481-48; DeBenedette, et al. *J Immunol* 1997, 158: 551-559), TNFR associated factor-1 (TRAF-1; 4-1BB ligand; Saoulli, et al. *J Exp Med* 1998, 187: 1849-1862, Arch, et al. *Mol Cell Biol* 1998, 18: 558-565), TRAF-2 (4-1BB and OX40 ligand; Saoulli, et al. *J Exp Med* 1998, 187: 1849-1862; Oshima, et al. *Int Immunol* 1998, 10: 517-526, Kawamata, et al. *J Biol Chem* 1998, 273: 5808-5814), TRAF-3 (4-1BB and OX40 ligand; Arch, et al. *Mol Cell Biol* 1998, 18: 558-565; king, et al. *Biochem Biophys Res Commun* 1998, 242: 613-620; Kawamata S, et al. *J Biol Chem* 1998, 273: 5808-5814), OX40L (OX40 ligand; Gramaglia, et al. *J Immunol* 1998, 161: 6510-6517), TRAF-5 (OX40 ligand; Arch, et al. *Mol Cell Biol* 1998, 18: 558-565; Kawamata, et al. *J Biol Chem* 1998, 273: 5808-5814), and bD70 (CD27 ligand; Couderc, et al. *Cancer Gene Ther.,* 5(3): 163-75). CD154 (CD40 ligand or "CD40L"; Gurunathan, et al. *J. Immunol.,* 1998, 161: 4563-4571; Sine, et al. *Hum. Gene Ther.,* 2001, 12: 1091-1102) may also be suitable.

One or more cytokines may also be suitable co-stimulatory components or "adjuvants", either as polypeptides or being encoded by nucleic acids contained within the compositions of the present invention (Parmiani, et al. Immunol Lett 2000 Sep. 15; 74(1): 41-4; Berzofsky, et al. Nature Immunol. 1: 209-219). Suitable cytokines include, for example, interleukin-2 (IL-2) (Rosenberg, et al. *Nature Med.* 4: 321-327 (1998)), IL-4, IL-7, IL-12 (reviewed by Pardoll, 1992; Harries, et al. J. Gene Med. 2000 July-August; 2(4):243-9; Rao, et al. *J. Immunol.* 156: 3357-3365 (1996)), IL-15 (Xin, et al. *Vaccine,* 17:858-866, 1999), IL-16 (Cruikshank, et al. J. Leuk Biol. 67(6): 757-66, 2000), IL-18 (*J. Cancer Res. Clin. Oncol.* 2001. 127(12): 718-726), GM-CSF (CSF (Disis, et al. *Blood,* 88: 202-210 (1996)), tumor necrosis factor-alpha (TNF-α), or interferon-gamma (INF-γ). Other cytokines may also be suitable for practicing the present invention, as is known in the art.

Chemokines may also be utilized. For example, fusion proteins comprising CXCL10 (IP-10) and CCL7 (MCP-3) fused to a tumor self-antigen have been shown to induce anti-tumor immunity (Biragyn, et al. *Nature Biotech.* 1999, 17: 253-258). The chemokines CCL3 (MIP-1α) and CCL5 (RANTES) (Boyer, et al. *Vaccine,* 1999, 17 (Supp. 2): S53-S64) may also be of use in practicing the present invention. Other suitable chemokines are known in the art.

It is also known in the art that suppressive or negative regulatory immune mechanisms may be blocked, resulting in enhanced immune responses. For instance, treatment with anti-CTLA-4 (Shrikant, et al. *Immunity,* 1996, 14: 145-155; Sutmuller, et al. *J. Exp. Med.,* 2001, 194: 823-832), anti-CD25 (Sutmuller, supra), anti-CD4 (Matsui, et al. *J. Immunol.,* 1999, 163: 184-193), the fusion protein IL13Ra2-Fc (Terabe, et al. *Nature Immunol.,* 2000, 1: 515-520), and combinations thereof (i.e., anti-CTLA-4 and anti-CD25, Sutmuller, supra) have been shown to upregulate anti-tumor immune responses and would be suitable in practicing the present invention.

Any of these components may be used alone or in combination with other agents. For instance, it has been shown that a combination of CD80, ICAM-1 and LFA-3 ("TRICOM") may potentiate anti-cancer immune responses (Hodge, et al. *Cancer Res.* 59: 5800-5807 (1999). Other effective combinations include, for example, IL-12+GM-CSF (Ahlers, et al. *J. Immunol*., 158: 3947-3958 (1997); Iwasaki, et al. *J. Immunol.* 158: 4591-4601 (1997)), IL-12+GM-CSF+TNF-α (Ahlers, et al. *Int. Immunol.* 13: 897-908 (2001)), CD80+IL-12 (Fruend, et al. *Int. J. Cancer,* 85: 508-517 (2000); Rao, et al. supra), and CD86+GM-CSF+IL-12 (Iwasaki, supra). One of skill in the art would be aware of additional combinations useful in carrying out the present invention. In addition, the skilled artisan would be aware of additional reagents or methods that may be used to modulate such mechanisms. These reagents and methods, as well as others known by those of skill in the art, may be utilized in practicing the present invention.

Additional strategies for improving the efficiency of nucleic acid-based immunization may also be used including, for example, the use of self-replicating viral replicons (Caley, et al. 1999. *Vaccine,* 17: 3124-2135; Dubensky, et al. 2000. *Mol. Med.* 6: 723-732; Leitner, et al. 2000. *Cancer Res.* 60: 51-55), codon optimization (Liu, et al. 2000. *Mol. Ther.,* 1: 497-500; Dubensky, supra; Huang, et al. 2001. *J. Virol.* 75: 4947-4951), in vivo electroporation (Widera, et al. 2000. *J. Immunol.* 164: 4635-3640), incorporation of CpG stimulatory motifs (Gurunathan, et al. *Ann. Rev. Immunol.,* 2000, 18: 927-974; Leitner, supra), sequences for targeting of the endocytic or ubiquitin-processing pathways (Thomson, et al. 1998. *J. Virol.* 72: 2246-2252; Velders, et al. 2001. *J. Immunol.* 166: 5366-5373), prime-boost regimens (Gurunathan, supra; Sullivan, et al. 2000. *Nature,* 408: 605-609; Hanke, et al. 1998. *Vaccine,* 16: 439-445; Amara, et al. 2001. *Science,* 292: 69-74), and the use of mucosal delivery vectors such as *Salmonella* (Darji, et al. 1997. *Cell,* 91: 765-775; Woo, et al. 2001. *Vaccine,* 19: 2945-2954). Other methods are known in the art, some of which are described below.

Chemotherapeutic agents, radiation, anti-angiogenic compounds, or other agents may also be utilized in treating and/or preventing cancer using immunogenic targets (Sebti, et al. *Oncogene* 2000 Dec. 27; 19(56):6566-73). For example, in treating metastatic breast cancer, useful chemotherapeutic agents include cyclophosphamide, doxorubicin, paclitaxel, docetaxel, navelbine, capecitabine, and mitomycin C, among others. Combination chemotherapeutic regimens have also proven effective including cyclophosphamide+methotrexate+5-fluorouracil; cyclophosphamide+doxorubicin+5-fluorouracil; or, cyclophosphamide+doxorubicin, for example. Other compounds such as prednisone, a taxane, navelbine, mitomycin C, or vinblastine have been utlized for various reasons. A majority of breast cancer patients have estrogen-receptor positive (ER+) tumors and in these patients, endocrine therapy (i.e., tamoxifen) is preferred over chemotherapy. For such patients, tamoxifen or, as a second line therapy, progestins (medroxyprogesterone acetate or megestrol acetate) are preferred. Aromatase inhibitors (i.e., aminoglutethimide and analogs thereof such as letrozole) decrease the availability of estrogen needed to maintain tumor growth and may be used as second or third line endocrine therapy in certain patients.

Other cancers may require different chemotherapeutic regimens. For example, metastatic colorectal cancer is typically treated with Camptosar (irinotecan or CPT-11), 5-fluorouracil or leucovorin, alone or in combination with one another. Proteinase and integrin inhibitors such as as the MMP inhibitors marimastate (British Biotech), COL-3 (Collagenex), Neovastat (Aeterna), AG3340 (Agouron), BMS-275291 (Bristol Myers Squibb), CGS 27023A (Novartis) or the integrin inhibitors Vitaxin (Medimmune), or MED1522 (Merck KgaA) may also be suitable for use. As such, immunological targeting of immunogenic targets associated with colorectal cancer could be performed in combination with a treatment using those chemotherapeutic agents. Similarly, chemotherapeutic agents used to treat other types of cancers are well-known in the art and may be combined with the immunogenic targets described herein.

Many anti-angiogenic agents are known in the art and would be suitable for co-administration with the immunogenic target vaccines (see, for example, Timar, et al. 2001. *Pathology Oncol. Res.,* 7(2): 85-94). Such agents include, for example, physiological agents such as growth factors (i.e., ANG-2, NK1,2,4 (HGF), transforming growth factor beta (TGF-β)), cytokines (i.e., interferons such as IFN-α, -β, -γ, platelet factor 4 (PF-4), PR-39), proteases (i.e., cleaved AT-III, collagen XVIII fragment (Endostatin)), HmwKallikrein-d5 plasmin fragment (Angiostatin), prothrombin-F1-2, TSP-1), protease inhibitors (i.e., tissue inhibitor of metalloproteases such as TIMP-1, -2, or -3; maspin; plasminogen activator-inhibitors such as PM-1; pigment epithelium derived factor (PEDF)), Tumstatin (available through ILEX, Inc.), antibody products (i.e., the collagen-binding antibodies HUIV26, HUI77, XL313; anti-VEGF; anti-integrin (i.e., Vitaxin, (Lxsys))), and glycosidases (i.e., heparinase-I, -III).

"Chemical" or modified physiological agents known or believed to have anti-angiogenic potential include, for example, vinblastine, taxol, ketoconazole, thalidomide, dolestatin, combrestatin A, rapamycin (Guba, et al. 2002, *Nature Med.,* 8: 128-135), CEP-7055 (available from Cephalon, Inc.), flavone acetic acid, Bay 12-9566 (Bayer Corp.), AG3340 (Agouron, Inc.), CGS 27023A (Novartis), tetracylcine derivatives (i.e., COL-3 (Collagenix, Inc.)), Neovastat (Aeterna), BMS-275291 (Bristol-Myers Squibb), low dose 5-FU, low dose methotrexate (MTX), irsofladine, radicicol, cyclosporine, captopril, celecoxib, D45152-sulphated polysaccharide, cationic protein (Protamine), cationic peptide-VEGF, Suramin (polysulphonated napthyl urea), compounds that interfere with the function or production of VEGF (i.e., SU5416 or SU6668 (Sugen), PTK787/ZK22584 (Novartis)), Distamycin A, Angiozyme (ribozyme), isoflavinoids, staurosporine derivatives, genistein, EMD121974 (Merck KcgaA), tyrphostins, isoquinolones, retinoic acid, carboxyamidotriazole, TNP-470, octreotide 2-niethoxyestradiol, aminosterols (i.e., squalamine), glutathione analogues (i.e., N-acteyl-L-cysteine), combretastatin A-4 (Oxigene), Eph receptor blocking agents (*Nature,* 414:933-938, 2001), Rh-Angiostatin, Rh-Endostatin (WO 01/93897), cyclic-RGD peptide, accutin-disintegrin, benzodiazepenes, humanized anti-avb3 Ab, Rh-PAI-2, amiloride, p-amidobenzamidine, anti-uPA ab, anti-uPAR Ab, L-phanylalanin-N-methylamides (i.e., Batimistat, Marimastat), AG3340, and minocycline. Many other suitable agents are known in the art and would suffice in practicing the present invention.

The present invention may also be utilized in combination with "non-traditional" methods of treating cancer. For example, it has recently been demonstrated that administration of certain anaerobic bacteria may assist in slowing tumor growth. In one study, *Clostridium novyi* was modified to eliminate a toxin gene carried on a phage episome and administered to mice with colorectal tumors (Dang, et al. *P.N.A.S. USA,* 98(26): 15155-15160, 2001). In combination with chemotherapy, the treatment was shown to cause tumor necrosis in the animals. The reagents and methodologies described in this application may be combined with such treatment methodologies.

Nucleic acids encoding immunogenic targets may be administered to patients by any of several available techniques. Various viral vectors that have been successfully utilized for introducing a nucleic acid to a host include retrovirus, adenovirus, adeno-associated virus (AAV), herpes virus, and poxvirus, among others. It is understood in the art that many such viral vectors are available in the art. The vectors of the present invention may be constructed using standard recombinant techniques widely available to one skilled in the art. Such techniques may be found in common molecular biology references such as *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), and *PCR Protocols: A Guide to Methods and Applications*(Innis, et al. 1990. Academic Press, San Diego, Calif.).

Preferred retroviral vectors are derivatives of lentivirus as well as derivatives of murine or avian retroviruses. Examples of suitable retroviral vectors include, for example, Moloney murine leukemia virus (MoMuLV), Harvey murine sarcoma virus (HaMuSV), murine mammary tumor virus (MuMTV), SW, BIV, HIV and Rous Sarcoma Virus (RSV). A number of retroviral vectors can incorporate multiple exogenous nucleic acid sequences. As recombinant retroviruses are defective, they require assistance in order to produce infectious vector particles. This assistance can be provided by, for example, helper cell lines encoding retrovirus structural genes. Suitable helper cell lines include Ψ2, PA317 and PA12, among others. The vector virions produced using such cell lines may then be used to infect a tissue cell line, such as NIH 3T3 cells, to produce large quantities of chimeric retroviral virions. Retroviral vectors may be administered by traditional methods (i.e., injection) or by implantation of a "producer-cell line" in proximity to the target cell population (Culver, K., et al., 1994, *Hum. Gene Ther.,* 5 (3): 343-79; Culver, K., et al., *Cold Spring Harb. Symp. Quant. Biol.,* 59: 685-90); Oldfield, E., 1993, *Hum. Gene Ther.,* 4 (1): 39-69). The producer cell line is engineered to produce a viral vector and releases viral particles in the vicinity of the target cell. A portion of the released viral particles contact the target cells and infect those cells, thus delivering a nucleic acid of the present invention to the target cell. Following infection of the target cell, expression of the nucleic acid of the vector occurs.

Adenoviral vectors have proven especially useful for gene transfer into eukaryotic cells (Rosenfeld, M., et al., 1991, *Science,* 252 (5004): 431-4; Crystal, R., et al., 1994, *Nat: Genet.,* 8 (1): 42-51), the study eukaryotic gene expression (Levrero, M., et al., 1991, *Gene,* 101 (2): 195-202), vaccine development (Graham, F. and Prevec, L., 1992, *Biotechnology,* 20: 363-90), and in animal models (Stratford-Perricaudet, L., et al., 1992, *Bone Marrow Transplant.,* 9 (Suppl. 1): 151-2; Rich, D., et al., 1993, *Hum. Gene Ther.,* 4 (4): 461-76). Experimental routes for administrating recombinant Ad to different tissues in vivo have included intratracheal instillation (Rosenfeld, M., et al., 1992, *Cell,* 68 (1): 143-55) injection into muscle (Quantin, B., et al., 1992, *Proc. Natl. Acad. Sci. U.S.A.,* 89 (7): 2581-4), peripheral intravenous injection (Herz, J., and Gerard, R., 1993, *Proc. Natl. Acad. Sci. U.S.A.,* 90 (7): 2812-6) and stereotactic inoculation to brain (Le Gal La Salle, G., et al., 1993, *Science,* 259 (5097): 988-90), among others.

Adeno-associated virus (AAV) demonstrates high-level infectivity, broad host range and specificity in integrating into the host cell genome (Hermonat, P., et al., 1984, *Proc. Natl. Acad. Sci. U.S.A.,* 81 (20): 6466-70). And Herpes Simplex Virus type-1 (HSV-1) is yet another attractive vector system, especially for use in the nervous system because of its neurotropic property (Geller, A., et al., 1991, *Trends Neurosci.,* 14 (10): 428-32; Glorioso, et al., 1995, *Mol. Biotechnol,* 4 (1): 87-99; Glorioso, et al., 1995, *Annu. Rev. Microbiol.,* 49: 675-710).

Poxvirus is another useful expression vector (Smith, et al. 1983, *Gene,* 25 (1): 21-8; Moss, et al, 1992, *Biotechnology,* 20: 345-62: Moss, et al, 1992, *Curr. Top. Microbiol. Immunol.,* 158: 25-38; Moss, et al. 1991. Science, 252: 1662-1667). Poxviruses shown to be useful include vaccinia, NYVAC, avipox, fowlpox, canarypox, ALVAC, and ALVAC(2), among others.

Vaccinia virus is the prototypic virus of the pox virus family and, like other members of the pox virus group, is distinguished by its large size and complexity. The DNA of vaccinia virus is similarly large and complex. Several types of vaccinia are suitable for use in practicing the present invention. One such vaccinia-related virus is the Modified Vaccinia Virus Ankara (MVA), as described in, for example, U.S. Pat. Nos. 5,185,146 and 6,440,422.

Another suitable vaccinia-related virus is NYVAC. NYVAC was derived from the Copenhagen vaccine strain of vaccinia virus by deleting six nonessential regions of the genome encoding known or potential virulence factors (see, for example, U.S. Pat. Nos. 5,364,773 and 5,494,807). The deletion loci were also engineered as recipient loci for the insertion of foreign genes. The deleted regions are: thymidine kinase gene (TK; J2R); hemorrhagic region (u; B13R+B 14R); A type inclusion body region (ATI; A26L); hemagglutinin gene (HA; A56R); host range gene region (C7L-K1L); and, large subunit, ribonucleotide reductase (I4L). NYVAC is a genetically engineered vaccinia virus strain that was generated by the specific deletion of eighteen open reading frames encoding gene products associated with virulence and host range. NYVAC has been show to be useful for expressing TAs (see, for example, U.S. Pat. No. 6,265,189). NYVAC (vP866), vP994, vCP205, vCP1433, placZH6H4Lreverse, pMPC6H6K3E3 and $pC3H_6FHVB$ were also deposited with the ATCC under the terms of the Budapest Treaty, accession numbers VR-2559, VR-2558, VR-2557, VR-2556, ATCC-97913, ATCC-97912, and ATCC-97914, respectively.

ALVAC-based recombinant viruses (i.e., ALVAC-1 and ALVAC-2) are also suitable for use in practicing the present invention (see, for example, U.S. Pat. No. 5,756,103). ALVAC(2) is identical to ALVAC(1) except that ALVAC(2) genome comprises the vaccinia E3L and K3L genes under the control of vaccinia promoters (U.S. Pat. No. 6,130,066; Beattie et al., 1995a, 1995b, 1991; Chang et al., 1992; Davies et al., 1993). Both ALVAC(1) and ALVAC(2) have been demonstrated to be useful in expressing foreign DNA sequences, such as TAs (Tartaglia et al., 1993 a,b; U.S. Pat. No. 5,833,975). ALVAC was deposited under the terms of the Budapest Treaty with the American Type Culture Collection (ATCC), 10801 University Boulevard, Manassas, Va. 20110-2209, USA, ATCC accession number VR-2547.

Another useful poxvirus vector is TROVAC. TROVAC refers to an attenuated fowlpox that was a plaque-cloned isolated derived from the FP-1 vaccine strain of fowlpoxvirus which is licensed for vaccination of 1 day old chicks. TROVAC was likewise deposited under the terms of the Budapest Treaty with the ATCC, accession number 2553.

"Non-viral" plasmid vectors may also be suitable in practicing the present invention. Preferred plasmid vectors are compatible with bacterial, insect, and/or mammalian host cells. Such vectors include, for example, PCR-II, pCR3, and pcDNA3.1 (Invitrogen, San Diego, Calif.), pBSII (Stratagene, La Jolla, Calif.), pET15 (Novagen, Madison, Wis.), pGEX (Pharmacia Biotech, Piscataway, N.J.), pEGFP-N2 (Clontech, Palo Alto, Calif.), pETL (BlueBacII, Invitrogen), pDSR-alpha (PCT pub. No. WO 90/14363) and pFastBacDual (Gibco-BRL, Grand Island, N.Y.) as well as Bluescript® plasmid derivatives (a high copy number COLE1-based phagemid, Stratagene Cloning Systems, La Jolla, Calif.), PCR cloning plasmids designed for cloning Taq-amplified PCR products (e.g., TOPO™ TA Cloning® kit, PCR2.1® plasmid derivatives, Invitrogen, Carlsbad, Calif.). Bacterial vectors may also be used with the current invention. These vectors include, for example, *Shigella, Salmonella, Vibrio cholerae, Lactobacillus, Bacille calmette guerin* (BCG), and *Streptococcus* (see for example, WO 88/6626; WO 90/0594; WO 91/13157; WO 92/1796; and WO 92/21376). Many other non-viral plasmid expression vectors and systems are known in the art and could be used with the current invention.

Suitable nucleic acid delivery techniques include DNA-ligand complexes, adenovirus-ligand-DNA complexes, direct injection of DNA, $CaPO_4$ precipitation, gene gun techniques, electroporation, and colloidal dispersion systems, among others. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome, which are artificial membrane vesicles useful as delivery vehicles in vitro and in vivo. RNA, DNA and intact virions can be encapsulated within the aqueous interior and be delivered to cells in a biologically active form (Fraley, R., et al., 1981, *Trends Biochem. Sci.,* 6: 77). The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phoshiatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

An immunogenic target may also be administered in combination with one or more adjuvants to boost the immune response. Exemplary adjuvants are shown in Table I below:

TABLE I

Types of Immunologic Adjuvants

| | Type of Adjuvant | General Examples | Specific Examples/References |
|---|---|---|---|
| 1 | Gel-type | Aluminum hydroxide/phosphate ("alum adjuvants") | (Aggerbeck and Heron, 1995) |
| | | Calcium phosphate | (Relyveld, 1986) |
| 2 | Microbial | Muramyl dipeptide (MDP) | (Chedid et al., 1986) |
| | | Bacterial exotoxins | Cholera toxin (CT), *E. coli* labile toxin (LT)(Freytag and Clements, 1999) |
| | | Endotoxin-based adjuvants | Monophosphoryl lipid A (MPL) (Ulrich and Myers, 1995) |
| | | Other bacterial | CpG oligonucleotides (Corral and Petray, 2000), BCG sequences (Krieg, et al. Nature, 374:576), tetanus toxoid (Rice, et al. J. Immunol., 2001, 167: 1558-1565) |
| 3 | Particulate | Biodegradable polymer microspheres | (Gupta et al., 1998) |
| | | Immunostimulatory complexes (ISCOMs) | (Morein and Bengtsson, 1999) |
| | | Liposomes | (Wassef et al., 1994) |

TABLE I-continued

Types of Immunologic Adjuvants

| | Type of Adjuvant | General Examples | Specific Examples/References |
|---|---|---|---|
| 4 | Oil-emulsion and surfactant-based adjuvants | Freund's incomplete adjuvant | (Jensen et al., 1998) |
| | | Microfluidized emulsions | MF59 (Ott et al., 1995)<br>SAF (Allison and Byars, 1992)<br>(Allison, 1999) |
| | | Saponins | QS-21 (Kensil, 1996) |
| 5 | Synthetic | Muramyl peptide derivatives | Murabutide (Lederer, 1986)<br>Threony-MDP (Allison, 1997) |
| | | Nonionic block copolymers | L121 (Allison, 1999) |
| | | Polyphosphazene (PCPP) | (Payne et al., 1995) |
| | | Synthetic polynucleotides | Poly A:U, Poly I:C (Johnson, 1994) |

The immunogenic targets of the present invention may also be used to generate antibodies for use in screening assays or for immunotherapy. Other uses would be apparent to one of skill in the art. The term "antibody" includes antibody fragments, as are known in the art, including Fab, $Fab_2$, single chain antibodies (FV for example), humanized antibodies, chimeric antibodies, human antibodies, produced by several methods as are known in the art. Methods of preparing and utilizing various types of antibodies are well-known to those of skill in the art and would be suitable in practicing the present invention (see, for example, Harlow, et al. *Antibodies: A Laboratory Manual*, Cold Spring Harbor Laboratory, 1988; Harlow, et al. *Using Antibodies: A Laboratory Manual*, Portable Protocol No. 1, 1998; Kohler and Milstein, Nature, 256:495 (1975)); Jones et al. *Nature,* 321:522-525 (1986); Riechmann et al. Nature, 332:323-329 (1988); Presta (Curr. Op. Struct. Biol., 2:593-596 (1992); Verhoeyen et al. (*Science,* 239:1534-1536 (1988); Hoogenboom et al., J. Mol. Biol., 227:381 (1991); Marks et al., *J. Mol. Biol.,* 222:581 (1991); Cole et al., Monoclonal Antibodies and Cancer Therapy, Alan R. Liss, p. 77 (1985); Boerner et al., J. Immunol., 147(1):86-95 (1991); Marks et al., *Bio/Technology* 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995); as well as U.S. Pat. Nos. 4,816,567; 5,545,807; 5,545,806; 5,569,825; 5,625,126; 5,633,425; and, 5,661,016). The antibodies or derivatives therefrom may also be conjugated to therapeutic moieties such as cytotoxic drugs or toxins, or active fragments thereof such as diptheria A chain, exotoxin A chain, ricin A chain, abrin A chain, curcin, crotin, phenomycin, enomycin, among others. Cytotoxic agents may also include radiochemicals. Antibodies and their derivatives may be incorporated into compositions of the invention for use in vitro or in vivo.

Nucleic acids, proteins, or derivatives thereof representing an immunogenic target may be used in assays to determine the presence of a disease state in a patient, to predict prognosis, or to determine the effectiveness of a chemotherapeutic or other treatment regimen. Expression profiles, performed as is known in the art, may be used to determine the relative level of expression of the immunogenic target. The level of expression may then be correlated with base levels to determine whether a particular disease is present within the patient, the patient's prognosis, or whether a particular treatment regimen is effective. For example, if the patient is being treated with a particular chemotherapeutic regimen, an decreased level of expression of an immunogenic target in the patient's tissues (i.e., in peripheral blood) may indicate the regimen is decreasing the cancer load in that host. Similarly, if the level of expresssion is increasing, another therapeutic modality may need to be utilized. In one embodiment, nucleic acid probes corresponding to a nucleic acid encoding an immunogenic target may be attached to a biochip, as is known in the art, for the detection and quantification of expression in the host.

It is also possible to use nucleic acids, proteins, derivatives therefrom, or antibodies thereto as reagents in drug screening assays. The reagents may be used to ascertain the effect of a drug candidate on the expression of the immunogenic target in a cell line, or a cell or tissue of a patient. The expression profiling technique may be combined with high throughput screening techniques to allow rapid identification of useful compounds and monitor the effectiveness of treatment with a drug candidate (see, for example, Zlokarnik, et al., Science 279, 84-8 (1998)). Drug candidates may be chemical compounds, nucleic acids, proteins, antibodies, or derivatives therefrom, whether naturally occurring or synthetically derived. Drug candidates thus identified may be utilized, among other uses, as pharmaceutical compositions for administration to patients or for use in further screening assays.

Administration of a composition of the present invention to a host may be accomplished using any of a variety of techniques known to those of skill in the art. The composition(s) may be processed in accordance with conventional methods of pharmacy to produce medicinal agents for administration to patients, including humans and other mammals (i.e., a "pharmaceutical composition"). The pharmaceutical composition is preferably made in the form of a dosage unit containing a given amount of DNA, viral vector particles, polypeptide or peptide, for example. A suitable daily dose for a human or other mammal may vary widely depending on the condition of the patient and other factors, but, once again, can be determined using routine methods.

The pharmaceutical composition may be administered orally, parentally, by inhalation spray, rectally, intranodally, or topically in dosage unit formulations containing conventional pharmaceutically acceptable carriers, adjuvants, and vehicles. The term "pharmaceutically acceptable carrier" or "physiologically acceptable carrier" as used herein refers to one or more formulation materials suitable, for accomplishing or enhancing the delivery of a nucleic acid, polypeptide, or peptide as a pharmaceutical composition. A "pharmaceutical composition" is a composition comprising a therapeutically effective amount of a nucleic acid or polypeptide. The terms "effective amount" and "therapeutically effective amount" each refer to the amount of a nucleic acid or polypeptide used to induce or enhance an effective immune response. It is preferred that compositions of the present invention provide for the induction or enhancement of an anti-tumor immune response in a host which protects the host from the development of a tumor and/or allows the host to eliminate an existing tumor from the body.

For oral administration, the pharmaceutical composition may be of any of several forms including, for example, a capsule, a tablet, a suspension, or liquid, among others. Liquids may be administered by injection as a composition with suitable carriers including saline, dextrose, or water. The term parenteral as used herein includes subcutaneous, intravenous, intramuscular, intrasternal, infusion, or intraperitoneal administration. Suppositories for rectal administration of the drug can be prepared by mixing the drug with a suitable non-irritating excipient such as cocoa butter and polyethylene glycols that are solid at ordinary temperatures but liquid at the rectal temperature.

The dosage regimen for immunizing a host or otherwise treating a disorder or a disease with a composition of this invention is based on a variety of factors, including the type of disease, the age, weight, sex, medical condition of the patient, the severity of the condition, the route of administration, and the particular compound employed. For example, a poxyiral vector may be administered as a composition comprising $1\times10^6$ infectious particles per dose. Thus, the dosage regimen may vary widely, but can be determined routinely using standard methods.

A prime-boost regimen may also be utilized (WO 01/30382 A1) in which the targeted immunogen is initially administered in a priming step in one form followed by a boosting step in which the targeted immunogen is administered in another form. The form of the targeted immunogen in the priming and boosting steps are different. For instance, if the priming step utilized a nucleic acid, the boost may be administered as a peptide. Similarly, where a priming step utilized one type of recombinant virus (i.e., ALVAC), the boost step may utilize another type of virus (i.e., NYVAC). This prime-boost method of administration has been shown to induce strong immunological responses.

While the compositions of the invention can be administered as the sole active pharmaceutical agent, they can also be used in combination with one or more other compositions or agents (i.e., other immunogenic targets, co-stimulatory molecules, adjuvants). When administered as a combination, the individual components can be formulated as separate compositions administered at the same time or different times, or the components can be combined as a single composition.

Injectable preparations, such as sterile injectable aqueous or oleaginous suspensions, may be formulated according to known methods using suitable dispersing or wetting agents and suspending agents. The injectable preparation may also be a sterile injectable solution or suspension in a non-toxic parenterally acceptable diluent or solvent. Suitable vehicles and solvents that may be employed are water, Ringer's solution, and isotonic sodium chloride solution, among others. For instance, a viral vector such as a poxvirus may be prepared in 0.4% NaCl. In addition, sterile, fixed oils are conventionally employed as a solvent or suspending medium. For this purpose, any bland fixed oil may be employed, including synthetic mono- or diglycerides. In addition, fatty acids such as oleic acid find use in the preparation of injectables.

For topical administration, a suitable topical dose of a composition may be administered one to four, and preferably two or three times daily. The dose may also be administered with intervening days during which no does is applied. Suitable compositions may comprise from 0.001% to 10% w/w, for example, from 1% to 2% by weight of the formulation, although it may comprise as much as 10% w/w, but preferably not more than 5% w/w, and more preferably from 0.1% to 1% of the formulation. Formulations suitable for topical administration include liquid or semi-liquid preparations suitable for penetration through the skin (e.g., liniments, lotions, ointments, creams, or pastes) and drops suitable for administration to the eye, ear, or nose.

The pharmaceutical compositions may also be prepared in a solid form (including granules, powders or suppositories). The pharmaceutical compositions may be subjected to conventional pharmaceutical operations such as sterilization and/or may contain conventional adjuvants, such as preservatives, stabilizers, wetting agents, emulsifiers, buffers etc. Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings. Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting sweetening, flavoring, and perfuming agents.

Pharmaceutical compositions comprising a nucleic acid or polypeptide of the present invention may take any of several forms and may be administered by any of several routes. In preferred embodiments, the compositions are administered via a parenteral route (intradermal, intramuscular or subcutaneous) to induce an immune response in the host.

Alternatively, the composition may be administered directly into a lymph node (intranodal) or tumor mass (i.e., intratumoral administration). For example, the dose could be administered subcutaneously at days 0, 7, and 14. Suitable methods for immunization using compositions comprising TAs are known in the art, as shown for p53 (Hollstein et al., 1991), p21-ras (Almoguera et al., 1988), HER-2 (Fendly et al., 1990), the melanoma-associated antigens (MAGE-1; MAGE-2) (van der Bruggen et al., 1991), p97 (Hu et al., 1988), and carcinoembryonic antigen (CEA) (Kantor et al., 1993; Fishbein et al., 1992; Kaufman et al., 1991), among others.

Preferred embodiments of administratable compositions include, for example, nucleic acids or polypeptides in liquid preparations such as suspensions, syrups, or elixirs. Preferred injectable preparations include, for example, nucleic acids or polypeptides suitable for parental, subcutaneous, intradermal, intramuscular or intravenous administration such as sterile suspensions or emulsions. For example, a recombinant poxvirus may be in admixture with a suitable carrier, diluent, or excipient such as sterile water, physiological saline, glucose or the like. The composition may also be provided in lyophilized form for reconstituting, for instance, in isotonic aqueous, saline buffer. In addition, the compositions can be co-administered or sequentially administered with other anti-neoplastic, anti-tumor or anti-cancer agents and/or with agents which reduce or alleviate ill effects of antineoplastic, anti-tumor or anti-cancer agents.

A kit comprising a composition of the present invention is also provided. The kit can include a separate container containing a suitable carrier, diluent or excipient. The kit can also include an additional anti-cancer, anti-tumor or antineoplastic agent and/or an agent that reduces or alleviates ill effects of antineoplastic, anti-tumor or anti-cancer agents for co- or sequential-administration. Additionally, the kit can include instructions for mixing or combining ingredients and/or administration.

A better understanding of the present invention and of its many advantages will be had from the following examples, given by way of illustration.

EXAMPLES

Example 1

A. Modification of mCEA (6D) Repeat 1

The presence of truncated forms of CEA in cells following expression of recombinant CEA has been documented. This study set forth to generate CEA-encoding nucleic acid sequences that do not result in the expression of truncated CEA following expression in cells. Generation and expression of a new CEA-encoding nucleic acid sequence, CAP (6D)-1,2, is described below.

The plasmid p3'H6MCEA was obtained from Virogenetics, Inc. This plasmid contains the MCEA gene with 6D modification under the control of partial H6 promoter (FIG. 1A; SEQ ID NO.: 1). The 912 bp NruI-BamHI fragment from p3'H6MCEA was cloned into pUC18 to form plasmid pSE1544.9 (pUC18-mCEA repeat 1; FIG. 1B).

Figure 3:
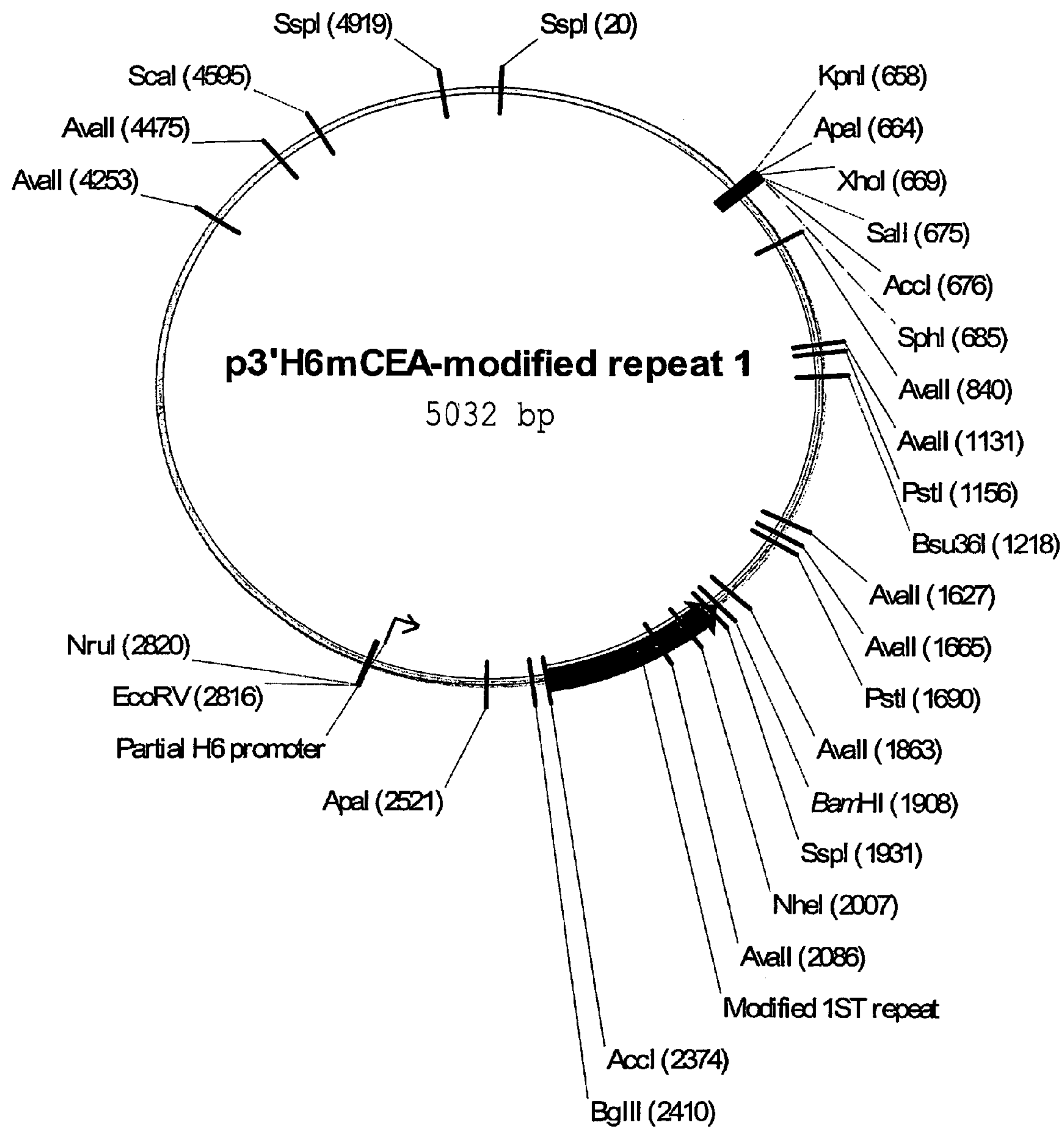
FIG. 3. Illustration of plasmid pSE1658.15 (p3'H6MCEA-modified repeat 1).

OPC purified Oligos 7524-7526, 7528-7533, 7535-7537, and 7567-7568 were kinased and annealed to create two fragments which were ligated to result in a 464 bp synthetic modified mCEA repeat 1 flanked by AccI and BamHI sites. This synthetic modified repeat 1 fragment was cloned into pSE1544.9 AccI-BamHI to create pSE1616.44 (pUC18-mCEA-modified repeat 1; FIG. 2). The 904 bp EcoRV-BamHI fragment of pSE1616.44 was cloned back into p3'H6MCEA EcoRV-BamHI to form pSE1658.15 (p3'H6MCEA-modified repeat 1; FIG. 3).

B. Modification of mCEA(6D) Repeat 2

Figure 4:
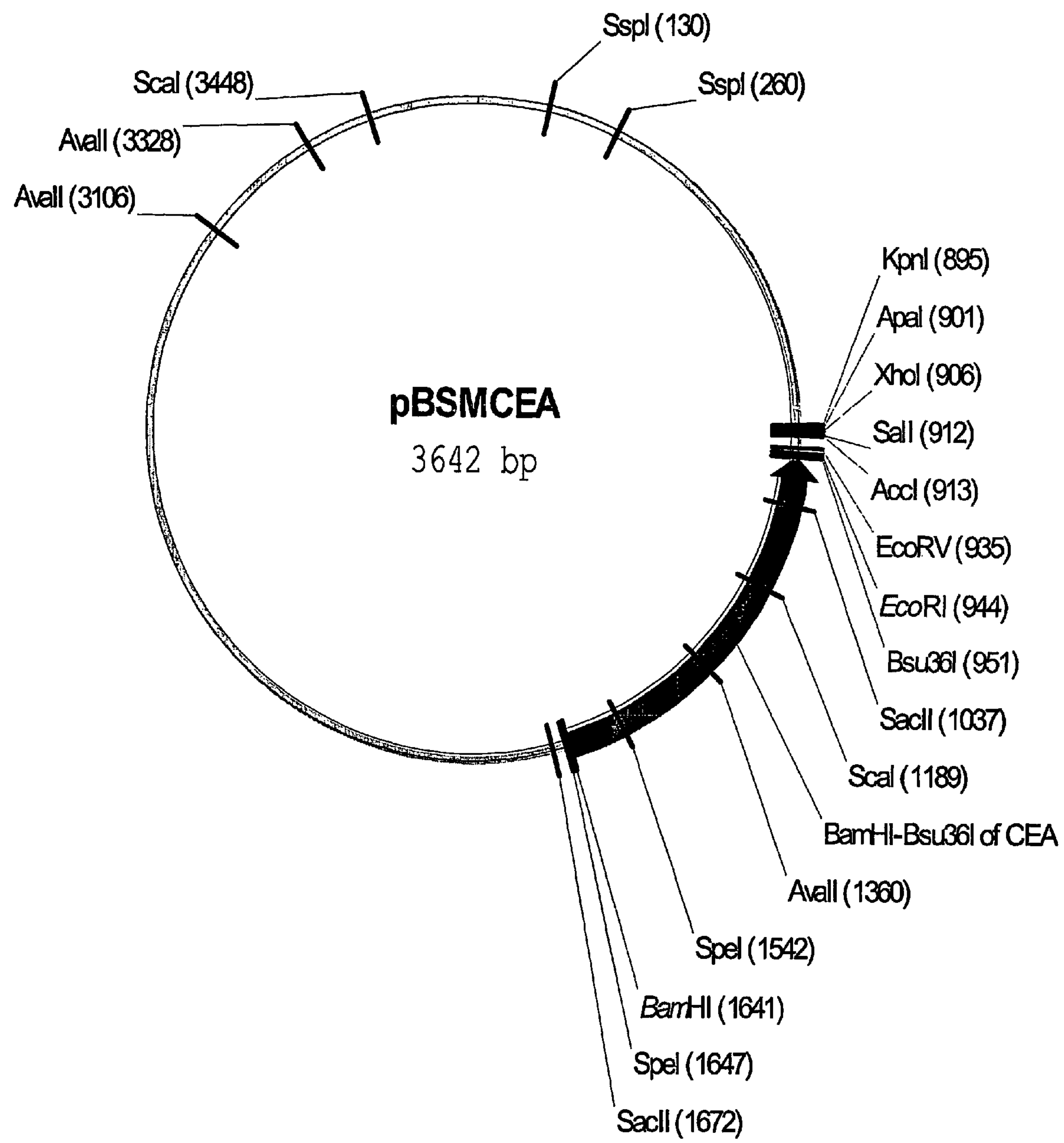
FIG. 4. Illustration of plasmid pBSmCEA.

A synthetic modified repeat 2 fragment was created by using a method called gene splicing by overlap extension (SOE) and cloned into pBluescript-SK+, generating pBSm-CEA (FIG. 4). The oligos used for the repeat 2 modification are shown below (section IV, B). The two different clones (pBS-mCEA-3 and pBS-mCEA-8) contained various point mutations.

Figure 5:
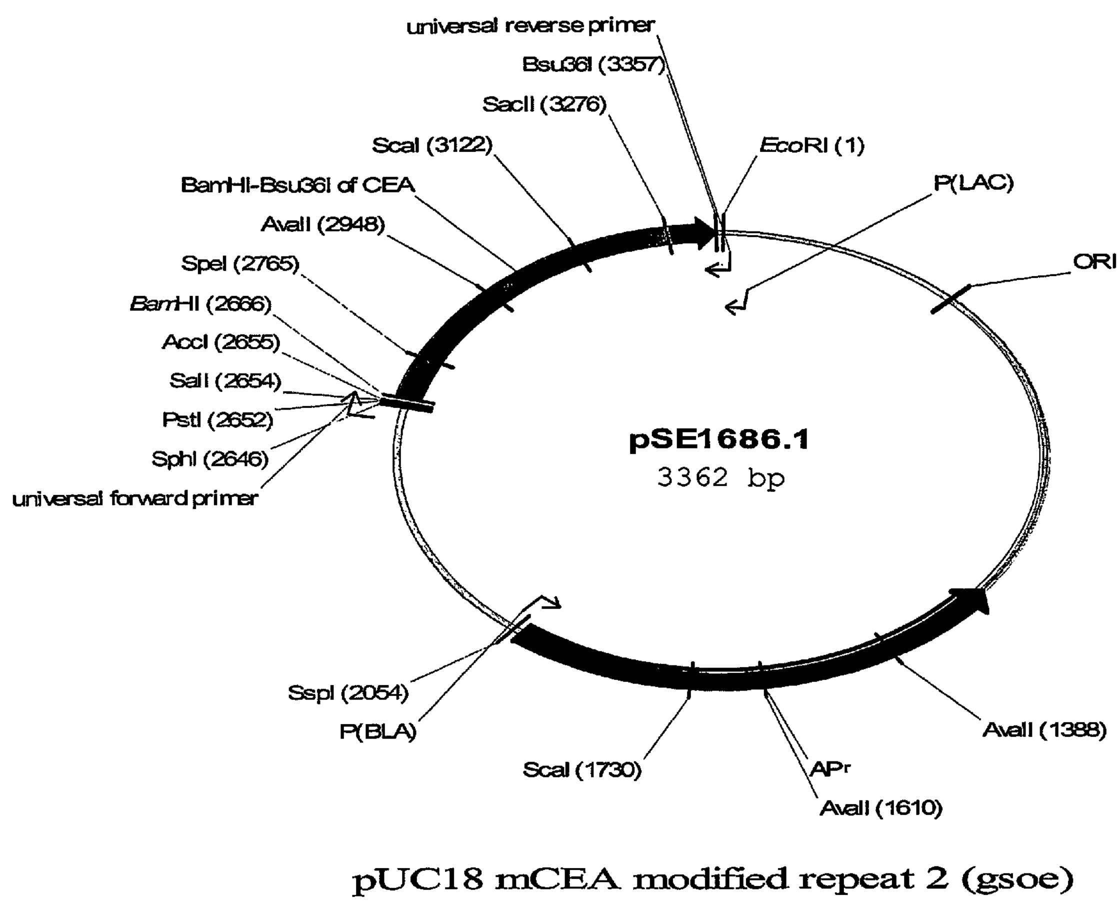
FIG. 5. Illustration of plasmid pSE1686.1 (pUC18 mCEA modified repeat 2.

The 697 bp BamHI-EcoRI fragment of pBS-mCEA-3 was cloned into pUC18 BamHI-EcoRI to create pSE1671.8. The 591 bp SpeI-Bsu36I fragment of pBS mCEA-8 was cloned into pSE1671.8 SpeI-Bsu36I, generating plasmid designated pSE1681.1. Two site PCR mutagenesis, using the Quikchange site directed mutagenesis kit from Stratagene with oligos 7751 (SEQ ID NO.:2; GGACGGTAGTAGGTG-TATGATGGAGATATAGTTGGGTCGTCTGGGCC) and 7760 (SEQ ID NO.:3; CAGAATGAATTATCCGTTGAT-CACTCC), was performed to correct the two remaining point mutations pSE1681.1. The corrected clone was designated pSE1686.1 (pUC18 mCEA modified repeat 2; FIG. 5).

Figure 6:
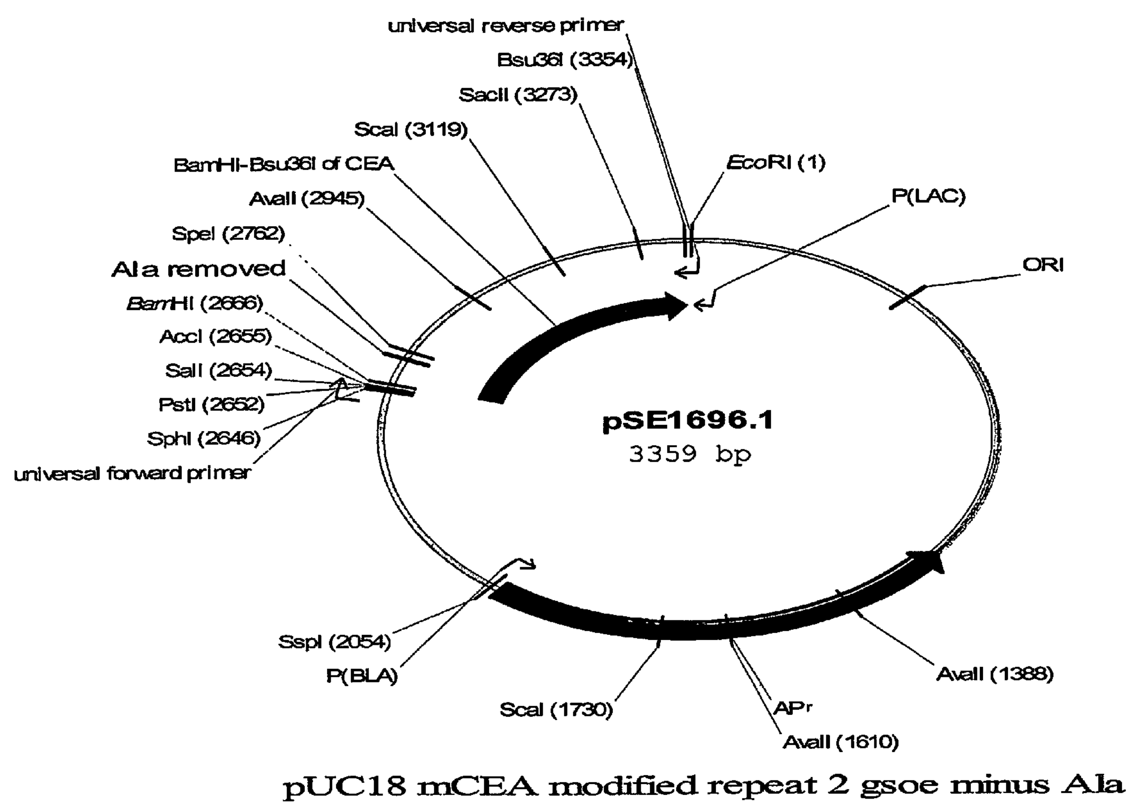
FIG. 6. Illustration of plasmid pSE1696.1 (pUC18 mCEA modified repeat 2.

As noted recently, an Alanine codon was absent from 5' terminus of the second repeat in plasmid p3'H6MCEA which contained CEA. To preserve the consistency of the amino acid sequence of CEA, the Alanine codon present in plasmid pSE1686.1 containing the modified second repeat of CEA was knocked out. This was accomplished using oligos 7802 (SEQ ID NO.:4; CGTGACGACGATTACCGTGTAT-GAGCCACCAAAACCATTCATAAC) and 7803 (SEQ ID NO.:5; GTTATGAATGGTTTTGGTGGCTCATA-CACGGTAATCGTCGTCACG) and the Quikchange site-directed mutagenesis kit from Stratagene. The resulting plasmid, pSE1696.1 (pUC18 mCEA modified repeat 2; FIG. 6) was confirmed by sequencing.

Figure 7:
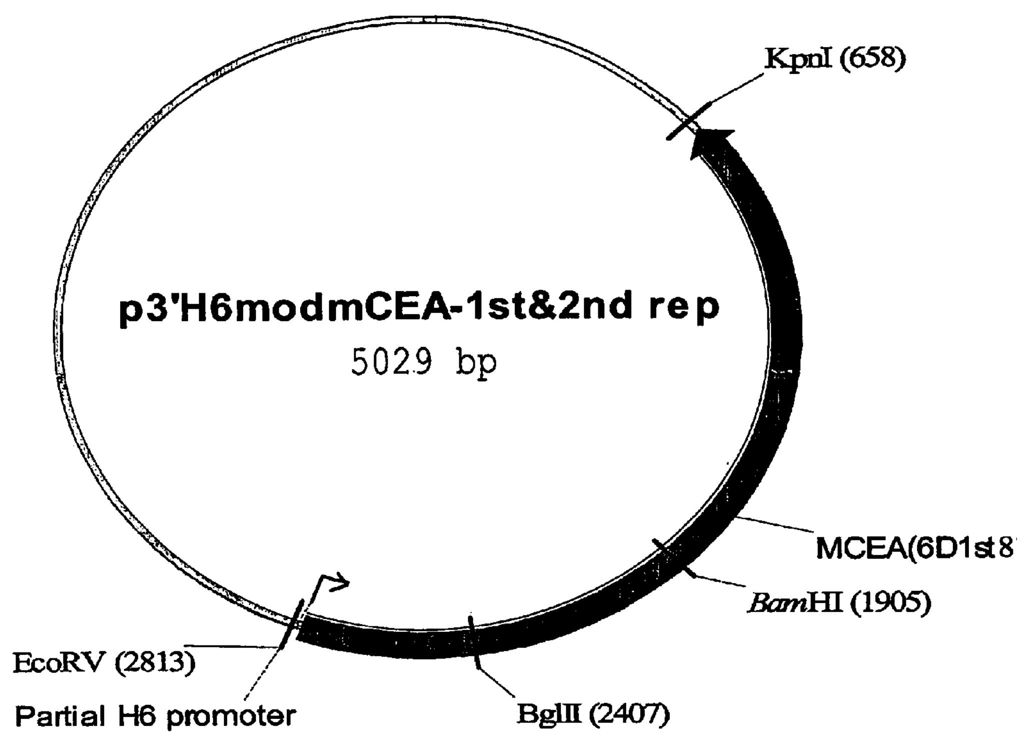
FIG. 7. Illustration of plasmid p3'HomodMCEA-1st&2nd repeats.

The 694 bp Bsu36I-BamHI fragment from pSE1696.1 was cloned into Bsu36I-BamHI site of Pse1658.15 to combine modified repeats 1 and 2. The generated plasmid was designated p3'HomodMCEA-1st&2nd repeats (FIG. 7).

C. Construction of ALVAC Donor Plasmid pNVQH6MCEA(6D1st&2nd)

Figure 8:
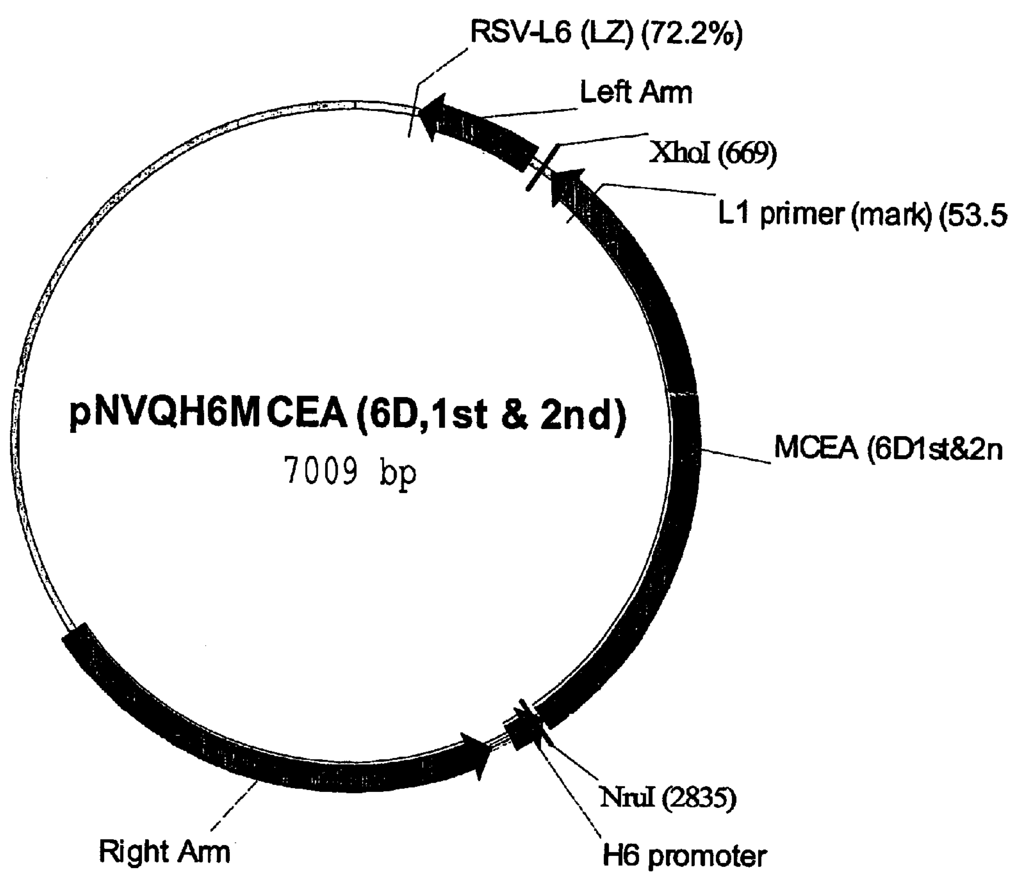
FIG. 8. Illustration of plasmid pNVQH6MCEA (6D1st&2nd).

The 2.2 kb NruI/XhoI fragment from p3'HomodMCEA-1st&2ndrepeats was cloned into NruI/XhoI site of pNVQH6LSP-18, generating pNVQH6MCEA(6D1st&$2^{nd}$; FIG. 8). The modified CEA sequence ("CAP(6D)-1,2"; SEQ ID NO. 6) contained within pNVQH6MCEA is shown in FIG. 9.

D. Expression of Modified CEA

Figure 10:
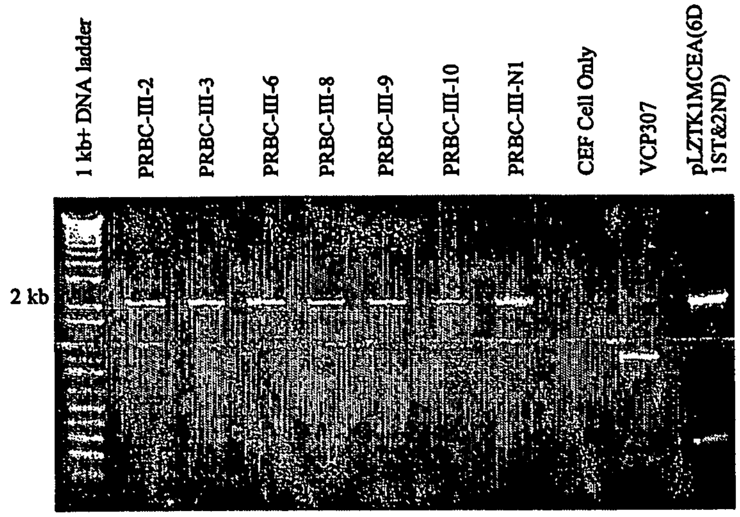
FIG. 10. PCR analysis to confirm the presence of CAP (6D)-1,2 in NYVAC DNA.

To test the stability of the CAP(6D)-1,2 sequence upon expression in a cell, the gene together with flanking H6 promoter was PCR amplified using pNVQH6MCEA (6D1ST&2ND) as template and two oligos (8034LZ, SEQ ID NO.:7; CTGGCGCGCCTTCTTTTATTCTATACT-TAAAAAGTG; and 8035LZ, SEQ ID NO.:8: CTGGTAC-CAGAAAAACTATATCAGAGCAACCCCAAC). The PCR product was then cloned into an NYVAC TK donor plasmid designated pLZTK1 containing the LacZ and K1L marker genes. This vector was specifically made for the generation of recombinant virus in NYVAC by using blue/white screening method. After in vitro recombination between donor plasmid pLZTK1mCEA(6D1st&2nd) and NYVAC, the foreign CAP (6D)-1,2 sequence and marker genes are integrated into the NYVAC genome. The plaques containing intermediate recombinant NYVAC with both LacZ and mCEA appeared blue. Several rounds of plaque purification were then performed. The second recombination event kicked out the marker genes resulting in the final white plaques containing recombinants with only the CAP(6D)-1,2 sequence but no marker genes (FIG. 10).

The recombinant white plaques and blue plaques were picked for confirmation of CAP(6D)-1,2 sequence expression. Infection was performed using the virus from the respective plaques and the cells were harvested three days after infection for preparing either cellular DNA or Cell lysate. For isolation of recombinant NYVAC DNA, DNAzol® reagent (GibcoBRL) was used. PCR (PCR Condition: 95° C. (5 min)∴[95° C. (30 sec)∴49° C.(30 sec)∴72° C.(1 min)] 30 cycles∴>72° C. (7 min)∴4° C.) was run to confirm the existence of CAP(6D)-1,2 sequence in the recombinant NYVAC genome. The primers used were 7569LZ (5' ttggatccatggagtctccctcggcc 3' forward primer; SEQ ID NO.:9) and 7570LZ (5' ttggatccctatatcagagcaacccc 3' reverse primer; SEQ ID NO.:10), which could amplify the full length 2106 bp CAP(6D)-1,2.

The final recombinant white plaques PRBC-III-2,3,6,8, 9, 10 all demonstrated the 2.1 kb CAP(6D)-1,2 sequence band in PCR. PRBC-III-N1 was a blue plaque with both marker genes and CAP(6D)-1,2 sequence still in the viral genome and the CAP(6D)-1,2 sequence band was also amplified in the PCR. The prominent PCR band amplified from vCP 307 DNA (containing native CEA integrated into the ALVAC genome) was truncated CEA at 1.2 kb with a very faint full-length CEA band. The cell-only sample (no viral infection) was used as a negative control and the plasmid pLZTK1MCEA(6D1 ST&2ND) was a positive control used in the PCR reaction. The PCR results clearly showed the full-length CAP(6D)-1,2 in the recombinant viral genome with no other truncated form of CEA visible. This result indicated that CAP(6D)-1,2 has increased stability relative to the native CEA in the ALVAC genome.

Figure 11:
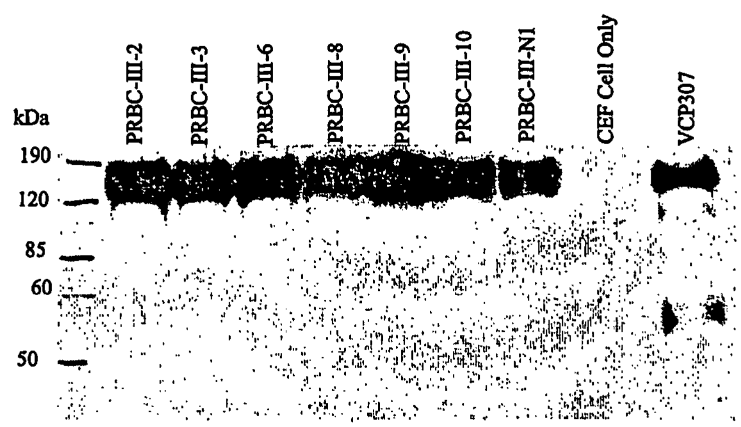
FIG. 11. Immunoblot illustrating the lack of truncated CEA in cells expressing CAP(6D) 1,2.

Protein expression was also assayed by immunoblot to confirm the absence of truncated CEA protein in cells expressing CAP(6D)-1,2 (FIG. 11). For isolation of cell lysate, cells were first washed with PBS followed by the addition of Lysis Buffer (Reporter Gene Assay; Boehringer Mannheim) and shaking for 15 minutes. Cell lysate was spun down at 13,000 rpm and the supernatant was collected for Western blot analysis. Samples were loaded onto a 10% polyacrylamide gel and run at 125 volts. The protein was then transferred to a PVDF filter membrane (Immobilon-P, Millipore). An HRP-linked mouse CEA monoclonal antibody (1:1000; Fitzgerald) was used to detect the expression of mCEA with the enhancement from a chemiluminescence reagent (DNA Thunder™; NEN™ Life Science Products).

All six final CAP(6D)-1,2 recombinants were plaques (PRBC-III-2,3,6,8,9,10) and one intermediate blue plaque (pRBC-III-N1) showed only one CEA band with no other truncated form (FIG. 11). In contrast, protein from vCP307 plaques (recombinant ALVAC expressing native CEA) showed a clear truncated CEA product at ~60 kDa in addition to the full length CEA. Prolonged exposure of the film verified the absence of any truncated CEA polypeptides in the CAP(6D)-1,2 recombinants. CEF was used as the negative control. In conclusion, the CAP(6D)-1,2 recombinants were generated with the mCEA instead of the native CEA to prevent the expression of multiple versions of CEA. CAP(6D)-1,2 expressed from recombinant NYVAC was proven effective in eliminating truncated version of CEA by both PCR and Western blot.

E. Recombinant ALVAC Vector for Expressing B7.1 and CAP(6D)-1,2 CEA

The human B7.1 gene was inserted into an ALVAC C6 donor plasmid under the control of the H6 promoter as shown in FIG. 12. This donor plasmid was then used with ALVAC to generate the ALVAC recombinant vCP306 using standard techniques. The donor plasmid inserts into the C6 site of the ALVAC genome. The CAP(6D)-1,2 CEA DNA sequence was inserted into an ALVAC C3 donor plasmid under the control of the H6 promoter as shown in FIG. 13. This donor plasmid was then used with vCP306 to generate the ALVAC recombinant vCP2140 (ALVAC-CAP(6D)-1,2 CEA-B7.1) expressing these genes using standard techniques. The donor plasmid inserts into the C3 site of the ALVAC genome. This vector may be used; for example, to express B7.1 and/or CEA in vitro (i.e., in cell culture) or in vivo (for immunization purposes).

While the present invention has been described in terms of the preferred embodiments, it is understood that variations and modifications will occur to those skilled in the art. Therefore, it is intended that the appended claims cover all such equivalent variations that come within the scope of the invention as claimed.

What is claimed is:

1. An expression vector comprising the nucleic acid sequence of SEQ ID No. 6 and a nucleic acid sequence encoding human B7.1.

2. The expression vector of claim 1 wherein the human B7.1 is encoded by nucleotides 792-1658 of SEQ ID NO. 11.

3. The expression vector of claim 1 wherein the vector is a plasmid or a viral vector.

4. The expression vector of claim 3 wherein the viral vector is selected from the group consisting of poxvirus, adenovirus, retrovirus, herpesvirus, and adeno-associated virus.

5. The expression vector of claim 4 wherein the viral vector is a poxvirus selected from the group consisting of NYVAC, ALVAC, and ALVAC(2).

6. The expression vector of claim 3 wherein the viral vector is a poxvirus selected from the group consisting of vaccinia, Modified Vaccinia Virus Ankara (MVA), NYVAC, avipox, canarypox, ALVAC, ALVAC(2), fowlpox, and TROVAC.

7. The expression vector of claim 6 further comprising at least one additional nucleotide sequence encoding a tumor associated antigen.

8. The expression vector of claim 6 wherein the poxvirus is avipox.

9. The expression vector of claim 8 wherein the avipox is ALVAC or ALVAC(2).

10. The expression vector of claim 9 wherein the avipox is ALVAC(2).

11. An isolated DNA molecule comprising the nucleic acid sequence of SEQ ID No. 6 and a nucleotide sequence encoding human B7.1.

12. The DNA molecule vector of claim 11 wherein the human B7.1 is encoded by nucleotides 792-1658 of SEQ ID NO. 11.

* * * * *

SEQUENCE LISTING

```
<160> NUMBER OF SEQ ID NOS: 14

<210> SEQ ID NO 1
<211> LENGTH: 2106
<212> TYPE: DNA
<213> ORGANISM: Homo sapiens
<223> OTHER INFORMATION: mCEA coding sequence

<400> SEQUENCE: 1

atggagtctc cctcggcccc tccccacaga tggtgcatcc cctggcagag gctcctgctc     60

acagcctcac ttctaacctt ctggaacccg cccaccactg ccaagctcac tattgaatcc    120

acgccgttca atgtcgcaga ggggaaggag gtgcttctac ttgtccacaa tctgccccag    180

catctttttg gctacagctg gtacaaaggt gaaagagtgg atggcaaccg tcaaattata    240

ggatatgtaa taggaactca acaagctacc ccagggcccg catacagtgg tcgagagata    300

atataccccca atgcatccct gctgatccag aacatcatcc agaatgacac aggattctac    360

accctacacg tcataaagtc agatcttgtg aatgaagaag caactggcca gttccgggta    420

tacccggagc tgcccaagcc ctccatctcc agcaacaact ccaaacccgt ggaggacaag    480

gatgctgtgg ccttcacctg tgaacctgag actcaggacg caacctacct gtggtgggta    540

aacaatcaga gcctcccggt cagtcccagg ctgcagctgt ccaatggcaa caggaccctc    600

actctattca atgtcacaag aaatgacaca gcaagctaca aatgtgaaac ccagaaccca    660
```

-continued

```
gtgagtgcca ggcgcagtga ttcagtcatc ctgaatgtcc tctatggccc ggatgccccc    720
accatttccc ctctaaacac atcttacaga tcaggggaaa atctgaacct ctcctgccac    780
gcagcctcta acccacctgc acagtactct tggtttgtca atgggacttt ccagcaatcc    840
acccaagagc tctttatccc caacatcact gtgaataata gtggatccta tacgtgccaa    900
gcccataact cagacactgg cctcaatagg accacagtca cgacgatcac agtctatgag    960
ccacccaaac ccttcatcac cagcaacaac tccaaccccg tggaggatga ggatgctgta   1020
gccttaacct gtgaacctga gattcagaac acaacctacc tgtggtgggt aaataatcag   1080
agcctcccgg tcagtcccag gctgcagctg tccaatgaca acaggaccct cactctactc   1140
agtgtcacaa ggaatgatgt aggaccctat gagtgtggaa tccagaacga attaagtgtt   1200
gaccacagcg acccagtcat cctgaatgtc ctctatggcc cagacgaccc caccatttcc   1260
ccctcataca cctattaccg tccaggggtg aacctcagcc tctcctgcca tgcagcctct   1320
aacccacctg cacagtattc ttggctgatt gatgggaaca tccagcaaca cacacaagag   1380
ctctttatct ccaacatcac tgagaagaac agcggactct atacctgcca ggccaataac   1440
tcagccagtg gccacagcag gactacagtc aagacaatca cagtctctgc ggagctgccc   1500
aagccctcca tctccagcaa caactccaaa cccgtggagg acaaggatgc tgtggccttc   1560
acctgtgaac ctgaggctca gaacacaacc tacctgtggt gggtaaatgg tcagagcctc   1620
ccagtcagtc ccaggctgca gctgtccaat ggcaacagga ccctcactct attcaatgtc   1680
acaagaaatg acgcaagagc ctatgtatgt ggaatccaga actcagtgag tgcaaaccgc   1740
agtgacccag tcaccctgga tgtcctctat gggccggaca cccccatcat ttccccccca   1800
gactcgtctt acctttcggg agcggacctc aacctctcct gccactcggc ctctaaccca   1860
tccccgcagt attcttggcg tatcaatggg ataccgcagc aacacacaca agttctcttt   1920
atcgccaaaa tcacgccaaa taataacggg acctatgcct gttttgtctc taacttggct   1980
actggccgca ataattccat agtcaagagc atcacagtct ctgcatctgg aacttctcct   2040
ggtctctcag ctggggccac tgtcggcatc atgattggag tgctggttgg ggttgctctg   2100
atatag                                                              2106
```

<210> SEQ ID NO 2
<211> LENGTH: 47
<212> TYPE: DNA
<213> ORGANISM: Homo sapiens
<223> OTHER INFORMATION: Primer 7751

<400> SEQUENCE: 2

```
ggacggtagt aggtgtatga tggagatata gttgggtcgt ctgggcc                   47
```

<210> SEQ ID NO 3
<211> LENGTH: 27
<212> TYPE: DNA
<213> ORGANISM: Homo sapiens
<223> OTHER INFORMATION: Primer 7760

<400> SEQUENCE: 3

```
cagaatgaat tatccgttga tcactcc                                         27
```

<210> SEQ ID NO 4
<211> LENGTH: 45
<212> TYPE: DNA
<213> ORGANISM: Homo sapiens
<223> OTHER INFORMATION: Primer 7802

<400> SEQUENCE: 4
cgtgacgacg attaccgtgt atgagccacc aaaaccattc ataac 45

<210> SEQ ID NO 5
<211> LENGTH: 45
<212> TYPE: DNA
<213> ORGANISM: Homo sapiens
<223> OTHER INFORMATION: Primer 7803

<400> SEQUENCE: 5
gttatgaatg gttttggtgg ctcatacacg gtaatcgtcg tcacg 45

<210> SEQ ID NO 6
<211> LENGTH: 2106
<212> TYPE: DNA
<213> ORGANISM: Homo sapiens
<223> OTHER INFORMATION: CAP(6D)-1,2 cDNA

<400> SEQUENCE: 6
atggagtctc cctcggcccc tccccacaga tggtgcatcc cctggcagag gctcctgctc 60
acagcctcac ttctaacctt ctggaacccg cccaccactg ccaagctcac tattgaatcc 120
acgccgttca atgtcgcaga ggggaaggag gtgcttctac ttgtccacaa tctgccccag 180
catctttttg gctacagctg gtacaaaggt gaaagagtgg atggcaaccg tcaaattata 240
ggatatgtaa taggaactca acaagctacc ccagggcccg catacagtgg tcgagagata 300
atatacccca atgcatccct gctgatccag aacatcatcc agaatgacac aggattctac 360
accctacacg tcataaagtc agatcttgtg aatgaagaag caactggcca gttccgggta 420
tacccggaac tccctaagcc ttctattagc tccaataata gtaagcctgt cgaagacaaa 480
gatgccgtcg cttttacatg cgagcccgaa actcaagacg caacatatct ctggtgggtg 540
aacaaccagt ccctgcctgt gtcccctaga ctccaactca gcaacggaaa tagaactctg 600
accctgttta acgtgaccag gaacgacaca gcaagctaca aatgcgaaac ccaaaatcca 660
gtcagcgcca ggaggtctga ttcagtgatt ctcaacgtgc tttacggacc cgatgctcct 720
acaatcagcc ctctaaacac aagctataga tcaggggaaa atctgaatct gagctgtcat 780
gccgctagca atcctcccgc ccaatacagc tggtttgtca atggcacttt ccaacagtcc 840
acccaggaac tgttcattcc caatattacc gtgaacaata gtggatccta cacgtgccaa 900
gctcacaata gcgacaccgg actcaaccgc acaaccgtga cgacgattac cgtgtatgag 960
ccaccaaaac cattcataac tagtaacaat tctaacccag ttgaggatga ggacgcagtt 1020
gcattaactt gtgagccaga gattcaaaat accacttatt tatggtgggt caataaccaa 1080
agtttgccgg ttagcccacg cttgcagttg tctaatgata accgcacatt gacactcctg 1140
tccgttactc gcaatgatgt aggaccttat gagtgtggca ttcagaatga attatccgtt 1200
gatcactccg accctgttat ccttaatgtt ttgtatggcc cagacgaccc aactatatct 1260
ccatcataca cctactaccg tcccggcgtg aacttgagcc tttcttgcca tgcagcatcc 1320
aacccccctg cacagtactc ctggctgatt gatggaaaca ttcagcagca tactcaagag 1380
ttatttataa gcaacataac tgagaagaac agcggactct atacttgcca ggccaataac 1440
tcagccagtg gtcacagcag gactacagtt aaaacaataa ctgtttccgc ggagctgccc 1500
aagccctcca tctccagcaa caactccaaa cccgtggagg acaaggatgc tgtggccttc 1560
acctgtgaac ctgaggctca gaacacaacc tacctgtggt gggtaaatgg tcagagcctc 1620
ccagtcagtc ccaggctgca gctgtccaat ggcaacagga ccctcactct attcaatgtc 1680
acaagaaatg acgcaagagc ctatgtatgt ggaatccaga actcagtgag tgcaaaccgc 1740
agtgacccag tcaccctgga tgtcctctat gggccggaca cccccatcat ttcccccca 1800 gactcgtctt acctttcggg agcggacctc aacctctcct gccactcggc ctctaaccca 1860
tccccgcagt attcttggcg tatcaatggg ataccgcagc aacacacaca agttctcttt 1920
atcgccaaaa tcacgccaaa taataacggg acctatgcct gttttgtctc taacttggct 1980
actggccgca ataattccat agtcaagagc atcacagtct ctgcatctgg aacttctcct 2040
ggtctctcag ctggggccac tgtcggcatc atgattggag tgctggttgg ggttgctctg 2100
atatag 2106

<210> SEQ ID NO 7
<211> LENGTH: 35
<212> TYPE: DNA
<213> ORGANISM: Homo sapiens
<223> OTHER INFORMATION: Primer 8034LZ

<400> SEQUENCE: 7
ctggcgcgcc ttctttattc tatacttaaa aagtg 35

<210> SEQ ID NO 8
<211> LENGTH: 36
<212> TYPE: DNA
<213> ORGANISM: Homo sapiens
<223> OTHER INFORMATION: Primer 8035LZ

<400> SEQUENCE: 8
ctggtaccag aaaaactata tcagagcaac cccaac 36

<210> SEQ ID NO 9
<211> LENGTH: 26
<212> TYPE: DNA
<213> ORGANISM: Homo sapiens
<223> OTHER INFORMATION: Primer 7569LZ

<400> SEQUENCE: 9
ttggatccat ggagtctccc tcggcc 26

<210> SEQ ID NO 10
<211> LENGTH: 26
<212> TYPE: DNA
<213> ORGANISM: Homo sapiens
<223> OTHER INFORMATION: Primer 7570LZ

<400> SEQUENCE: 10
ttggatccct atatcagagc aacccc 26

<210> SEQ ID NO 11
<211> LENGTH: 2269
<212> TYPE: DNA
<213> ORGANISM: Avipoxvirus
<223> OTHER INFORMATION: ALVAC-Figure 12

<400> SEQUENCE: 11
ttagattgtg ttattcatta catagacgct gctaaatcta ctatcgattt agagatagta 60
tctctactac ccacaaaaag aactaaagac gccatagtgt actggcctat aataaaagac 120
gcgttgataa gagctgttct ggaacgtggt gttaaactta gaatactact aggttattgg 180
aaaaagaccg atattatctc taaagcttct atcaaaagtc ttaatgagtt aggtgtagat 240
agtatagata ttactacaaa ggtattcata tttcctatca attctaaagt agatgatatt 300
aataactcaa agatgatgat agtagataat agatacgctc atataatgac tgcaaatttg 360

```
gacggttcac attttaatca tcacgcgttc ataagtctca actgcataga tcaaaatctc    420

actaaaaaga tagccgatgt atttgagaga gattggacat ctaactacgc taaagaaatt    480

acagttataa ataatacata atggattttg ttatcatcag ttatatttaa cataagtaca    540

ataaaaagta ttaaataaaa atacttactt acgaaaaaat gactaattag ctataaaaac    600

ccgggttaat taattagtta ttagacaagg tgaaaacgaa actatttgta gcttaattaa    660

ttagagcttc tttattctat acttaaaaag tgaaaataaa tacaaaggtt cttgagggtt    720

gtgttaaatt gaaagcgaga aataatcata aattatttca ttatcgcgat atccgttaag    780

tttgtatcgt aatgggccac acacggaggc agggaacatc accatccaag tgtccatacc    840

tcaatttctt tcagctcttg gtgctggctg gtctttctca cttctgttca ggtgttatcc    900

acgtgaccaa ggaagtgaaa gaagtggcaa cgctgtcctg tggtcacaat gtttctgttg    960

aagagctggc acaaactcgc atctactggc aaaaggagaa gaaaatggtg ctgactatga   1020

tgtctggaga catgaatata tggcccgagt acaagaaccg gaccatcttt gatatcacta   1080

ataacctctc cattgtgatc ctggctctgc gcccatctga cgagggcaca tacgagtgtg   1140

ttgttctgaa gtatgaaaaa gacgctttca agcgggaaca cctggctgaa gtgacgttat   1200

cagtcaaagc tgacttccct acacctagta tatctgactt tgaaattcca acttctaata   1260

ttagaaggat aatttgctca acctctggag gttttccaga gcctcacctc tcctggttgg   1320

aaaatggaga agaattaaat gccatcaaca caacagtttc ccaagatcct gaaactgagc   1380

tctatgctgt tagcagcaaa ctggatttca atatgacaac caaccacagc ttcatgtgtc   1440

tcatcaagta tggacattta agagtgaatc agaccttcaa ctggaataca accaagcaag   1500

agcattttcc tgataacctg ctcccatcct gggccattac cttaatctca gtaaatggaa   1560

ttttcgtgat atgctgcctg acctactgct ttgccccacg ctgcagagag agaaggagga   1620

atgagagatt gagaagggaa agtgtacgtc ctgtataatt tttatctcga gcccgggaag   1680

cttgaattct ttttattgat taactagtca aatgagtata tataattgaa aaagtaaaat   1740

ataaatcata taataatgaa acgaaatatc agtaatagac aggaactggc agattcttct   1800

tctaatgaag taagtactgc taaatctcca aaattagata aaaatgatac agcaaataca   1860

gcttcattca acgaattacc ttttaatttt ttcagacaca ccttattaca aactaactaa   1920

gtcagatgat gagaaagtaa atataaattt aacttatggg tataatataa taaagattca   1980

tgatattaat aatttactta acgatgttaa tagacttatt ccatcaaccc cttcaaacct   2040

ttctggatat tataaaatac cagttaatga tattaaaata gattgtttaa gagatgtaaa   2100

taattatttg gaggtaaagg atataaaatt agtctatctt tcacatggaa atgaattacc   2160

taatattaat aattatgata ggaatttttt aggatttaca gctgttatat gtatcaacaa   2220

tacaggcaga tctatggtta tggtaaaaca ctgtaacggg aagcagcat               2269
```

```
<210> SEQ ID NO 12
<211> LENGTH: 2269
<212> TYPE: DNA
<213> ORGANISM: Avipoxvirus
<223> OTHER INFORMATION: ALVAC-Figure 12 Antisense

<400> SEQUENCE: 12

aatctaacac aataagtaat gtatctgcga cgatttagat gatagctaaa tctctatcat     60

agagatgatg ggtgtttttc ttgatttctg cggtatcaca tgaccggata ttattttctg    120

cgcaactatt ctcgacaaga ccttgcacca caatttgaat cttatgatga tccaataacc    180

tttttctggc tataatagag atttcgaaga tagttttcag aattactcaa tccacatcta    240
```

```
tcatatctat aatgatgttt ccataagtat aaaggatagt taagatttca tctactataa    300

ttattgagtt tctactacta tcatctatta tctatgcgag tatattactg acgtttaaac    360

ctgccaagtg taaaattagt agtgcgcaag tattcaaagt tgacgtatct agttttagag    420

tgatttttct atcggctaca taaactctct ctaacctgta gattgatgcg atttctttaa    480

tgtcaatatt tattatgtat tacctaaaac aatagtagtc aatataaatt gtattcatgt    540

tatttttcat aatttatttt tatgaatgaa tgctttttta ctgattaatc gatatttttg    600

ggcccaatta attaatcaat aatctgttcc acttttgctt tgataaacat cgaattaatt    660

aatctcgaag aaataagata tgaatttttc acttttattt atgtttccaa gaactcccaa    720

cacaatttaa ctttcgctct ttattagtat ttaataaagt aatagcgcta taggcaattc    780

aaacatagca ttacccggtg tgtgcctccg tcccttgtag tggtaggttc acaggtatgg    840

agttaaagaa agtcgagaac cacgaccgac cagaaagagt gaagacaagt ccacaatagg    900

tgcactggtt ccttcacttt cttcaccgtt gcgacaggac accagtgtta caaagacaac    960

ttctcgaccg tgtttgagcg tagatgaccg ttttcctctt cttttaccac gactgatact   1020

acagacctct gtacttatat accgggctca tgttcttggc ctggtagaaa ctatagtgat   1080

tattggagag gtaacactag gaccgagacg cgggtagact gctcccgtgt atgctcacac   1140

aacaagactt catacttttt ctgcgaaagt tcgcccttgt ggaccgactt cactgcaata   1200

gtcagtttcg actgaaggga tgtggatcat atagactgaa actttaaggt tgaagattat   1260

aatcttccta ttaaacgagt tggagacctc caaaaggtct cggagtggag aggaccaacc   1320

ttttacctct tcttaattta cggtagttgt gttgtcaaag ggttctagga ctttgactcg   1380

agatacgaca atcgtcgttt gacctaaagt tatactgttg gttggtgtcg aagtacacag   1440

agtagttcat acctgtaaat tctcacttag tctggaagtt gaccttatgt tggttcgttc   1500

tcgtaaaagg actattggac gagggtagga cccggtaatg gaattagagt catttacctt   1560

aaaagcacta tacgacggac tggatgacga aacggggtgc gacgtctctc tcttcctcct   1620

tactctctaa ctcttccctt tcacatgcag gacatattaa aaatagagct cgggcccttc   1680

gaacttaaga aaaataacta attgatcagt ttactcatat atattaactt tttcatttta   1740

tatttagtat attattactt tgctttatag tcattatctg tccttgaccg tctaagaaga   1800

agattacttc attcatgacg atttagaggt tttaatctat ttttactatg tcgtttatgt   1860

cgaagtaagt tgcttaatgg aaaattaaaa aagtctgtgt ggaataatgt ttgattgatt   1920

cagtctacta ctctttcatt tatatttaaa ttgaataccc atattatatt atttctaagt   1980

actataatta ttaaatgaat tgctacaatt atctgaataa ggtagttggg gaagtttgga   2040

aagacctata atattttatg gtcaattact ataattttat ctaacaaatt ctctacattt   2100

attaataaac ctccatttcc tatattttaa tcagatagaa agtgtacctt tacttaatgg   2160

attataatta ttaatactat ccttaaaaaa tcctaaatgt cgacaatata catagttgtt   2220

atgtccgtct agataccaat accattttgt gacattgccc ttcgtcgta               2269
```

```
<210> SEQ ID NO 13
<211> LENGTH: 5259
<212> TYPE: DNA
<213> ORGANISM: Avipoxvirus
<223> OTHER INFORMATION: ALVAC-Figure 13

<400> SEQUENCE: 13

atattattaa aactattaga taacatagct ttatgtaaag gagtatttcc agataactta     60

gctttagcat ttacgtaagc accgtggtca agtaagagtt taacaaattc tgttttcata    120
```

```
gaactaactg ccatgtatag aggagtgaaa cctttatgat tatagacgtt tacatagcaa    180
ccatataata agatcgcatt cagtatatta atatctttca tttctatagc tatgtgaata    240
acatgtttat ctaatcctac caactttgta tcagtaccgt acttcagtaa taagtttact    300
atagttttgt ttttagatgc aacagctata tttagaacgg tatctatatg attattaacc    360
acattaacat tagatcctct ttctaaaagt gtctttgttg tttcgatatc gttacgtgaa    420
acagcgtaat gtaagggact gcccatacag tcatctatta cgtttatatg agctcctaga    480
tttaacagaa gtgctgttac atcttttctt ctattaatta ccgaatgatg taatggggtt    540
ttacctaaat catcttgttc gtttataggc actccgtgat ttataagtaa cgctattata    600
tcgtaactac aattattttt aagtgccttt atgagatact gtttatgcaa aaataaactt    660
ttatctattt taatactatt atctaacaat atcctaatta aatctatatt cttatacttt    720
atagcgtaat gtaacggagt ttcaaaattt ctagtttgta tattaagatc aatattaaaa    780
tctataaata ttttatacat atcatcagat atcttatcat acagtacatc gtaataattt    840
agaaagaatc tattacaatt aacacctttt tttaataaat atctagttaa tgacttattg    900
tttctatata cagaaatata taacggacta tttccagaat gtatctgttc tatgtcagcg    960
ccagaatcta ttagtagttt agcaatttct gtattatcta aactagcagc tttatgaaga   1020
ggaggatttt tacattttaa aatatcggca ccgtgttcta gtaataattt taccatttct   1080
atatcagaaa tacttacggc taaatacaaa gacgttgata gtatatttac gttattgtat   1140
ttgcattttt taagtatata ccttactaaa tttatatctc tataccttat agctttatgc   1200
agttcattta taagtcttcc attactcatt tctggtaatg aagtattata tatcattatg   1260
atattatctc tattttattc taataaaaac cgttatcatg ttatttatta tttgttataa   1320
ttatactatt taataaatta taccaaatac ttagatactt attaatacca tcctagaact   1380
tgtatttctt gccccctaaa cttggacatg cactccatta ggcgtttctt gttttcgaca   1440
tcgtcctcct taacatatcc tactgttatg tgaggattcc acggattatc tactgtgata   1500
tcaccaaaca cgtccttcga acagggtacc gcattcagca gaacatttct tagggctcta   1560
agttcatcag atacctccag tttcataact acagcgcatc ctttcgctcc caactgttta   1620
gaggcgttac tgtgaggaaa acacatctct tctttacaga ctatagaaat agtctgtaaa   1680
tcttgatcag ttatttgctt tttgaaattt tcaaatctat cacattgatc catatttgct   1740
attccaagag ttatatgagg aaaaatatca catcctgtca tgtattttat tgtaacatta   1800
ttataatctg taacatcagt atctaaccta acgtcgtaaa agttaacaga tgcccagtta   1860
ctataatccc aaggaacctt aacatctaat cccattaaaa tagtatcctt tctactattt   1920
ttttcattgg caagtatgtg gcttagttta cacaaaattc ctgccatttt gtaacgatag   1980
cgaagcaata gcttgtatgc tttttatttg attaactagt cataaaaatc gggatccttc   2040
tttattctat acttaaaaag tgaaaataaa tacaaaggtt cttgagggtt gtgttaaatt   2100
gaaagcgaga aataatcata aattatttca ttatcgcgat atccgttaag tttgtatcgt   2160
aatggagtct ccctcggccc ctccccacag atggtgcatc ccctggcaga ggctcctgct   2220
cacagcctca cttctaacct tctggaaccc gcccaccact gccaagctca ctattgaatc   2280
cacgccgttc aatgtcgcag aggggaagga ggtgcttcta cttgtccaca atctgcccca   2340
gcatcttttt ggctacagct ggtacaaagg tgaaagagtg gatggcaacc gtcaaattat   2400
aggatatgta ataggaactc aacaagctac cccagggccc gcatacagtg gtcgagagat   2460
aatataccc aatgcatccc tgctgatcca gaacatcatc cagaatgaca caggattcta   2520
```

-continued

```
caccctacac gtcataaagt cagatcttgt gaatgaagaa gcaactggcc agttccgggt   2580

atacccggaa ctccctaagc cttctattag ctccaataat agtaagcctg tcgaagacaa   2640

agatgccgtc gcttttacat gcgagcccga aactcaagac gcaacatatc tctggtgggt   2700

gaacaaccag tccctgcctg tgtcccctag actccaactc agcaacggaa atagaactct   2760

gaccctgttt aacgtgacca ggaacgacac agcaagctac aaatgcgaaa cccaaaatcc   2820

agtcagcgcc aggaggtctg attcagtgat tctcaacgtg ctttacggac ccgatgctcc   2880

tacaatcagc cctctaaaca caagctatag atcaggggaa aatctgaatc tgagctgtca   2940

tgccgctagc aatcctcccg cccaatacag ctggtttgtc aatggcactt tccaacagtc   3000

cacccaggaa ctgttcattc ccaatattac cgtgaacaat agtggatcct acacgtgcca   3060

agctcacaat agcgacaccg gactcaaccg cacaaccgtg acgacgatta ccgtgtatga   3120

gccaccaaaa ccattcataa ctagtaacaa ttctaaccca gttgaggatg aggacgcagt   3180

tgcattaact tgtgagccag agattcaaaa taccacttat ttatggtggg tcaataacca   3240

aagtttgccg gttagcccac gcttgcagtt gtctaatgat aaccgcacat tgacactcct   3300

gtccgttact cgcaatgatg taggacctta tgagtgtggc attcagaatg aattatccgt   3360

tgatcactcc gaccctgtta tccttaatgt tttgtatggc ccagacgacc caactatatc   3420

tccatcatac acctactacc gtcccggcgt gaacttgagc ctttcttgcc atgcagcatc   3480

caaccccct gcacagtact cctggctgat tgatggaaac attcagcagc atactcaaga   3540

gttatttata agcaacataa ctgagaagaa cagcggactc tatacttgcc aggccaataa   3600

ctcagccagt ggtcacagca ggactacagt taaaacaata actgtttccg cggagctgcc   3660

caagccctcc atctccagca acaactccaa acccgtggag gacaaggatg ctgtggcctt   3720

cacctgtgaa cctgaggctc agaacacaac ctacctgtgg tgggtaaatg gtcagagcct   3780

cccagtcagt cccaggctgc agctgtccaa tggcaacagg accctcactc tattcaatgt   3840

cacaagaaat gacgcaagag cctatgtatg tggaatccag aactcagtga gtgcaaaccg   3900

cagtgaccca gtcaccctgg atgtcctcta tgggccggac acccccatca tttccccccc   3960

agactcgtct tacctttcgg gagcgaacct caacctctcc tgccactcgg cctctaaccc   4020

atccccgcag tattcttggc gtatcaatgg gataccgcag caacacacac aagttctctt   4080

tatcgccaaa atcacgccaa ataataacgg gacctatgcc tgttttgtct ctaacttggc   4140

tactggccgc aataattcca tagtcaagag catcacagtc tctgcatctg gaacttctcc   4200

tggtctctca gctggggcca ctgtcggcat catgattgga gtgctggttg gggttgctct   4260

gatatagttt ttatctcgag gaattcctgc agcccgggtt tttatagcta attagtcaaa   4320

tgtgagttaa tattagtata ctacattact aatttattac atattcattt atatcaatct   4380

agtagcattt agcttttata aaacaatata actgaatagt acatacttta ctaataagtt   4440

ataaataaga gatacatatt tatagtattt tactttctac actgaatata ataatataat   4500

tatacaaata taatttttaa tactatatag tatataactg aaataaaata ccagtgtaat   4560

atagttatta tacatttata ccacatcaaa gatgagttat aacatcagtg tcactgttag   4620

caacagtagt tatacgatga gtagttactc tcgtatggcg ttagtatgta tgtatcttct   4680

agttttctta gtaggcatta taggaaacgt caagcttata aggttattaa tggtatctag   4740

aaatatatct attataccgt ttctcaactt gggaatagcc gatttgctgt ttgtgatatt   4800

cataccttta tacattatat acatactaag taatttccat tggcattttg gtaaagcact   4860

ttgtaaaatt agttctttct tttttacttc taacatgttt gcaagtatat ttttaataac   4920
```

```
tgtaataagc gtatatagat atgtaaaaat tacccttcct ggatttacct ataaatatgt   4980

taacattaga aatatgtaca ttactatatt tttcatatgg attatttcta ttatactagg   5040

gattcctgct ctttacttta gaaatactat cgtaacaaaa aataacgaca cgctgtgtat   5100

taatcattat catgataata gagaaattgc tgaattgatt tacaaagtta ttatctgtat   5160

cagatttatt ttaggatacc tactacctac gataattata ctcgtatgct atacgttact   5220

gatctacaga actaacaatg catgtcgacg cggccgcaa                          5259
```

```
<210> SEQ ID NO 14
<211> LENGTH: 5259
<212> TYPE: DNA
<213> ORGANISM: Avipoxvirus
<223> OTHER INFORMATION: ALVAC-Figure 13 Antisense

<400> SEQUENCE: 14
```

```
tataataatt ttgataatct attgtatcga aatacatttc ctcataaagg tctattgaat     60

cgaaatcgta aatgcattcg tggcaccagt tcattctcaa attgtttaag acaaaagtat    120

cttgattgac ggtacatatc tcctcacttt ggaaatacta atatctgcaa atgtatcgtt    180

ggtatattat tctagcgtaa gtcatataat tatagaaagt aaagatatcg atacacttat    240

tgtacaaata gattaggatg gttgaaacat agtcatggca tgaagtcatt attcaaatga    300

tatcaaaaca aaaatctacg ttgtcgatat aaatcttgcc atagatatac taataattgg    360

tgtaattgta atctaggaga aagattttca cagaaacaac aaagctatag caatgcactt    420

tgtcgcatta cattccctga cgggtatgtc agtagataat gcaaatatag tcgaggatct    480

aaattgtctt cacgacaatg tagaaaagaa gataattaat ggcttactac attaccccaa    540

aatggattta gtagaacaag caaatatccg tgaggcacta aatattcatt gcgataatat    600

agcattgatg ttaataaaaa ttcacggaaa tactctatga caaatacgtt tttatttgaa    660

aatagataaa attatgataa tagattgtta taggattaat ttagatataa gaatatgaaa    720

tatcgcatta cattgcctca aagttttaaa gatcaaacat ataattctag ttataatttt    780

agatatttat aaaatatgta tagtagtcta tagaatagta tgtcatgtag cattattaaa    840

tctttcttag ataatgttaa ttgtggaaaa aaattattta tagatcaatt actgaataac    900

aaagatatat gtctttatat attgcctgat aaaggtctta catagacaag atacagtcgc    960

ggtcttagat aatcatcaaa tcgttaaaga cataatagat ttgatcgtcg aaatacttct   1020

cctcctaaaa atgtaaaatt ttatagccgt ggcacaagat cattattaaa atggtaaaga   1080

tatagtcttt atgaatgccg atttatgttt ctgcaactat catataaatg caataacata   1140

aacgtaaaaa attcatatat ggaatgattt aaatatagag atatggaata tcgaaatacg   1200

tcaagtaaat attcagaagg taatgagtaa agaccattac ttcataatat atagtaatac   1260

tataatagag ataaaataag attatttttg gcaatagtac aataaataat aaacaatatt   1320

aatatgataa attatttaat atggtttatg aatctatgaa taattatggt aggatcttga   1380

acataaagaa cgggggattt gaacctgtac gtgaggtaat ccgcaaagaa caaaagctgt   1440

agcaggagga attgtatagg atgacaatac actcctaagg tgcctaatag atgacactat   1500

agtggtttgt gcaggaagct tgtcccatgg cgtaagtcgt cttgtaaaga atcccgagat   1560

tcaagtagtc tatggaggtc aaagtattga tgtcgcgtag gaaagcgagg gttgacaaat   1620

ctccgcaatg agactccttt tgtgtagaga agaaatgtct gatatcttta tcagacattt   1680

agaactagtc aataaacgaa aaactttaaa agtttagata gtgtaactag gtataaacga   1740

taaggttctc aatatactcc tttttatagt gtaggacagt acataaaata acattgtaat   1800
```

```
aatattagac attgtagtca tagattggat tgcagcattt tcaattgtct acgggtcaat   1860
gatattaggg ttccttggaa ttgtagatta gggtaatttt atcataggaa agatgataaa   1920
aaaagtaacc gttcatacac cgaatcaaat gtgttttaag gacggtaaaa cattgctatc   1980
gcttcgttat cgaacatacg aaaaataaac taattgatca gtatttttag ccctaggaag   2040
aaataagata tgaatttttc acttttattt atgtttccaa gaactcccaa cacaatttaa   2100
ctttcgctct ttattagtat ttaataaagt aatagcgcta taggcaattc aaacatagca   2160
ttacctcaga gggagccggg gaggggtgtc taccacgtag gggaccgtct ccgaggacga   2220
gtgtcggagt gaagattgga agaccttggg cgggtggtga cggttcgagt gataacttag   2280
gtgcggcaag ttacagcgtc tccccttcct ccacgaagat gaacaggtgt tagacggggt   2340
cgtagaaaaa ccgatgtcga ccatgtttcc actttctcac ctaccgttgg cagtttaata   2400
tcctatacat tatccttgag ttgttcgatg gggtcccggg cgtatgtcac cagctctcta   2460
ttatatgggg ttacgtaggg acgactaggt cttgtagtag gtcttactgt gtcctaagat   2520
gtgggatgtg cagtatttca gtctagaaca cttacttctt cgttgaccgg tcaaggccca   2580
tatgggcctt gagggattcg gaagataatc gaggttatta tcattcggac agcttctgtt   2640
tctacggcag cgaaaatgta cgctcgggct ttgagttctg cgttgtatag agaccaccca   2700
cttgttggtc agggacggac acaggggatc tgaggttgag tcgttgcctt tatcttgaga   2760
ctgggacaaa ttgcactggt ccttgctgtg tcgttcgatg tttacgcttt gggttttagg   2820
tcagtcgcgg tcctccagac taagtcacta agagttgcac gaaatgcctg ggctacgagg   2880
atgttagtcg ggagatttgt gttcgatatc tagtcccctt ttagacttag actcgacagt   2940
acggcgatcg ttaggagggc gggttatgtc gaccaaacag ttaccgtgaa aggttgtcag   3000
gtgggtcctt gacaagtaag ggttataatg gcacttgtta tcacctagga tgtgcacggt   3060
tcgagtgtta tcgctgtggc ctgagttggc gtgttggcac tgctgctaat ggcacatact   3120
cggtggtttt ggtaagtatt gatcattgtt aagattgggt caactcctac tcctgcgtca   3180
acgtaattga acactcggtc tctaagtttt atggtgaata aataccaccc agttattggt   3240
ttcaaacggc caatcgggtg cgaacgtcaa cagattacta ttggcgtgta actgtgagga   3300
caggcaatga gcgttactac atcctggaat actcacaccg taagtcttac ttaataggca   3360
actagtgagg ctgggacaat aggaattaca aaacataccg ggtctgctgg gttgatatag   3420
aggtagtatg tggatgatgg cagggccgca cttgaactcg gaaagaacgg tacgtcgtag   3480
gttgggggga cgtgtcatga ggaccgacta actacctttg taagtcgtcg tatgagttct   3540
caataaatat tcgttgtatt gactcttctt gtcgcctgag atatgaacgg tccggttatt   3600
gagtcggtca ccagtgtcgt cctgatgtca attttgttat tgacaaaggc gcctcgacgg   3660
gttcgggagg tagaggtcgt tgttgaggtt tgggcacctc ctgttcctac gacaccggaa   3720
gtggacactt ggactccgag tcttgtgttg gatggacacc acccatttac cagtctcgga   3780
gggtcagtca gggtccgacg tcgacaggtt accgttgtcc tgggagtgag ataagttaca   3840
gtgttcttta ctgcgttctc ggatacatac accttaggtc ttgagtcact cacgtttggc   3900
gtcactgggt cagtgggacc tacaggagat acccggcctg tgggggtagt aaaggggggg   3960
tctgagcaga atggaaagcc ctcgcttgga gttggagagg acggtgagcc ggagattggg   4020
taggggcgtc ataagaaccg catagttacc ctatggcgtc gttgtgtgtg ttcaagagaa   4080
atagcggttt tagtgcggtt tattattgcc ctggatacgg acaaaacaga gattgaaccg   4140
atgaccggcg ttattaaggt atcagttctc gtagtgtcag agacgtagac cttgaagagg   4200
```

-continued

```
accagagagt cgaccccggt gacagccgta gtactaacct cacgaccaac cccaacgaga   4260

ctatatcaaa aatagagctc cttaaggacg tcgggcccaa aaatatcgat taatcagttt   4320

acactcaatt ataatcatat gatgtaatga ttaaataatg tataagtaaa tatagttaga   4380

tcatcgtaaa tcgaaaatat tttgttatat tgacttatca tgtatgaaat gattattcaa   4440

tatttattct ctatgtataa atatcataaa atgaaagatg tgacttatat tattatatta   4500

atatgtttat attaaaaatt atgatatatc atatattgac tttattttat ggtcacatta   4560

tatcaataat atgtaaatat ggtgtagttt ctactcaata ttgtagtcac agtgacaatc   4620

gttgtcatca atatgctact catcaatgag agcataccgc aatcatacat acatagaaga   4680

tcaaaagaat catccgtaat atcctttgca gttcgaatat tccaataatt accatagatc   4740

tttatataga taatatggca aagagttgaa cccttatcgg ctaaacgaca aacactataa   4800

gtatggaaat atgtaatata tgtatgattc attaaaggta accgtaaaac catttcgtga   4860

aacattttaa tcaagaaaga aaaaatgaag attgtacaaa cgttcatata aaaattattg   4920

acattattcg catatatcta tacattttta atgggaagga cctaaatgga tatttataca   4980

attgtaatct ttatacatgt aatgatataa aaagtatacc taataaagat aatatgatcc   5040

ctaaggacga gaaatgaaat ctttatgata gcattgtttt ttattgctgt gcgacacata   5100

attagtaata gtactattat ctctttaacg acttaactaa atgtttcaat aatagacata   5160

gtctaaataa aatcctatgg atgatggatg ctattaatat gagcatacga tatgcaatga   5220

ctagatgtct tgattgttac gtacagctgc gccggcgtt                          5259
```